US011078177B2

(12) United States Patent
Dobelmann-Mara et al.

(10) Patent No.: US 11,078,177 B2
(45) Date of Patent: *Aug. 3, 2021

(54) COMPOUNDS FOR OPTICALLY ACTIVE DEVICES

(71) Applicant: Merck Patent GmbH, Darmstadt (DE)

(72) Inventors: Lars Dobelmann-Mara, Darmstadt (DE); Stefan Riedmueller, Frankfurt am Main (DE); Martin Schraub, Alsbach-Haehnlein (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/560,265

(22) Filed: Sep. 4, 2019

(65) Prior Publication Data

US 2019/0389829 A1    Dec. 26, 2019

Related U.S. Application Data

(62) Division of application No. 15/753,192, filed as application No. PCT/EP2016/001339 on Aug. 3, 2016, now Pat. No. 10,457,658.

(30) Foreign Application Priority Data

Aug. 21, 2015  (EP) .................... 15182029

(51) Int. Cl.
| | |
|---|---|
| *A61L 27/16* | (2006.01) |
| *A61L 27/50* | (2006.01) |
| *C08F 20/30* | (2006.01) |
| *C08F 20/38* | (2006.01) |
| *C08F 20/40* | (2006.01) |
| *G02B 1/04* | (2006.01) |
| *C07D 311/16* | (2006.01) |
| *C07D 335/06* | (2006.01) |

(52) U.S. Cl.
CPC ............ *C07D 311/16* (2013.01); *A61L 27/16* (2013.01); *A61L 27/50* (2013.01); *C07D 335/06* (2013.01); *C08F 20/30* (2013.01); *C08F 20/38* (2013.01); *C08F 20/40* (2013.01); *G02B 1/041* (2013.01)

(58) Field of Classification Search
None
See application file for complete search history.

(56) References Cited

U.S. PATENT DOCUMENTS

| | | | |
|---|---|---|---|
| 3,351,482 A | 11/1967 | Raue | |
| 3,420,835 A | 1/1969 | Wirth | |
| 4,349,619 A | 9/1982 | Kamoshida et al. | |
| 4,785,004 A | 11/1988 | Von Sprecher | |
| 5,290,892 A | 3/1994 | Namdaran | |
| 5,331,073 A | 7/1994 | Weinschenk, III | |
| 5,693,095 A | 12/1997 | Freeman | |
| 6,143,766 A | 11/2000 | Kaltenbronn | |
| 6,201,087 B1 | 3/2001 | Schuster | |
| 6,331,562 B1 | 12/2001 | Bhagwat | |
| 7,247,646 B2 | 7/2007 | McKie et al. | |
| 7,642,364 B2 | 1/2010 | Liu et al. | |
| 8,329,842 B2 | 12/2012 | Ritter | |
| 8,366,963 B2 | 2/2013 | Goto et al. | |
| 8,592,007 B2 | 11/2013 | Goetz et al. | |
| 9,315,496 B2 | 4/2016 | Zhang | |
| 10,457,658 B2* | 10/2019 | Dobelmann-Mara | ..................... C08F 20/40 |
| 2005/0054586 A1 | 3/2005 | Bartels | |
| 2006/0147840 A1 | 7/2006 | Ishidai | |
| 2007/0037876 A1 | 2/2007 | Liu | |
| 2009/0157178 A1 | 6/2009 | Hampp | |
| 2010/0324165 A1 | 12/2010 | Ritter | |
| 2011/0028667 A1* | 2/2011 | Ritter | ..................... A61L 27/16 526/270 |
| 2011/0092612 A1 | 4/2011 | Miki | |
| 2011/0205482 A1 | 8/2011 | Goetz | |
| 2011/0245919 A1* | 10/2011 | Pettit | ..................... A61F 2/1659 623/6.22 |
| 2012/0305843 A1 | 12/2012 | Klasen-memmer | |
| 2013/0114010 A1* | 5/2013 | Goetz | ..................... C09K 19/32 349/33 |
| 2015/0048276 A1 | 2/2015 | Goebel | |
| 2016/0159763 A1 | 6/2016 | Taugerbeck | |
| 2018/0237410 A1 | 8/2018 | Dobelmann-Mara | |

FOREIGN PATENT DOCUMENTS

| | | | |
|---|---|---|---|
| CN | 102532015 A | 7/2012 | |
| CN | 104656272 A * | 5/2015 | ............... G02C 7/12 |
| CN | 105753837 A | 7/2016 | |
| EP | 1683792 A1 | 7/2006 | |
| EP | 1958945 A1 | 8/2008 | |
| EP | 698369 A1 | 2/2014 | |

(Continued)

OTHER PUBLICATIONS

Kurosawa et al., "Analysis of stereoisomeric C27-bile acids by high performance liquid chromatography with fluorescence detection" Journal of Pharmaceutical and Biomedical Analysis, 1997, 15, 1375-1382.

Parenti et al., "Three-Dimensional Quantitative Structure—Activity Relationship Analysis of a Set of Plasmodium falciparum Dihydrofolate Reductase Inhibitors Using a Pharmacophore Generation Approach"; Journal of Medicinal Chemistry, 2004, 47, 17, 4258-4267 plus Suppl. Material.

Matos et al., "Insight into the Interactions between Novel Coumarin Derivatives and Human A3 Adenosine Receptors" ChemMedChem, 2014, 9, 2245-2253.

You et al.,"Discovery of novel osthole derivatives as potential anti-breast cancer treatment"; Bioorganic & Medicinal Chemistry Letters, 2010, 20, 7426-7428.

(Continued)

*Primary Examiner* — Nicole M. Buie-Hatcher
(74) *Attorney, Agent, or Firm* — Millen White Zelano and Branigan, PC; John Sopp

(57) ABSTRACT

The present invention relates to novel compounds, particularly to compounds comprising a photoactive unit, said novel compounds being particularly suitable for ophthalmic devices as well as to ophthalmic devices comprising such compounds.

12 Claims, No Drawings

(56) References Cited

FOREIGN PATENT DOCUMENTS

| | | |
|---|---|---|
| EP | 2837671 B1 | 10/2017 |
| FR | 2118191 A5 | 7/1972 |
| JP | 57035850 A | 2/1982 |
| JP | 3275681 A | 12/1991 |
| JP | 5263072 A | 10/1993 |
| JP | 02876129 B2 | 3/1999 |
| JP | 2007505835 A | 3/2007 |
| JP | 2007510674 A | 4/2007 |
| JP | 2012506878 A | 3/2012 |
| JP | 2012124297 A | 6/2012 |
| WO | 2005028472 A1 | 3/2005 |
| WO | 2007033831 A1 | 3/2007 |
| WO | 20070066755 | 3/2007 |
| WO | 07066755 A1 | 6/2007 |
| WO | 08096673 A1 | 8/2008 |
| WO | 2009/074520 A2 | 6/2009 |
| WO | 2009/074521 A1 | 6/2009 |
| WO | 2010/049044 A1 | 5/2010 |
| WO | 2010086484 A1 | 8/2010 |
| WO | 2011/098224 A1 | 8/2011 |
| WO | 2012097858 A1 | 7/2012 |
| WO | 2014090362 A1 | 6/2014 |
| WO | 2016200401 A1 | 12/2015 |

OTHER PUBLICATIONS

First Office action in corresponding JP appl. 2018-509835 dispatched Jul. 7, 2020 (pp. 1-4).
Waldmann : "Reagent-controlled domino synthesis of skeletally-diverse compound collections" Chemical Communications 2008,10,1211-1213, Abstract.
International Search Report PCT/EP2016/001341 dated Sep. 22, 2016.
Carrer, Adv Synth Catal, vol. 355, 2013, 2044-2054. (Year: 2013).
Wu Chem Lett, vol. 34(4), 550-551, 2005. (Year: 2005).
Wang, Adv Synth Catal, vol. 349, 1943-1948,2007. (Year: 2007).
Cheng, Bioort & Med Chem Lett, vol. 14, 2411-2415, 2004. (Year: 2004).
International Search Report PCT/EP2016/001340 dated Sep. 23, 2016.
Liao, J.H. et al.: "Anti-UVC Irradiation and Metal Chelation Properties of 6-Benzoyl-5,7-dihydroxy-4-phenyl-chromen-2-one: An Implication for Anti-Cataract Agent", Int. J. Mol. Sci., vol. 12, 2011, pp. 7059-7076, XP002761569.
International Search Report PCT/EP2016/001339 dated Oct. 6, 2016.
E. Tang et al: "A Convenient Solid-Phase Synthesis of Coumarins by TMSOTf-Catalyzed Intramolecular Seleno-Arylation of Tethered Alkenes", Synlett, vol. 23, No. 06, Mar. 15, 2012 (Mar. 15, 2012), DE, pp. 907-912, XP055241177, ISSN: 0936-5214.
Lodovico Lunazzi et al: "Stereomutation of Axially Chiral Aryl Coumarins", The Journal of Organic Chemistry, vol. 75, No. 17, Sep. 3, 2010 (Sep. 3, 2010), US, pp. 5927-5933, XP055241172, ISSN: 0022-3263, DOI: 10.1021/jo101261k.
Xiao-Feng Wu et al: "A General Palladium-Catalyzed Carbonylative Synthesis of Chromenones from Salicylic Aldehydes and Benzyl Chlorides", Chemistry—A European Journal., vol. 19, No. 37, Sep. 9, 2013 (Sep. 9, 2013), Weinheim, DE, pp. 12245-12248, XP055241154, ISSN: 0947-6539.
Weiying Lin et al: "Through-Bond Energy Transfer Cassettes with Minimal Spectral Overlap between the Donor Emission and Acceptor Absorption: Coumarin-Rhodamine Dyads with Large Pseudo-Stokes Shifts and Emission Shifts", Angewandte Chemie International Edition, vol. 49, No. 2, Jan. 8, 2010 (Jan. 8, 2010), DE, pp. 375-379, XP055241144, ISSN: 1433-7851.
O. S. Filipenko et al: "Effect of intermolecular interactions on the formation of mesophases in 3-aryl-7-substituted coumarins, and the crystal structure of 3-(4?-butyl)- and (4?-heptylphenyl)-7-propoxycoumarins", Bulletin of the Academy of Sciences of the USSR, Division of Chemical Sciences., vol. 38, No. 10, Oct. 1, 1989 (Oct. 1, 1989), US, pp. 2073-2079, XP055241135, ISSN: 0568-5230.
Dolores Viña et al: "8-Substituted 3-Arylcoumarins as Potent and Selective MAO-B Inhibitors: Synthesis, Pharmacological Evaluation, and Docking Studies", Chemmedchem, vol. 7, No. 3, Mar. 5, 2012 (Mar. 5, 2012), DE, pp. 464-470, XP055241043, ISSN: 1860-7179.
Xiaoping Chen et al: "Synthesis of Novel Polymer/Urea Peptoid Conjugates Using RAFT Polymerization", Macromolecules, vol. 43, No. 3, Feb. 9, 2010 (Feb. 9, 2010), US, pp. 1341-1348, XP055241030, ISSN: 0024-9297.
Sébastien L. Degorce et al: "Investigation of ( E )-3-[-4-(2-Oxo-3-aryl-chromen-4-yl)oxyphenyl]acrylic Acids as Oral Selective Estrogen Receptor Down-Regulators", Journal of Medicinal Chemistry, vol. 58, No. 8, Apr. 23, 2015 (Apr. 23, 2015), US, pp. 3522-3533, XP055240905, ISSN: 0022-2623.
Farnaz Jafarpour et al: "Palladium-Catalyzed Decarboxylative Cross-Coupling Reactions: A Route for Regioselective Functionalization of Coumarins", The Journal of Organic Chemistry, vol. 78, No. 7, Apr. 5, 2013 (Apr. 5, 2013), US, pp. 2957-2964, XP055240707, ISSN: 0022-3263.
N A Gordeeva et al: "Photochemical Reactions of 7-Aminocoumarins. 8*. Reaction of 3-IODO-4-Methyl-7-Diethylaminocoumarin With Monosubstituted Benzenes", Chemistry of Heterocyclic Compounds, Jan. 1, 1990 (Jan. 1, 1990), pp. 976-980, XP055240705, Retrieved from the Internet [retrieved on Jan. 12, 2016].
Schraub Martin et al: "Photoinduced refractive index changes of 3-phenyl-coumarin containing polymers for ophthalmic applications", European Polymer Journal, Pergamon Press Ltd. Oxford, GB, vol. 51, Dec. 1, 2013 (Dec. 1, 2013), pp. 21-27, XP028810223, ISSN: 0014-3057.
Schraub Martin et al: "Smart polymers containing substituted coumarin side groups enable photo-induced tuning of focal length of intraocular lenses", Ophthalmic Technologies XXI, SPIE, 1000 20th St. Bellingham WA 98225-6705 USA, vol. 7885, No. 1, Feb. 10, 2011 (Feb. 10, 2011), pp. 1-11, XP060005764.
Kapoor et al., "Synthesis of coumarins", Labdev (Kanpur, India), 1966, 4(1),27-29 (Year: 1966).
Trager et al., "Polymers for in vivo Tuning of Refractive Properties in Intraocular Lenses", Macromol. Biosci. 2008, 8, 177-183 (Year: 2008).
Schraub et al. "Smart polymers containing substituted coumarin side groups enable photo-induced tuning of focal length of intraocular lenses", Proc. SPIE 7885, Ophthalmic Technologies XXI, 78851Z, Feb. 11, 2011; doi: 10.1117/12.873814. (Year: 2011).
Asif, "Overview of Diverse Pharmacological Activities of Substituted Coumarins" Compounds with Therapeutic Potentials, American Journal of Current Organic Chemistry, vol. 1, Issue 1, Jan. 21, 2015, 16 pages. (Year 2015).
Search report in corresponding EP application No. 17156321 dated May 2, 2017 (1 Page).
Search report in corresponding EP application No. 17156327 dated May 2, 2017 (2 Pages).
Search report in corresponding EP application No. 17156324 dated Apr. 27, 2017 (2 Pages).
Search report in corresponding EP application No. 17156329 dated Mar. 22, 2017 (3 Pages).
Search report in corresponding EP application No. 17156326 dated Mar. 22, 2017 (3 Pages).
Search report in corresponding EP application No. 17156331 dated Mar. 24, 2017 (2 Pages).
N. K. Sangwan et al., Indian Journal of Chemistry, 1990, vol. 29B, pp. 294-296.
Nasu; J. Mater. Chem., 2010, 20, 6688-6695.
Schmidt: Pure Appl. Chem. 1971, 27, 647-678.
Mi Sun Lee et al., Journal of Applied Polymer Science, 2012, vol. 124, 4339-4345.
Jenkins ; Pure Appl. Chem. 1996, vol. 68, No. 12 ; 2287-1231.
C.H. Krauch et al, Chemische Berichte Jahrg. 99, 1966, 1723.
A. Buquet et al, Tetrahedron, 1981, vol. 37, 75 to 81.
David L. Oldroyd et al, Tetrahedron Letters, 1993, vol. 34, No. 7, 1087-1090.

(56) References Cited

OTHER PUBLICATIONS

J. M. G. Cowie, Polymers: Chemistry & Physics of Modern Materials, Blackie, Glasgow, 1991.
T. Truong et al, JACS, 2014, vol. 136, No. 24, p. 8568-8576.
P. L. Beaulieu et al., Journal of Medicinal Chemistry, 2012, vol. 55, No. 17, p. 7650-7666.
J.-M. Legeais, J. Cataract. Refract. Surg., 1998, 24, 371-379.
Australian Examination report in corresponding AU application 2016312305 dated Nov. 4, 2020 (pp. 1-9).
Report with CAS Registry No. 376382-75-1 ( STN date Dec. 18, 2001), CAS Registry No. 376380-44-8 ( STN date Dec. 18, 2001), CAS Registry No. 376378-98-2 (STN date Dec. 18, 2001).
Arnoldi, A., et al., Analogues of Phytoalexins. Syntheis of Some 3-Phenylcoumarins and Their Fungicidal Activity, J. Agric. Food Chem., (1986), vol. 34, No. 2, pp. 185-188.

\* cited by examiner

COMPOUNDS FOR OPTICALLY ACTIVE DEVICES

TECHNICAL FIELD

The present invention relates to novel compounds, particularly to compounds comprising a photoactive unit, said novel compounds being particularly suitable for ophthalmic devices as well as to ophthalmic devices comprising such compounds.

BACKGROUND AND DESCRIPTION OF THE PRIOR ART

Cataract is a general term of an affection of the eye that leads to a loss of vision and in the extreme to blindness by clouding of the normally clear lens of the eye.

It is the major cause of blindness in the world with it affecting more than 100 million people. Due to the fact that its major cause is age, it is expected that with the population's average age continuing to increase the number of cataracts will continue to increase substantially in the future.

Effective treatment of cataract is only possible by surgical intervention, whereby the natural lens of the eye is removed through an incision in the cornea and replaced with an artificial lens, often also referred to as "intraocular lens". In preparation of surgery current state-of-the-art surgical methods employ methods for eye mapping so as to approximate the refractive power best suited to the respective patient.

Even though cataract surgery is one of the most widely used and safest surgical procedures it is not without specific post-surgery problems. It frequently happens that the refractive power of the implanted intraocular lens (IOL) is insufficient for restoring good vision. Such problems may, for example, be caused by changes in eye geometry in consequence of the surgery as well as irregular wound healing and positioning errors that result in the artificial lens not having the optimal optical properties. As a result the patient will still require corrective vision aids, e.g. glasses, to be able to see correctly. In some cases the resulting refractive power of the implanted artificial lens is so far removed from the required refractive power that further surgery will be required. Particularly for aged persons this is not desirable because the body's capability for healing are reduced with increasing age. Furthermore, there is the risk of attracting endophthalmitis, an inflammation of the eye, which can even lead to a complete loss of vision or worse, loss of the eye.

There is therefore a need in the health sector for optically active devices, and particularly artificial intraocular lenses, that would allow for non-invasive adjustment of refractive power after implantation of the lens, thereby preferably further reducing the need for post-surgery vision aids.

Some developments in this sense have already been made, as for example evidenced by WO 2007/033831 A1.

However, the compounds disclosed therein suffer from being too stiff and too brittle so that they can't be rolled or folded and are thus not fit to be implanted by state of the art cataract surgical methods, particularly by state of the art micro-incision cataract surgical methods.

Consequently, it is an objective of the present application to provide for novel compounds suitable for ophthalmic devices.

It is also an objective of the present application to provide for compounds, the optical properties of which may be changed, preferably by non-invasive techniques.

It is a further objective of the present application to provide for novel compounds that are more flexible than the currently known compounds, preferably in combination with being suitable for ophthalmic devices.

Further advantages and objectives of the compounds of the present application will be evident to the skilled person from the following detailed description as well as from the examples.

SUMMARY OF THE INVENTION

The present inventors have now surprisingly found that the above objects may be attained either individually or in any combination by the compounds and ophthalmic devices of the present application.

The present application therefore provides for a compound of formula (I)

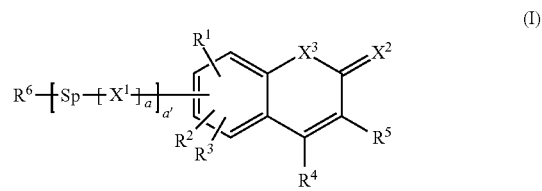

wherein
a is 0 or 1;
a' is 0 or 1;
$R^2$ and $R^3$ are at each occurrence independently selected from the group consisting of H, F, Cl, Br, I, alkyl having from 1 to 20 carbon atoms, partially or completely halogenated alkyl having from 1 to 20 carbon atoms, aryl and heteroaryl;
one of $R^4$ and $R^5$ is a group of formula (II)

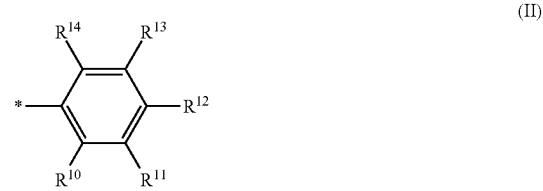

and the other of $R^4$ and $R^5$ is selected from the group consisting of H, F, Cl, Br, I, alkyl having from 1 to 20 carbon atoms, partially or completely halogenated alkyl having from 1 to 20 carbon atoms, aryl, heteroaryl, and $R^6$-Sp-$[X^1]_{a}$-*;
$R^6$ is a carbyl group for a'=1 and for a'=0 is selected from the group consisting of H, F, Cl, Br, I, alkyl having from 1 to 20 carbon atoms, partially or completely halogenated alkyl having from 1 to 20 carbon atoms, aryl and heteroaryl;
Sp is selected from the group consisting of alkanediyl, alkenediyl and alkyndiyl;
$X^1$ and $X^2$ are independently of each other selected from the group consisting of O, S and N—$R^{17}$;
$X^3$ is O or S;
$R^{10}$, $R^{11}$, $R^{12}$, $R^{13}$ and $R^{14}$ are at each occurrence independently of each other selected from the group consisting of H, F, Cl, Br, I, $R^6$-Sp-$[X^1]_{a}$-*, alkyl having from 1 to 20 carbon atoms, partially or completely halogenated alkyl having from 1 to 20 carbon atoms, aryl and heteroaryl, provided that at least one of $R^{10}$, $R^{11}$, $R^{12}$, $R^{13}$ and $R^{14}$ is $R^{15}$;

$R^{15}$ is at each occurrence independently selected from the group consisting of alkyl having from 1 to 20 carbon atoms and partially or completely halogenated alkyl having from 1 to 20 carbon atoms; and $R^{17}$ is at each occurrence independently selected from the group consisting of H, F, Cl, Br, I, alkyl having from 1 to 20 carbon atoms, partially or completely halogenated alkyl having from 1 to 20 carbon atoms, aryl and heteroaryl, provided that the compound of formula (I) comprises at least one group $R^6$-Sp-$[X^1]_a$-*.

The present application also provides for a composition comprising said compound as well as for an article comprising said composition.

In addition, the present application provides for a process of forming such article, said process comprising the steps of
a) providing a composition comprising said compound;
b) subsequently forming the article of said composition.

Furthermore, the present application provides for a process for changing the optical properties of such article, said process comprising the steps of
a) providing said article, and
b) subsequently exposing said article to irradiation having a wavelength of at least 200 nm and at most 1500 nm.

DETAILED DESCRIPTION OF THE INVENTION

For the purposes of the present application an asterisk ("*") denotes a linkage to an adjacent unit or group or, in case of a polymer, to an adjacent repeating unit or any other group.

For the purposes of the present application the term "organyl group" is used to denote any organic substituent group, regardless of functional type, having one free valence at a carbon atom.

For the purposes of the present application the term "organoheteryl group" is used to denote any univalent group comprising carbon, said group thus being organic, but having the free valence at an atom other than carbon.

For the purposes of the present application the term "carbyl group" includes both, organyl groups and organoheteryl groups.

As used herein, the term "carbyl group" will be understood to include any monovalent or multivalent organic radical moiety which comprises at least one carbon atom either without any non-carbon atoms (like for example —C≡C—), or optionally comprising one or more heteroatoms (for example carbonyl etc.).

The term "hydrocarbyl group" will be understood to mean a carbyl group that does additionally contain one or more H atoms and optionally contains one or more hetero atoms.

As used herein, the term "hetero atom" will be understood to mean an atom in an organic compound that is not a H- or C-atom, and preferably will be understood to mean N, O, S, P, Si, Se, As, Te or Ge, more preferably N, O, S, P and Si.

The compound of the present application is of the following formula (I)

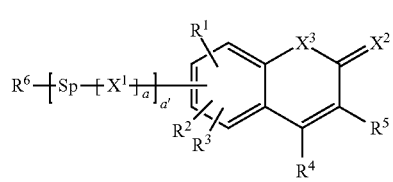
(I)

wherein a, a', $R^1$, $R^2$, $R^3$, $R^4$, $R^5$, $R^6$, Sp, $X^1$, $X^2$, $X^3$ and $X^4$ are as defined herein, provided that the compound of formula (I) comprises one group $R^6$-Sp-$[X^1]_a$-* as defined herein. The expression "comprises one group $R^6$-Sp-$[X^1]_a$-*" is to denote in this context that the compound of formula (I) comprises only one such group.

The compound of formula (I) is preferably a compound of formula (I') or a compound of formula (I'').

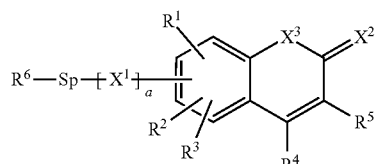
(I')

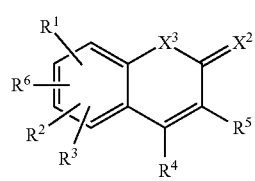
(I'')

a is 0 or 1. Preferably a is 1.

a'—if present—is 0 or 1.

$R^1$-, $R^2$ and $R^3$ are at each occurrence independently selected from the group consisting of H, F, Cl, Br, I, alkyl having from 1 to 20 carbon atoms, partially or completely halogenated alkyl having from 1 to 20 carbon atoms, aryl and heteroaryl. Most preferably, $R^1$, $R^2$ and $R^3$ are all H.

One or both, preferably one of $R^4$ and $R^5$ is a group of formula (II)

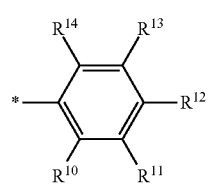
(II)

with $R^{10}$, $R^{11}$, $R^{12}$, $R^{13}$ and $R^{14}$ as defined herein. If only one of $R^4$ and $R^5$ is a group of formula (II), the other of $R^4$ and $R^5$ is selected from the group consisting of H, F, Cl, Br, I, alkyl having from 1 to 20 carbon atoms, partially or completely halogenated alkyl having from 1 to 20 carbon atoms, aryl, heteroaryl, and $R^6$-Sp-$[X^1]_a$-*. Preferably $R^4$ is H and $R^5$ is a group of formula (II) as defined herein.

$R^{10}$, $R^{11}$, $R^{12}$, $R^{13}$ and $R^{14}$ are at each occurrence independently of each other selected from the group consisting of H, F, Cl, Br, I, $R^6$-Sp-$[X^1]_a$-* and $R^{15}$ as defined herein. Preferably $R^{10}$, $R^{11}$, $R^{12}$, $R^{13}$ and $R^{14}$ are at each occurrence independently of each other selected from the group consisting of H, F, and $R^{15}$ as defined herein.

Preferably at least one (for example, two, three, four or all) of $R^{10}$, $R^{11}$, $R^{12}$, $R^{13}$ and $R^{14}$, more preferably at least one (for example, two or all) of $R^{10}$, $R^{12}$ and $R^{14}$, even more preferably at least one or all of $R^{10}$ and $R^{14}$, still even more preferably $R^{10}$ only, and most preferably all of $R^{10}$, $R^{11}$, $R^{12}$, $R^{13}$ and $R^{14}$ is/are H.

Preferably for the compound of formula (I') one or both, preferably one, of $R^4$ and $R^5$ is a group of formula (II) with $R^{10}$, $R^{11}$, $R^{12}$, $R^{13}$ and $R^{14}$ being at each occurrence independently of each other selected from the group consisting of H, F, Cl, Br, I, and $R^{15}$ as defined herein and preferably with $R^{10}$, $R^{11}$, $R^{12}$, $R^{13}$ $R^{14}$ being at each occurrence independently of each other selected from the group consisting of H, F, and $R^{15}$ as defined herein, wherein any two adjacent groups of $R^{10}$, $R^{11}$, $R^{12}$, $R^{13}$ and $R^{14}$ that are $R^{15}$ may also form a ring system; and if only one of $R^4$ and $R^5$ is a group of formula (II), the other of $R^4$ and $R^5$ is selected from the group consisting of H, F, Cl, Br, I, alkyl having from 1 to 20 carbon atoms, partially or completely halogenated alkyl having from 1 to 20 carbon atoms, aryl and heteroaryl.

For the compound of formula (I'') one of groups $R^{10}$, $R^{11}$, $R^{12}$, $R^{13}$ and $R^{14}$ is $R^6$-Sp-$[X^1]_a$-*. Thus, preferably for such compound one or both, preferably one, of $R^4$ and $R^5$ is a group of formula (II) with one of $R^{10}$, $R^{11}$, $R^{12}$, $R^{13}$ and $R^{14}$ being $R^6$-Sp-$[X^1]_a$-* and the others being at each occurrence independently of each other selected from the group consisting of H, F, Cl, Br, I, and $R^{15}$ as defined herein, wherein any two adjacent groups of $R^{10}$, $R^{11}$, $R^{12}$, $R^{13}$ and $R^{14}$ that are $R^{15}$ may also form a ring system.

Alternatively, for the compound of formula (I'') one group $R^4$ and $R^5$ is $R^6$-Sp-$[X^1]_a$-*. Thus, preferably for such compound one of $R^4$ and $R^5$ is $R^6$-Sp-$[X^1]_a$-* and the other of $R^4$ and $R^5$ is a group of formula (II) with $R^{10}$, $R^{11}$, $R^{12}$, $R^{13}$ and $R^{14}$ being at each occurrence independently of each other selected from the group consisting of H, F, Cl, Br, I, and $R^{15}$ as defined herein and preferably with $R^{10}$, $R^{11}$, $R^{12}$, $R^{13}$ and $R^{14}$ being at each occurrence independently of each other selected from the group consisting of H, F, and $R^{15}$ as defined herein, wherein any two adjacent groups of $R^{10}$, $R^{11}$, $R^{12}$, $R^{13}$ and $R^{14}$ that are $R^{15}$ as may also form a ring system.

$R^{15}$ is at each occurrence independently selected from the group consisting of alkyl having from 1 to 20 carbon atoms and partially or completely halogenated (preferably fluorinated) alkyl having from 1 to 20 carbon atoms. More preferably, $R^{15}$ is at each occurrence independently selected from the group consisting of partially or completely halogenated (preferably fluorinated) alkyl having from 1 to 20 (for example, from 1 to 10 or from 1 to 5, or from 1 to 3, or 1) carbon atoms. Most preferably, $R^{15}$ is —$CF_3$.

$R^{15}$ is at each occurrence independently selected from the group consisting of alkyl having from 1 to 20 carbon atoms, partially or completely halogenated (preferably fluorinated) alkyl having from 1 to 20 carbon atoms, alkoxy having from 1 to 20 carbon atoms, partially or completely halogenated alkoxy having from 1 to 20 carbon atoms, thioalkyl having from 1 to 20 carbon atoms, and partially or completely halogenated thioalkyl having from 1 to 20 carbon atoms. More preferably, $R^{15}$ is at each occurrence independently selected from the group consisting of partially or completely halogenated (preferably fluorinated) alkyl having from 1 to 20 (for example, from 1 to 10 or from 1 to 5, or from 1 to 3, or 1) carbon atoms. Most preferably, $R^{15}$ is —$CF_3$.

Any two adjacent groups of $R^{10}$, $R^{11}$, $R^{12}$, $R^{13}$ and $R^{14}$ that are $R^{15}$ may also form a ring system, preferably a six-membered ring system. Such ring system may be aromatic or non-aromatic. Such ring system, if non-aromatic, may be saturated or unsaturated, for example comprising a double bond. Optionally such ring system may be substituted, i.e. one or more of the hydrogens is replaced with H, F, Cl, Br, I, alkyl having from 1 to 20 carbon atoms, partially or completely halogenated alkyl having from 1 to 20 carbon atoms, aryl and heteroaryl.

$R^6$ is a carbyl group for a'=1 and for a'=0 is selected from the group consisting of H, F, Cl, Br, I, alkyl having from 1 to 20 carbon atoms, partially or completely halogenated alkyl having from 1 to 20 carbon atoms, aryl and heteroaryl.

A carbyl or hydrocarbyl group comprising a chain of 3 or more C atoms may be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 30 C atoms, wherein all these groups do optionally contain one or more hetero atoms, preferably selected from N, O, S, P, Si, Se, As, Te and Ge, more preferably N, O, S, P and Si.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups. Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_3$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

The terms "aryl" and "heteroaryl" as used herein preferably mean a mono-, bi- or tricyclic aromatic or heteroaromatic group with 4 to 30 ring C atoms that may also comprise condensed rings and is optionally substituted with one or more groups L, wherein L is selected from halogen, —CN, —NC, —NCO, —NCS, —OCN, —SCN, —C(=O)$NR^0R^{00}$, —C(=O)$X^0$, —C(=O)$R^0$, —$NH_2$, —$NR^0R^{00}$, —SH, —$SR^0$, —$SO_3H$, —$SO_2R^0$, —OH, —$NO_2$, —$CF_3$, —$SF_5$, or carbyl or hydrocarbyl with 1 to 40 C atoms that is optionally substituted and optionally comprises one or more hetero atoms, and is preferably alkyl, alkoxy, thioalkyl, alkylcarbonyl, alkoxycarbonyl or alkoxycarbonyloxy with 1 to 20 C atoms that is optionally fluorinated, and $R^0$, $R^{00}$ and $X^0$ have the meanings given above and below.

$R^0$, $R^{00}$ and $R^{000}$ are at each occurrence independently of each other selected from the group consisting of H, F and hydrocarbyl having from 1 to 40 carbon atoms. Said hydrocarbyl preferably has at least 5 carbon atoms. Said hydrocarbyl preferably has at most 30, more preferably at most 25 or 20, even more preferably at most 20, and most preferably at most 12 carbon atoms. Preferably, $R^0$, $R^{00}$ and $R^{000}$ are at each occurrence independently of each other selected from the group consisting of H, F, alkyl, fluorinated alkyl, alkenyl, alkynyl, phenyl and fluorinated phenyl. More preferably, $R^0$, $R^{00}$ and $R^{000}$ are at each occurrence independently of each other selected from the group consisting of H, F, alkyl, fluorinated, preferably perfluorinated, alkyl, phenyl and fluorinated, preferably perfluorinated, phenyl.

It is noted that for example alkyl suitable as $R^O$, $R^{OO}$ and $R^{OOO}$ also includes perfluorinated alkyl, i.e. alkyl wherein all of the hydrogen are replaced by fluorine. Examples of suitable alkyls may be selected from the group consisting of methyl, ethyl, n-propyl, iso-propyl, n-butyl, iso-butyl, tert-butyl (or "t-butyl"), pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl ($—C_{20}H_{41}$).

$X^O$ is halogen. Preferably $X^O$ is selected from the group consisting of F, Cl and Br.

Very preferred substituents L are selected from halogen, most preferably F, or alkyl, alkoxy, oxoalkyl, thioalkyl, fluoroalkyl and fluoroalkoxy with 1 to 12 C atoms or alkenyl and alkynyl with 2 to 12 C atoms.

Especially preferred aryl and heteroaryl groups are phenyl, phenyl wherein one or more CH groups are replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b; 4,5-b']dithiophene, benzo[2,1-b; 3,4-b']dithiophene, quinole, 2- methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with L as defined above.

An alkyl or alkoxy radical, i.e. where the terminal $CH_2$ group is replaced by —O—, can be straight-chain or branched. It is preferably straight-chain (or linear). Suitable examples of such alkyl and alkoxy radical are methyl, ethyl, n-propyl, iso-propyl, n-butyl, sec-butyl, tert-butyl, pentyl, hexyl, heptyl, octyl, nonyl, decyl, undecyl, dodecyl, tridecyl, tetradecyl, pentadecyl, methoxy, ethoxy, propoxy, butoxy, pentoxy, hexoxy, heptoxy, octoxy, nonoxy, decoxy, ethylhexyl, undecoxy, dodecoxy, tridecoxy or tetradecoxy. Preferred alkyl and alkoxy radicals have 1, 2, 3, 4, 5, 6, 7, 8, 9 or 10 carbon atoms. Suitable examples of such preferred alkyl and alkoxy radicals may be selected from the group consisting of methyl, ethyl, n-propyl, iso-propyl, n-butyl, sec-butyl, tert-butyl, pentyl, hexyl, heptyl, octyl, nonyl, decyl, ethylhexyl, methoxy, ethoxy, propoxy, butoxy, pentoxy, hexoxy, heptoxy, octoxy, nonoxy and decoxy.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-enyl, prop-2-enyl, but-1-enyl, but-2-enyl, but-3-enyl, pent-1-enyl, pent-2-enyl, pent-3-enyl or pent-4-enyl, hex-1-enyl, hex-2-enyl, hex-3-enyl, hex-4-enyl or hex-5-enyl, hept-1-enyl, hept-2-enyl, hept-3-enyl, hept-4-enyl, hept-5-enyl or hept-6-enyl, oct-1-enyl, oct-2-enyl, oct-3-enyl, oct-4-enyl, oct-5-enyl, oct-6-enyl or oct-7-enyl, non-1-enyl, non-2-enyl, non-3-enyl, non-4-enyl, non-5-enyl, non-6-enyl, non-7-enyl or non-8-enyl, dec-1-enyl, dec-2-enyl, dec-3-enyl, dec-4-enyl, dec-5-enyl, dec-6-enyl, dec-7-enyl, dec-8-enyl or dec-9-enyl.

Especially preferred alkenyl groups are $C_2l_7$-1E-alkenyl, $C_4$-$C_7$-3E-alkenyl, $C_5$-$C_2$-4-alkenyl, alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_2$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Alkenyl groups having up to 5 C atoms are generally preferred.

An oxoalkyl group, i.e. where one $CH_2$ group is replaced by —O—, is preferably straight-chain 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-,6-,7-, 8- or 9-oxadecyl, for example. Oxaalkyl, i.e. where one $CH_2$ group is replaced by —O—, is preferably straight-chain 2-oxapropyl (=methoxymethyl), 2-(=(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably selected from the group consisting of acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, and 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably selected from the group consisting of bis-carboxy-methyl, 2,2-bis-carboxy-ethyl, 3,3-bis-carboxy-propyl, 4,4-bis-carboxy-butyl, 5,5-bis-ca rboxy-pentyl, 6,6-bis-ca rboxy-hexyl, 7,7-bis-ca rboxy-heptyl, 8,8-bis-ca rboxy-octyl, 9,9-bis-ca rboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-methyl, 4,4-bis-(methoxycarbonyl)-butyl, 5,5-bis-(methoxycarbonyl)-pentyl, 6,6-bis-(nnethoxyca rbonyI)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, and 5,5-bis-(ethoxycarbonyl)-hexyl.

A thioalkyl group, i.e where one $CH_2$ group is replaced by —S—, is preferably straight-chain thiomethyl ($—SCH_3$), 1-thioethyl ($—SCH_2CH_3$), 1-thiopropyl ($==SCH_2CH_2CH_3$), 1- (thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, in particular 1,1-difluoroalkyl, all of which are straight-chain or branched.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-meth-oxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), sec-butyl, tert-butyl, isopropoxy, 2-methyl-propoxy, 3-methylbutoxy, duryl and ethylhexyl In a preferred embodiment, the hydrocarbyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

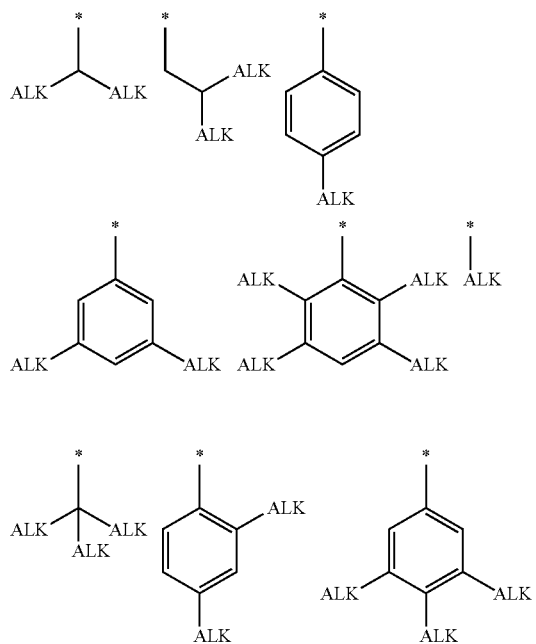

-continued

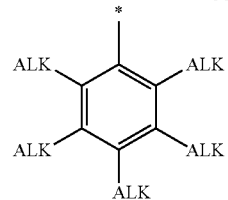

wherein "ALK" denotes optionally fluorinated alkyl or alkoxy with 1 to 20, preferably 1 to 12 C-atoms, in case of tertiary groups very preferably 1 to 9 C atoms.

Sp is selected from the group consisting of alkanediyl, alkenediyl and alkyndiyl (*—C≡C—*).

Preferably said alkanediyl has at least 1 carbon atom, more preferably at least 2 or 3 carbon atoms, even more preferably at least 4 carbon atoms, still even more preferably at least 5 carbon atoms, and most preferably at least 6 carbon atoms. Preferably said alkenediyl has at least 2 carbon atoms, more preferably at least 3 carbon atoms, even more preferably at least 4 carbon atoms, still even more preferably at least 5 carbon atoms, and most preferably at least 6 carbon atoms.

Preferably said alkyndiyl has at least 3 carbon atoms, more preferably at least 4 carbon atoms, even more preferably at least 5 carbon atoms, and most preferably at least 6 carbon atoms.

Preferably said alkanediyl, alkenediyl or alkyndiyl has at most 20 carbon atoms, more preferably at most 19 or 18 carbon atoms, even more preferably at most 17 or 16 carbon atoms, still even more preferably at most 15 or 14 carbon atoms and most preferably at most 13 or 12 carbon atoms.

Preferably, Sp selected from the group consisting of alkanediyl, alkenediyl and alkyndiyl (*—C≡C—*), wherein at least one, preferably at least two hydrogen has/have been replaced with $R^{16}$.

$R^{16}$ may be selected from the group consisting of OH, alkyl having from 1 to 10 (preferably from 1 to 5) carbon atoms, partially or completely halogenated (preferably fluorinated) alkyl having from 1 to 10 (preferably from 1 to 5) carbon atoms, alkoxy having from 1 to 10 (preferably from 1 to 5) carbon atoms, and partially or completely halogenated (preferably fluorinated) alkoxy having from 1 to 10 (preferably from 1 to 5) carbon atoms. Preferably $R^{16}$ is OH.

Sp may, for example, be represented by the following formula (III)

wherein b, $R^7$ and $R^8$ are as defined herein.

b is at least 1, preferably at least 2, more preferably at least 4, even more preferably at least 5. b is at most 20, preferably at most 19, more preferably at most 18, even more preferably at most 17, still even more preferably at most 16 and most preferably at most 15.

If b is at least two, two neighboring groups $C(R^7)(R^8)$ may be replaced by an alkenediyl.

If b is at least three, two neighboring groups $C(R^7)(R^8)$ may be replaced by an alkyndiyl.

$R^7$ and $R^8$ are independently of each other H or $R^{16}$. Preferably at least one of the $R^7$ and $R^8$ present is $R^{16}$. More preferably at least two of the $R^7$ and $R^8$ present are $R^{16}$.

Alternatively Sp may, for example, be represented by the following formulae (III-a)

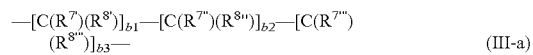

wherein $R^{7'}$, $R^{8'}$, $R^{7''}$, $R^{8''}$, $R^{7'''}$, $R^{8'''}$, b1, b2 and b3 are as defined herein.

The sum of b1, b2 and b3 is b, i.e. b1+b2+b3=b. Preferably, at least one of b1 or b3 is at least 1 and b2 is 1. More preferably b1, b2 and b3 are all at least 1. Most preferably b1 and b3 are at least 1 and b2 is 1.

If b1 is at least two, two neighboring groups $C(R^{7'})(R^{8'})$ may be replaced by an alkenediyl. If b2 is at least two, two neighboring groups $C(R^{7''})(R^{8''})$ may be replaced by an alkenediyl. If b3 is at least two, two neighboring groups $C(R^{7'''})(R^{8'''})$ may be replaced by an alkenediyl.

If b1 is at least two, two neighboring groups $C(R^{7'})(R^{8'})$ may be replaced by an alkyndiyl. If b2 is at least two, two neighboring groups $C(R^{7''})(R^{8''})$ may be replaced by an alkyndiyl. If b3 is at least two, two neighboring groups $C(R^{7'''})(R^{8'''})$ may be replaced by an alkyndiyl.

Preferably $R^{7'}$, $R^{8'}$, $R^{7''''}$ and $R^{8-''''}$—if present—are H and at least one of $R^{7''}$ and $R^{8''}$ is $R_{16}$.

Suitable examples of Sp may be selected from the following formulae (III-1) to (III-10)

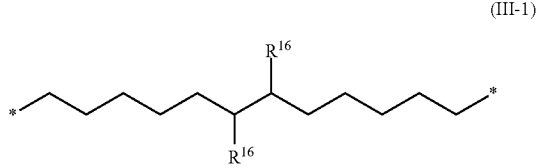

(III-1)

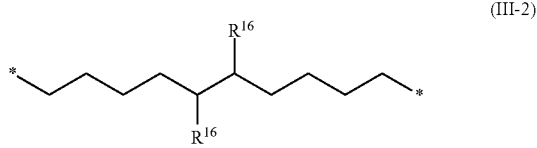

(III-2)

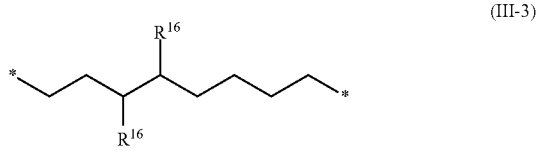

(III-3)

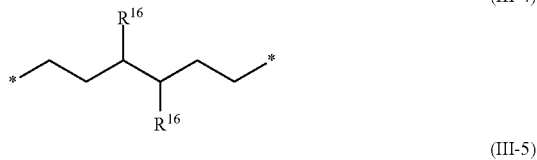

(III-4)

(III-5)

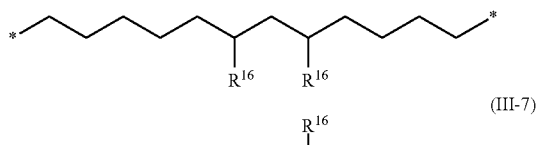

(III-6)

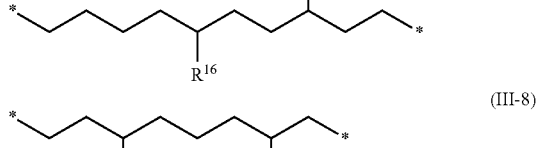

(III-7)

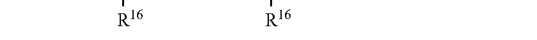

(III-8)

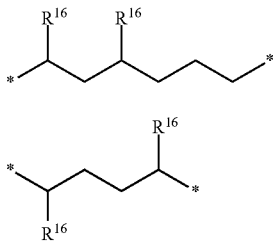

(III-9)

(III-10)

$X^1$ and $X^2$ are independently of each other selected from the group consisting of O, S and N—$R^{17}$, with $R^{17}$ as defined herein.

Preferably $X^1$ is O.

Preferably $X^2$ is O or S.

$X^3$ is O or S.

$R^{17}$ is at each occurrence independently selected from the group consisting of H, alkyl having from 1 to 20 carbon atoms, partially or completely halogenated alkyl having from 1 to 20 carbon atoms and aryl. Preferably $R^{17}$ is H.

Preferably, the compound of formula (I) is an olefinic compound, wherein $R^6$ comprises an olefinically unsaturated group. Preferably $R^6$ is a group of formula (IV-A)

(IV-A)

wherein $X^4$, c, $R_{20}$, $R^{21}$ and $R^{22}$ are as defined herein.

More preferably said olefinic compound comprises a group of formula (IV-A')

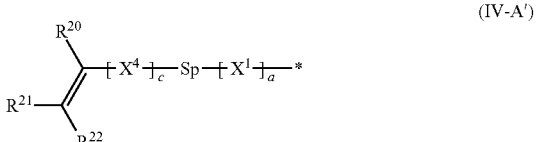

(IV-A')

wherein $X^1$, a, Sp, $X^4$, c, $R^{20}$, $R^{21}$ and $R^{22}$ are as defined herein.

Preferred examples of such olefinic compounds may be represented by any one selected from the group consisting of formulae (I-A'), (I-A"-1), (I-A"-2), (I-A'''1) and (I-A'''-2)

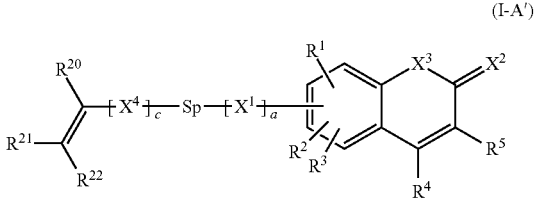

(I-A')

-continued

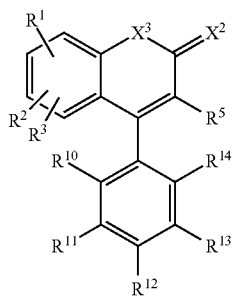
(I-A″-1)

wherein one of $R^{10}$, $R^{11}$, $R^{12}$, $R^{12}$, $R^{13}$ and $R^{14}$ is a group of formula $R^6$-Sp-$[X^1]_a$-* and $R^6$ is a group of formula (IV-A) as defined herein;

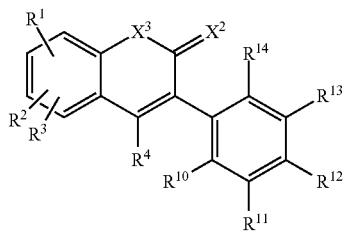
(I-A″-2)

wherein one of $R^{10}$, $R^{11}$, $R^{12}$, $R^{12}$, $R^{13}$ and $R^{14}$ is a group of formula $R^6$-Sp-$[X^1]_a$-* and $R^6$ is a group of formula (IV-A) as defined herein;

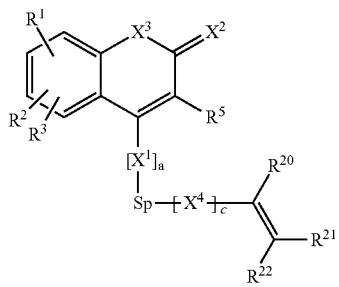
(I-A‴-1)

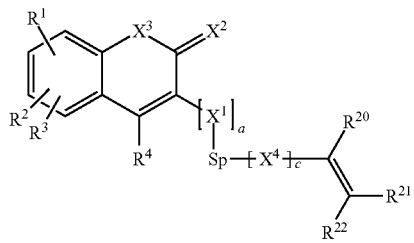
(I-A‴-2)

wherein $R^1$, $R^2$, $R^3$, $R^4$, $R^5$, $X^1$, $X^2$, $X^3$, $X^4$, a, c, $R^{20}$, $R^{21}$ and $R^{22}$ are as defined herein. c is 0 or 1.

$R^{20}$, $R^{21}$ and $R^{22}$ are carbyl. Preferably $R^{20}$, $R^{21}$ and $R^{22}$ are at each occurrence 35 independently of each other selected from the group consisting of H, F, alkyl having from 1 to 20 carbon atoms, partially or completely halogenated alkyl having from 1 to 20 carbon atoms, aryl and heteroaryl. More preferably $R^{20}$, $R^{21}$ and $R^{22}$ are at each occurrence independently of each other selected from the group consisting of H, F, alkyl having from 1 to 20 carbon atoms, partially or completely halogenated alkyl having from 1 to 20 carbon atoms and aryl.

$X^4$ is selected from the group consisting of O, S, C(=O), C(=O)O and N—$R^{17}$, with $R^{17}$ as defined herein. Preferably $X^4$ is O.

It is noted that C(=O)O may be inserted in any direction, i.e. C(=O)O with the —O— group adjacent to Sp or OC(=O) with the —O— group adjacent to the olefinically unsaturated group.

The compounds of the present application may be synthesized by methods well known to the skilled person. An exemplary reaction sequence is shown in Scheme 1.

Scheme 1

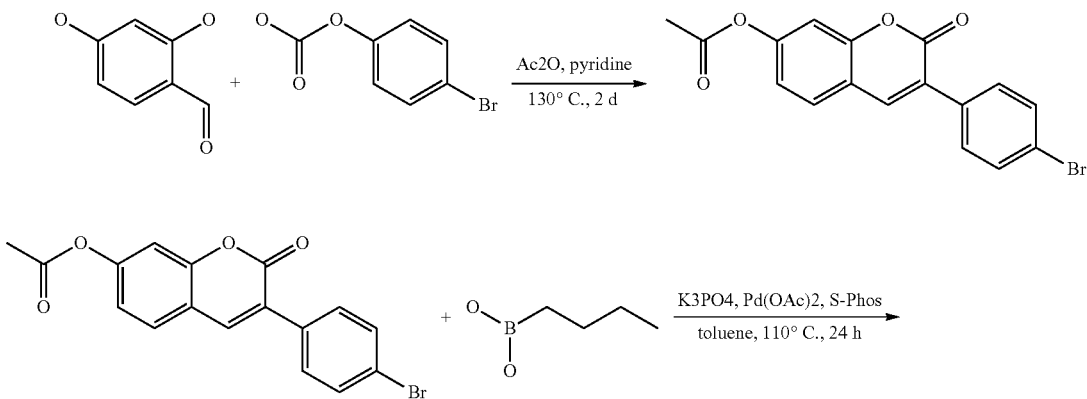

-continued
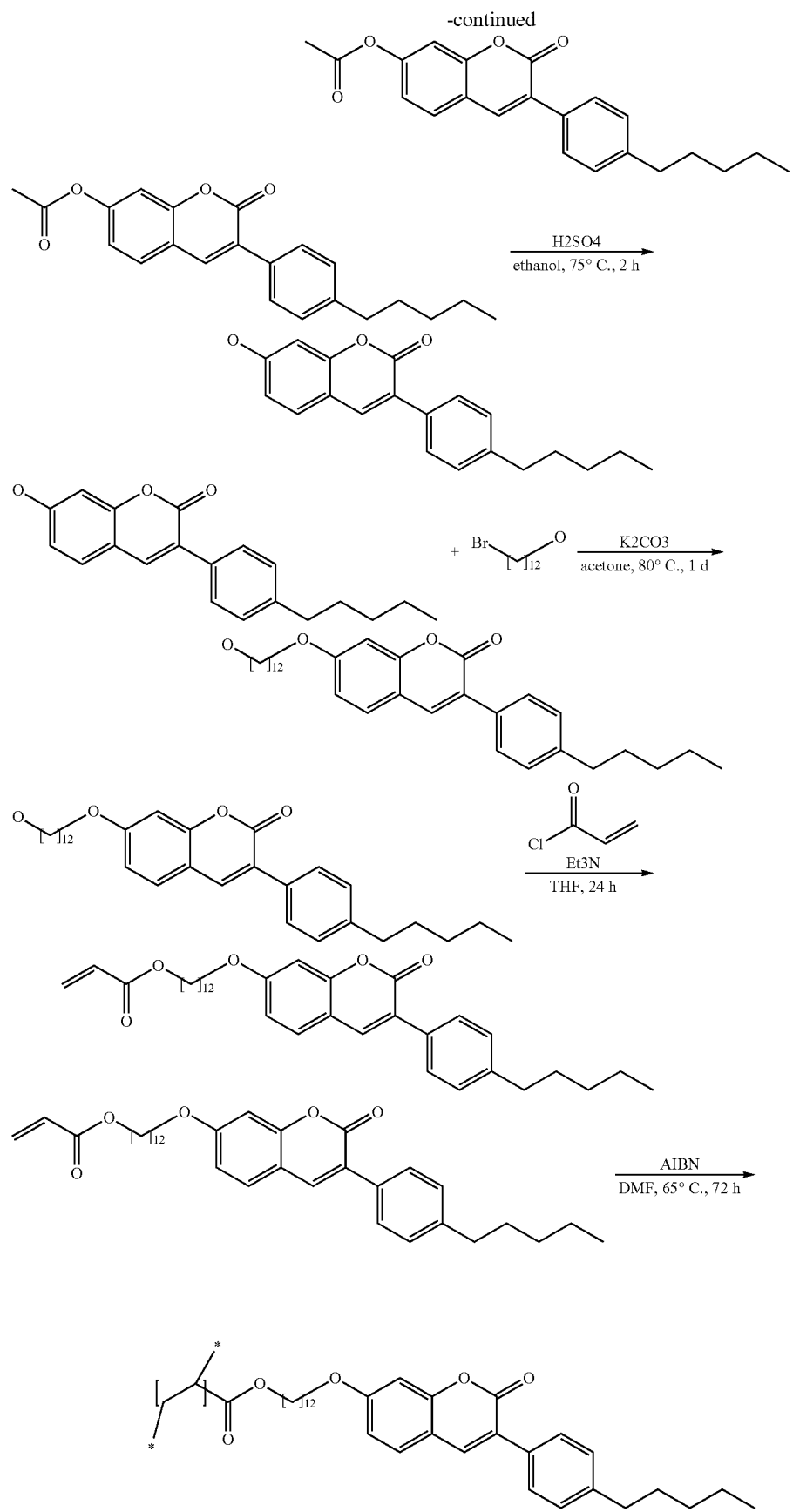

Preferably the compound of the present application is an oligomer or polymer, wherein $R^6$ is the polymer backbone or wherein $R^6$ is part of the polymer backbone. Preferably, such oligomer or polymer comprises a constitutional unit M° of formula (IV-B), i.e. $R^6$ is a group of formula (IV-B)

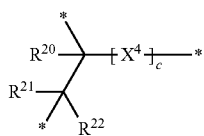

(IV-B)

wherein $X^4$, c, $R^{20}$, $R^{21}$ and $R^{22}$ are as defined herein. More preferably, such oligomer or polymer comprises a constitutional unit M° of formula (IV-B')

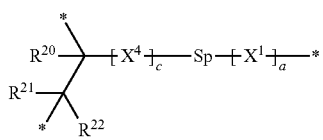

(IV-B')

Preferably, such oligomer or polymer comprises at least one constitutional unit $M^1$ selected from the group consisting of the following formulae (I-B'), (I-B''-1), (I-B''-2), I-B'''-1) and (I-B'''-2)

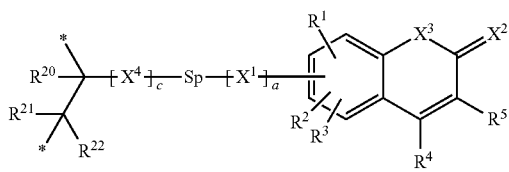

(I-B')

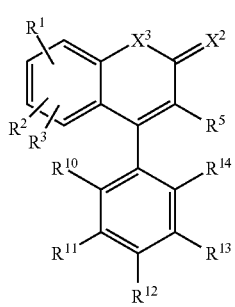

(I-B''-1)

wherein one of $R^{10}$, $R^{11}$, $R^{12}$, $R^{12}$, $R^{13}$ and $R^{14}$ is a group of formula $R^6$-Sp-$[X^1]_a$-* and $R^6$ is a group of formula (IV-B) as defined herein;

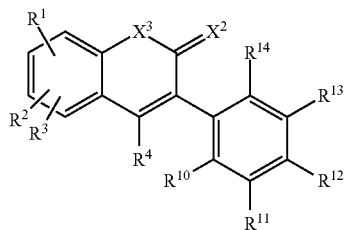

(I-B''-2)

wherein one of $R^{10}$, $R^{11}$, $R^{12}$, $R^{12}$, $R^{13}$ and $R^{14}$ is a group of formula $R^6$-Sp-$[X^1]_a$-* and $R^6$ is a group of formula (IV-B) as defined herein;

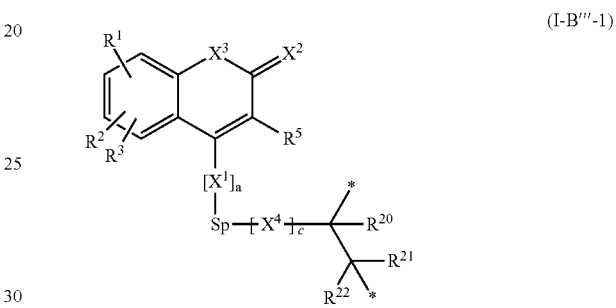

(I-B'''-1)

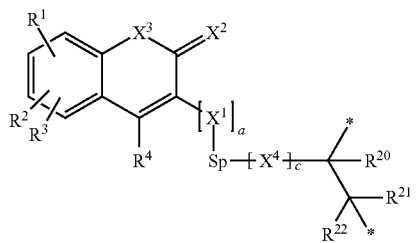

(1-B'''-2)

said at least one unit $M^1$ being—if there are two or more, at each occurrence the same or different, wherein $R^1$, $R^2$, $R^3$, $R^4$, $R^5$, $X^1$, $X^2$, $X^3$, $X^4$, a, c, $R^{20}$, $R^{21}$ and $R^{22}$ are as defined herein.

The compound of formula (I) may be a copolymer, i.e. an oligomer or polymer comprising one or more constitutional unit $M^1$ of formula (I-B), which may be the same or different from one another, and one or more constitutional units $M^2$, which may the same or different from one another. Said one or more constitutional units $M^2$ are chemically different from the units $M^1$. Preferably, said one or more constitutional units $M^2$ are derived by polymerization of one or more monomers selected from the group consisting of ethylene, propylene, acrylate, methacrylate and styrene.

Preferably the compound of formula (I) may be a homopolymer, i.e. an oligomer or polymer comprising one or more constitutional unit $M^1$ of formula (I-B), wherein all constitutional units $M^1$ are the same.

Exemplary compounds of formula (I) may be selected from the following formulae (M-1) to (M-63):
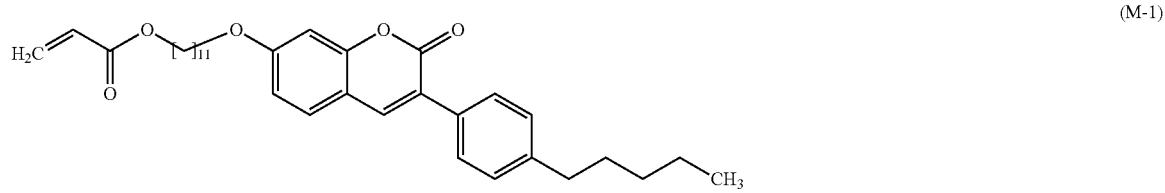
(M-1)
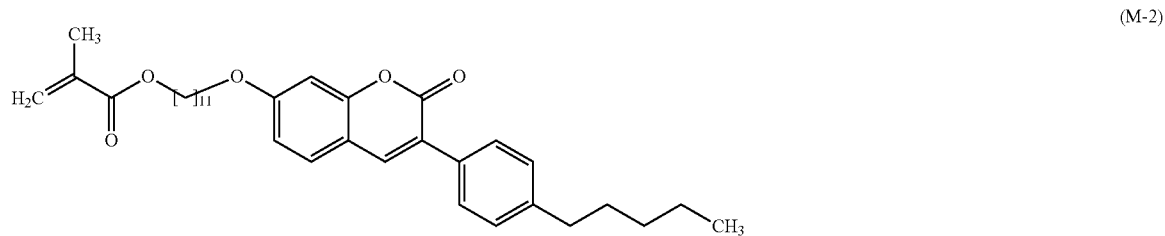
(M-2)
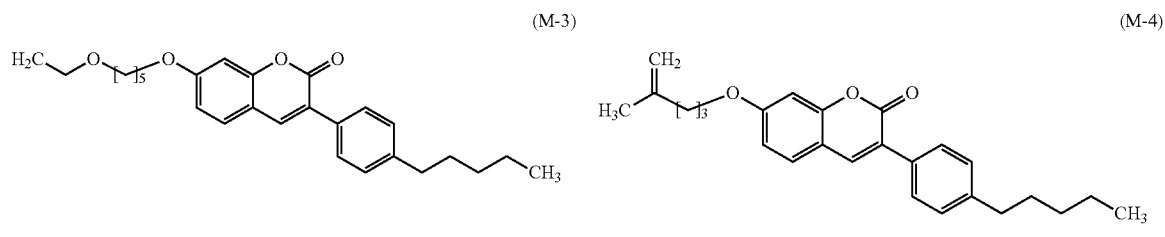
(M-3) (M-4)
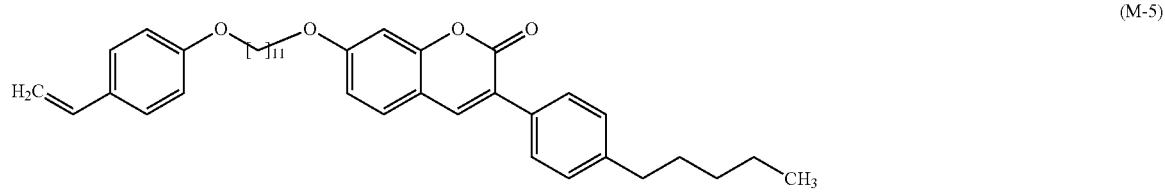
(M-5)
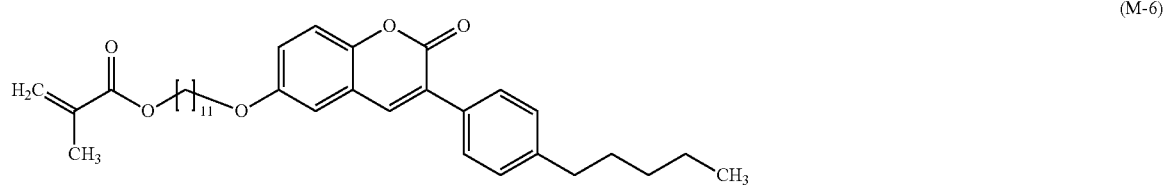
(M-6)
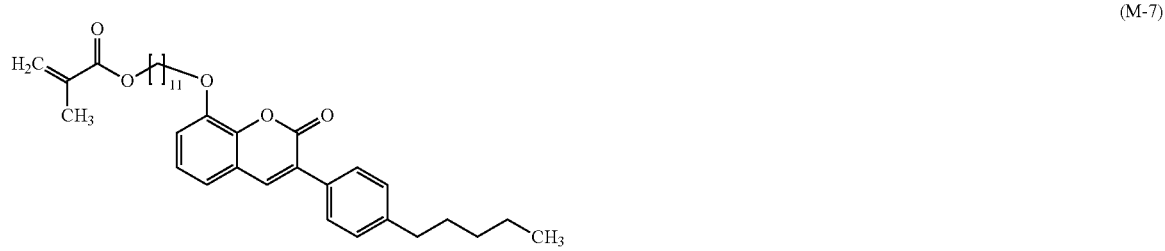
(M-7)
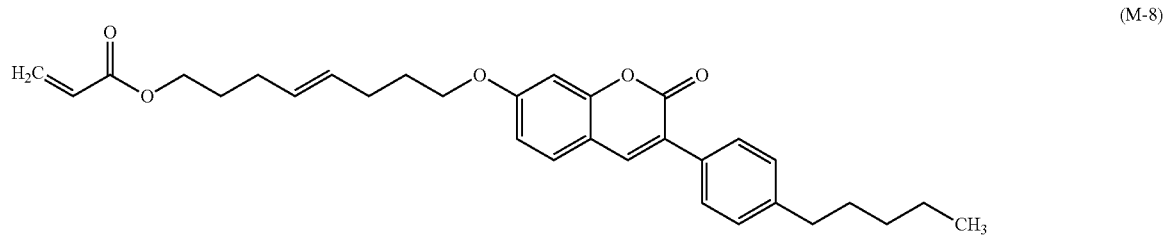
(M-8)

-continued
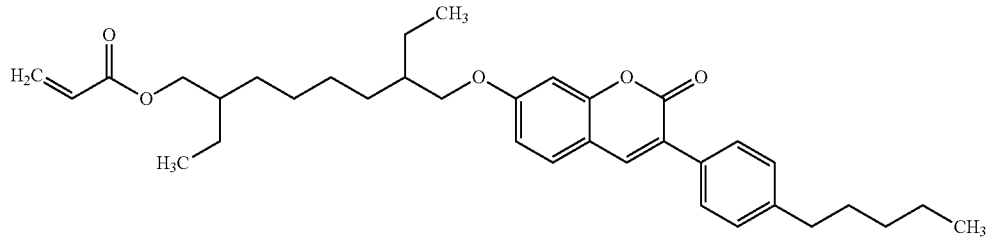
(M-9)
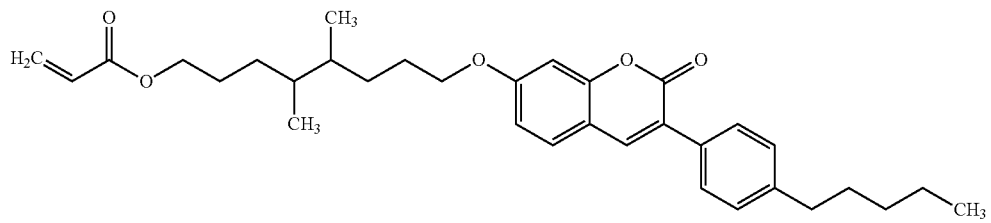
(M-10)
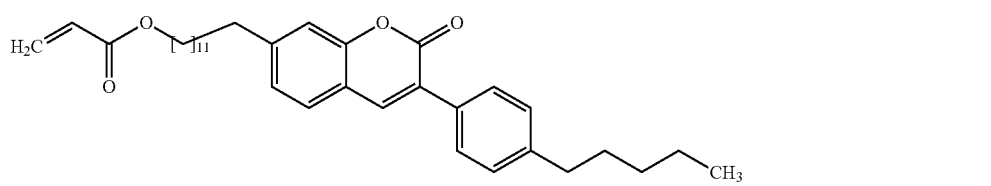
(M-11)
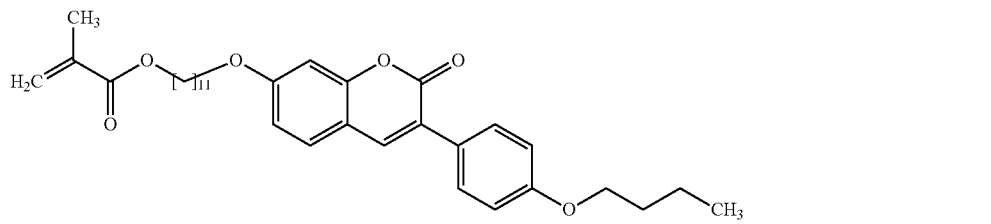
(M-12)
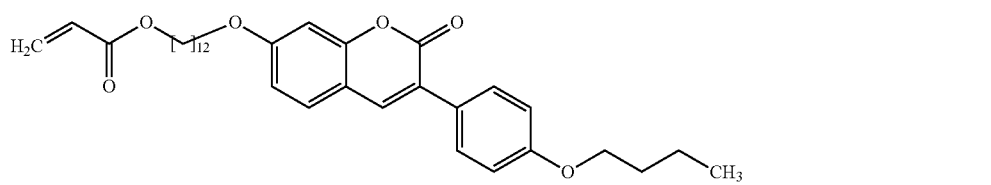
(M-13)
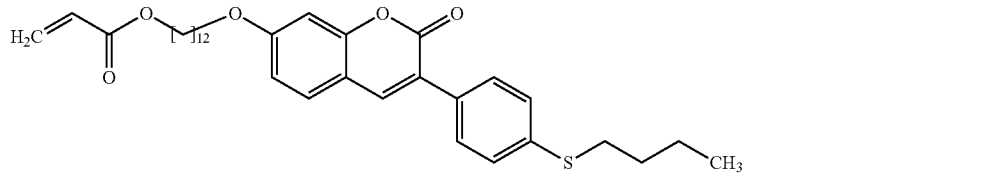
(M-14)
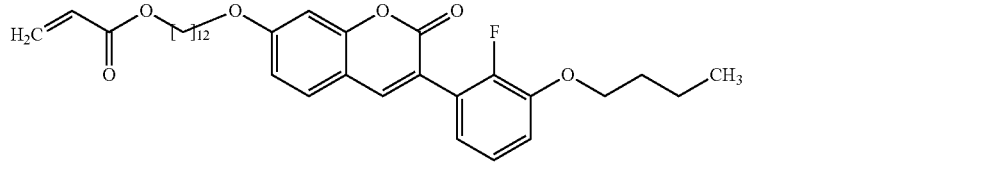
(M-15)
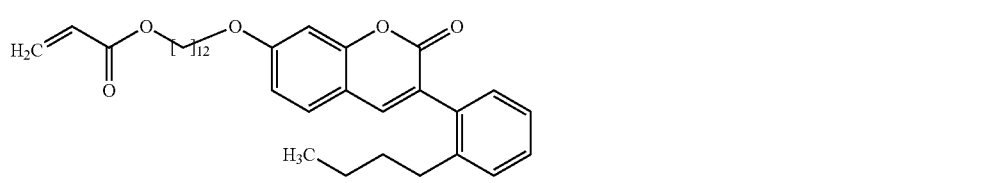
(M-16)

-continued
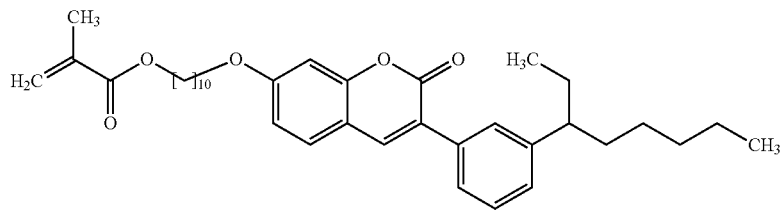
(M-17)
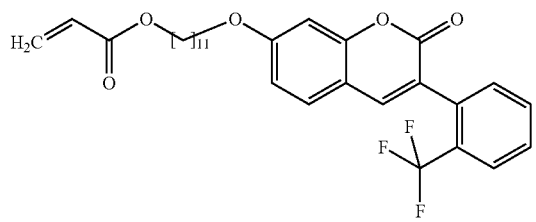
(M-18)
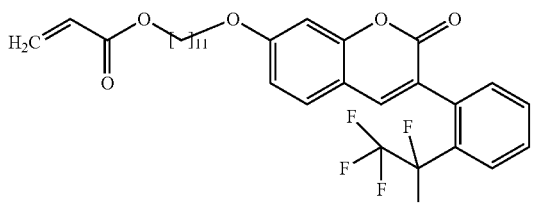
(M-19)
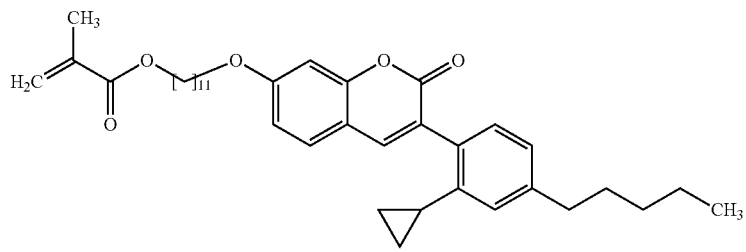
(M-20)
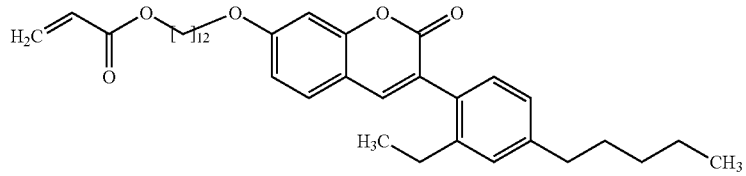
(M-21)
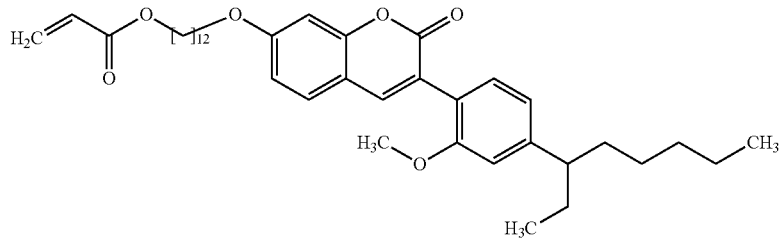
(M-22)
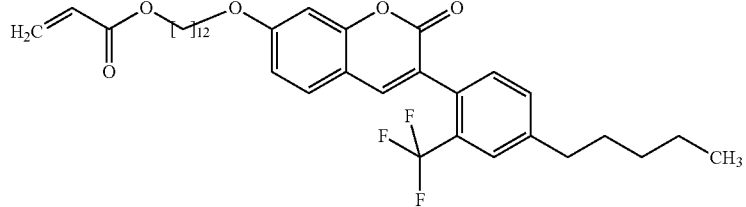
(M-23)
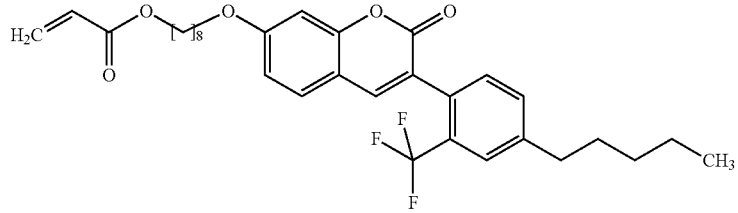
(M-24)

-continued
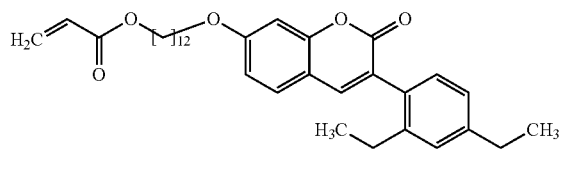
(M-25)
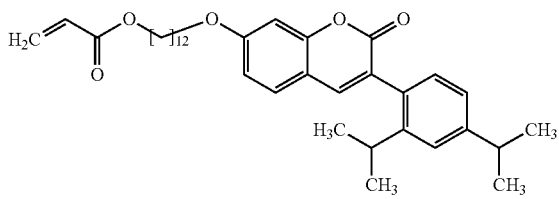
(M-26)
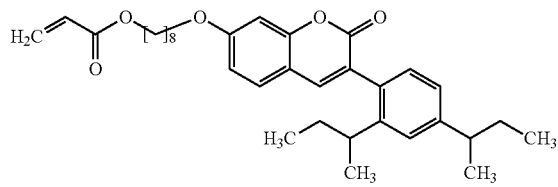
(M-27)
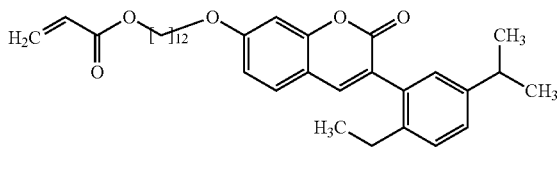
(M-28)
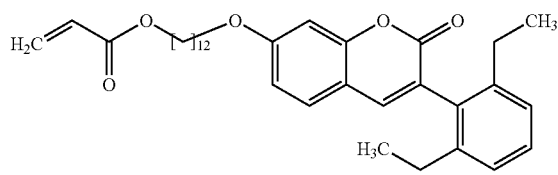
(M-29)
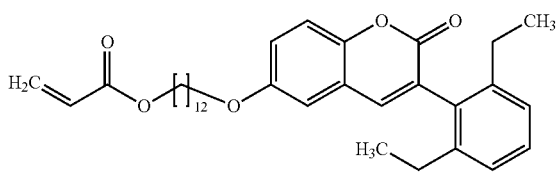
(M-30)
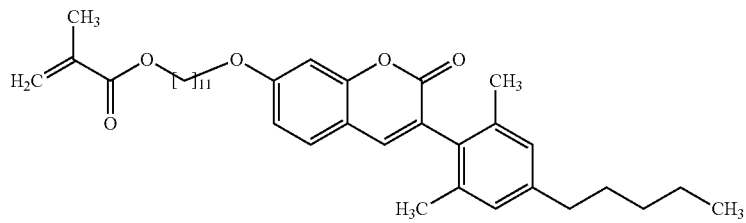
(M-31)
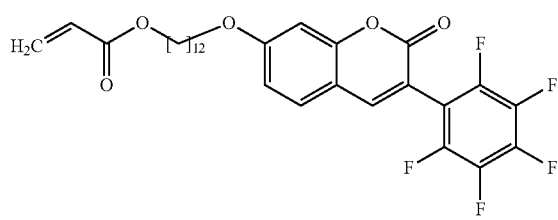
(M-32)
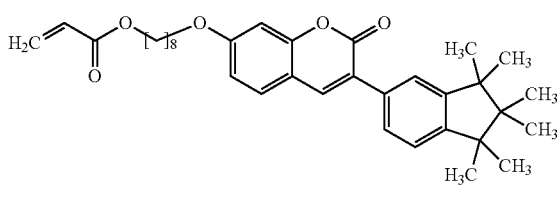
(M-33)
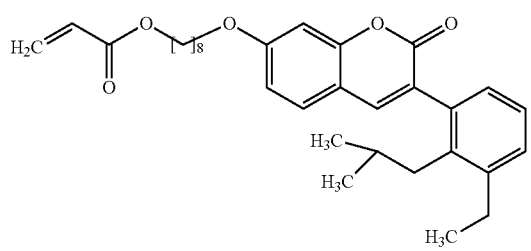
(M-34)
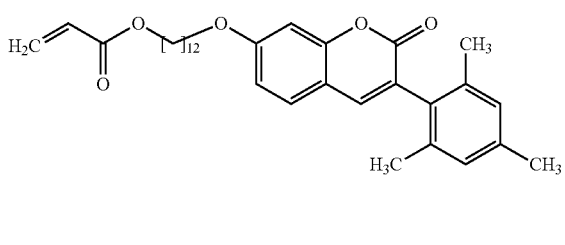
(M-35)
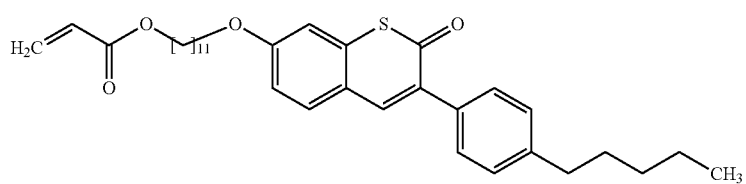
(M-36)

-continued
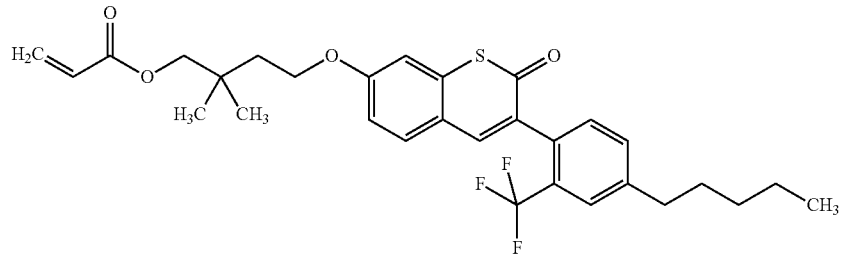
(M-37)
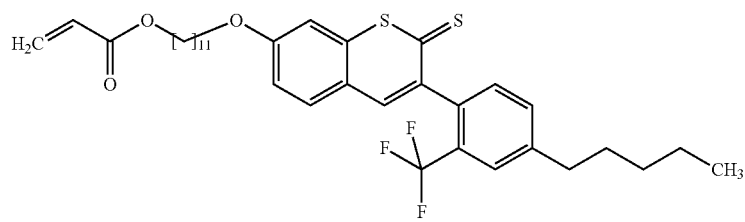
(M-38)
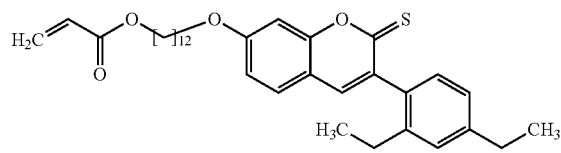
(M-39)
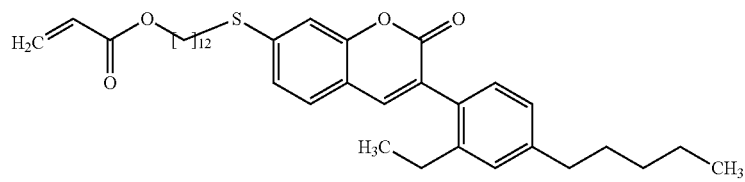
(M-40)
(M-41)
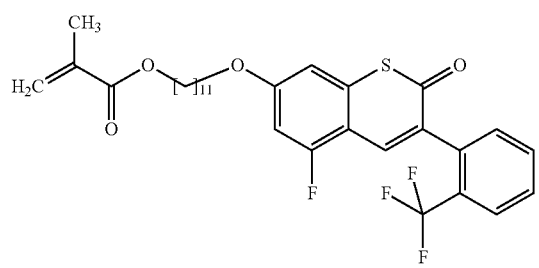
(M-42)
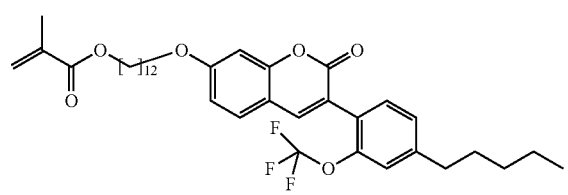
(M-43)
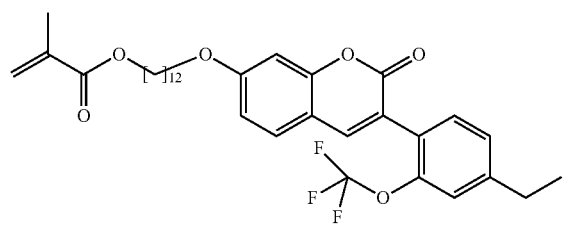
(M-44)
(M-45)
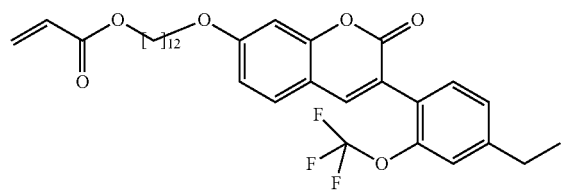
(M-46)
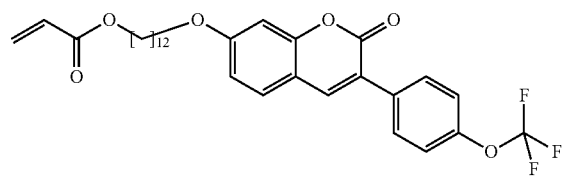

-continued
(M-47)
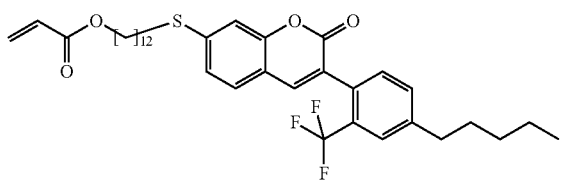
(M-48)
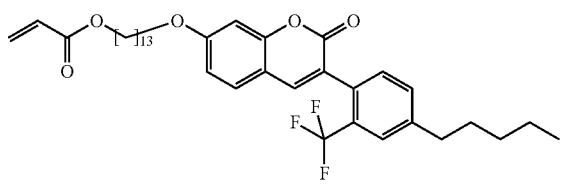
(M-49)
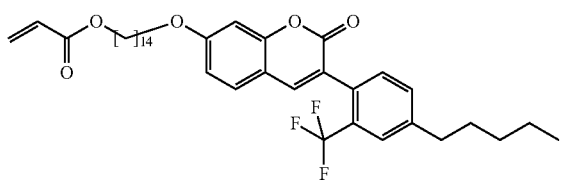
(M-50)
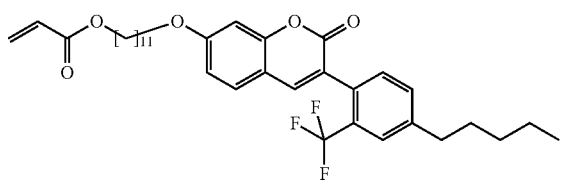
(M-51)
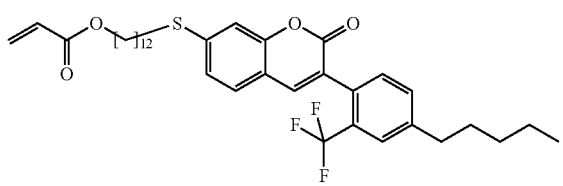
(M-52)
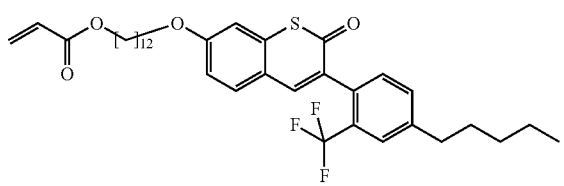
(M-53)
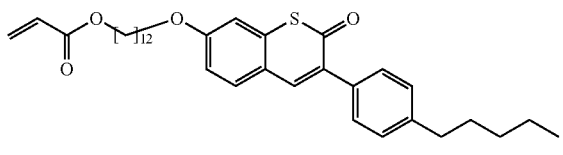
(M-54)
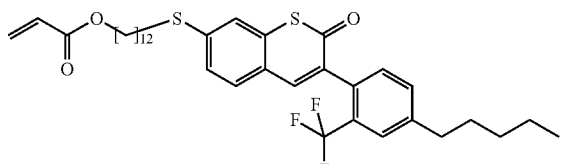
(M-55)
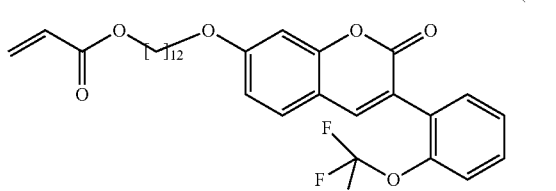
(M-56)
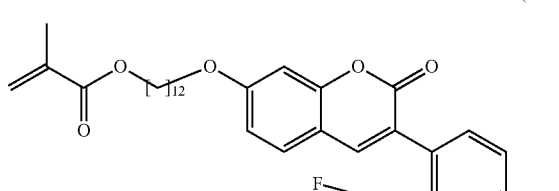
(M-57)
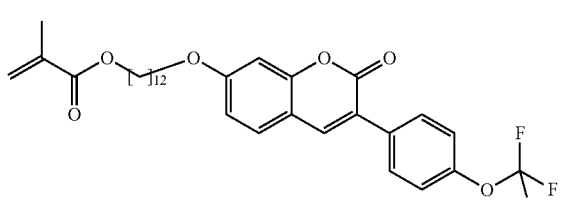
(M-58)
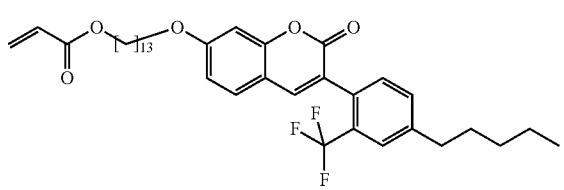
(M-59)
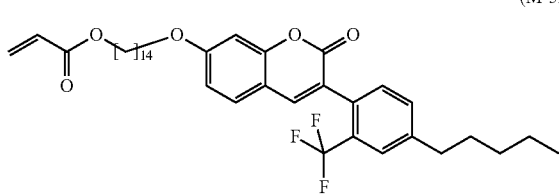
(M-60)
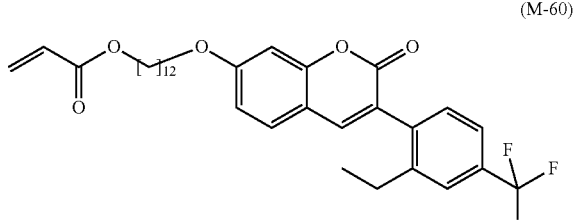

(M-61)
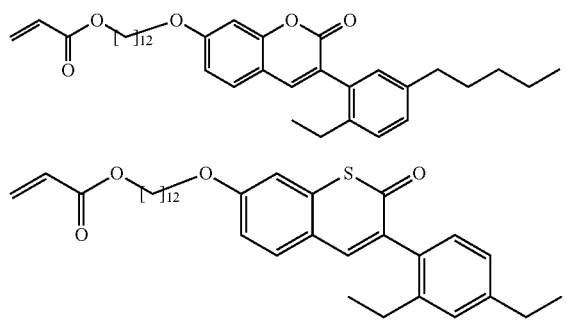
(M-62)
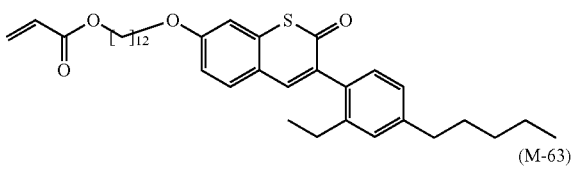
(M-63)
Exemplary oligomeric and polymeric compounds of formula (I) may be selected from the following formulae (P-1) to (P-63):
(P-1)
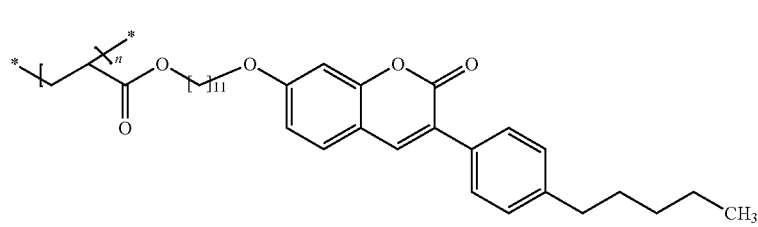
(P-2)
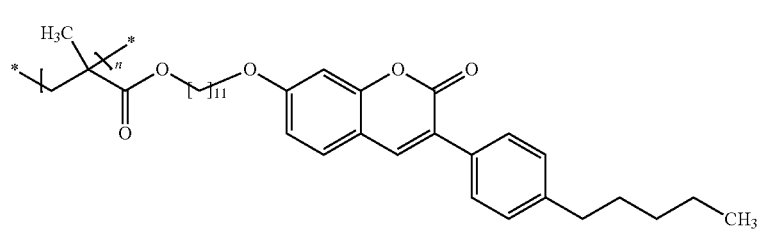
(P-3)
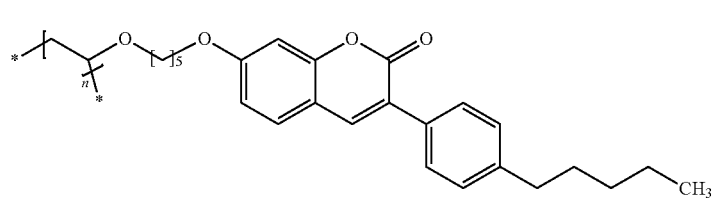
(P-4)
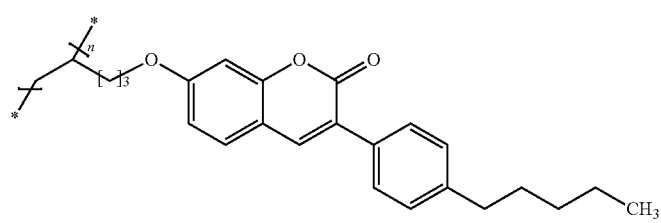
(P-5)
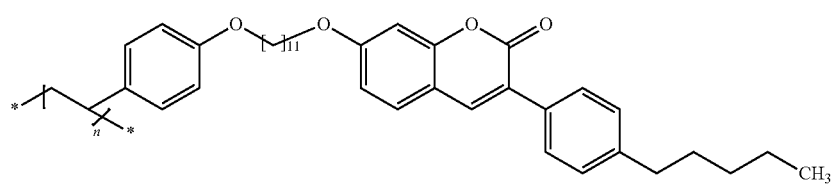

-continued
(P-6)
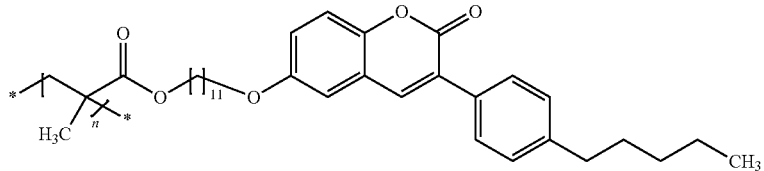
(P-7)
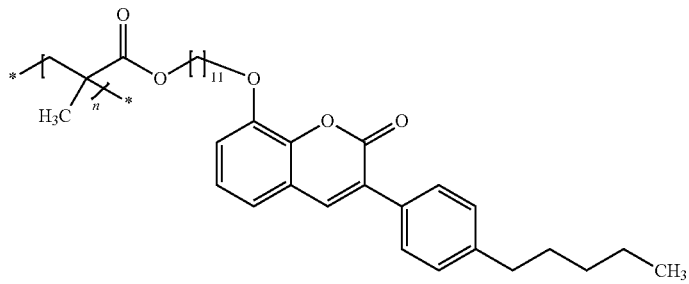
(P-8)
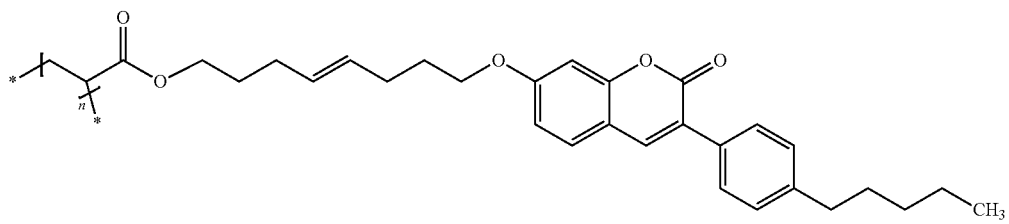
(P-9)
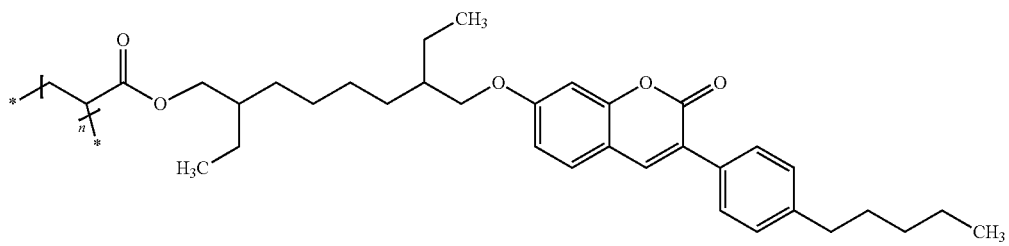
(P-10)
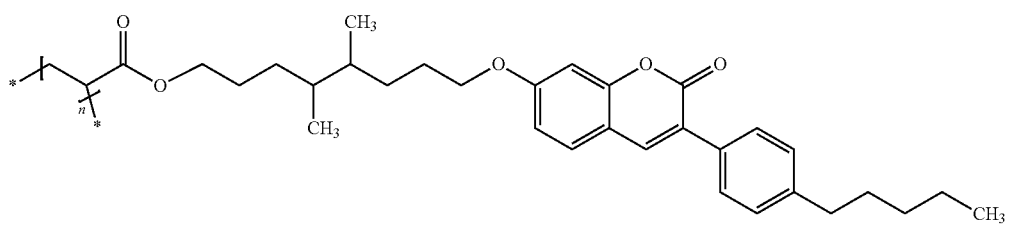
(P-11)
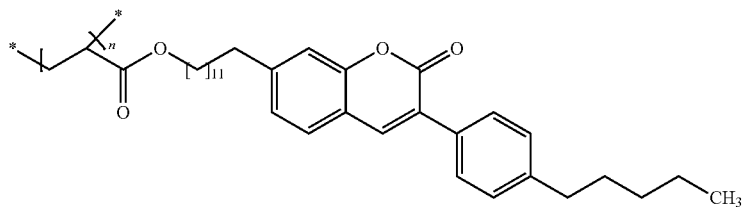
(P-12)
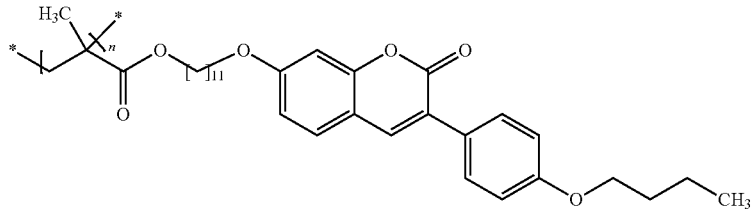

-continued
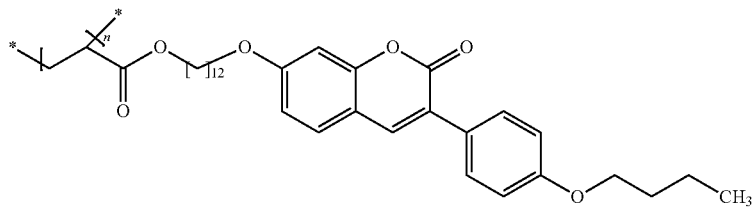
(P-13)
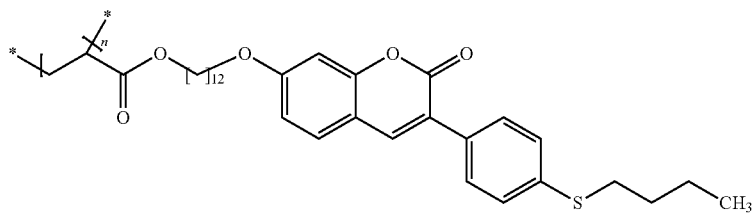
(P-14)
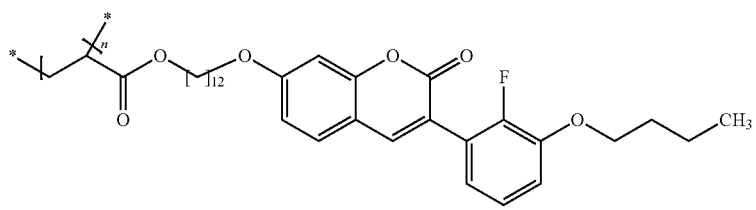
(P-15)
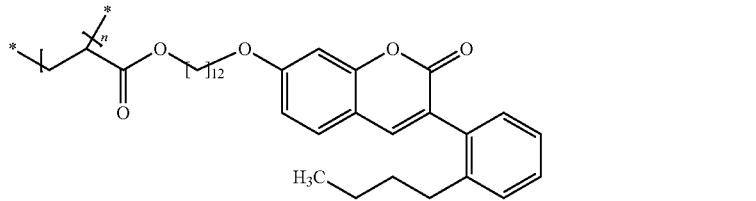
(P-16)
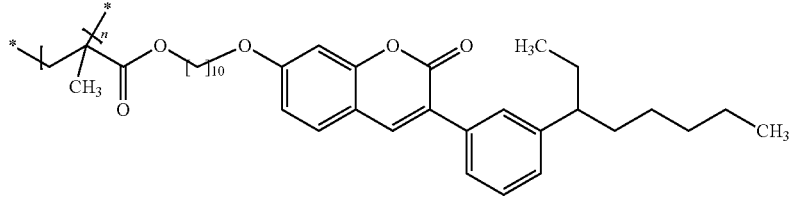
(P-17)
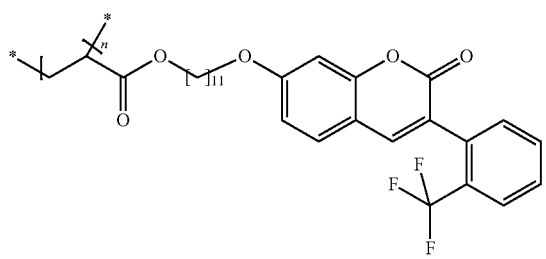
(P-18)
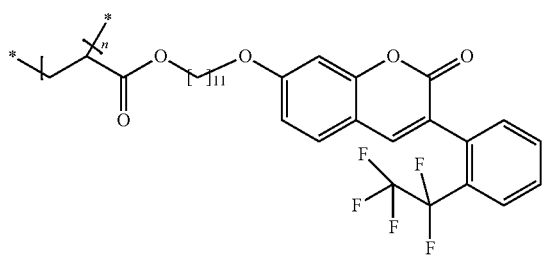
(P-19)
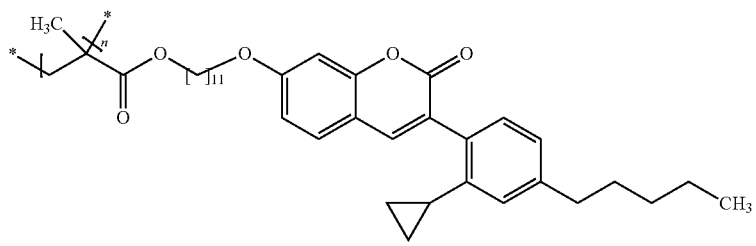
(P-20)

-continued
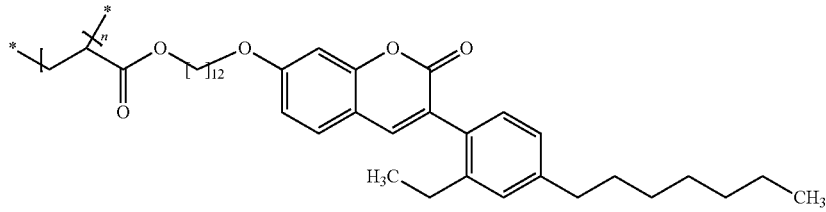
(P-21)
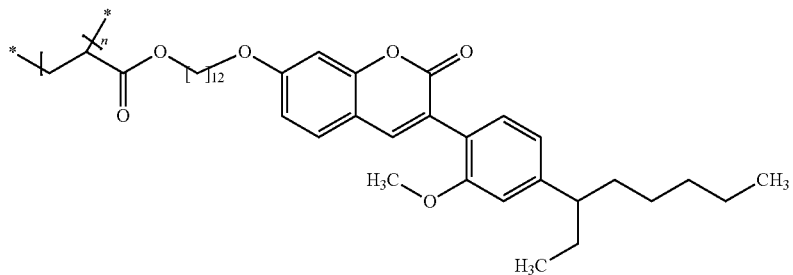
(P-22)
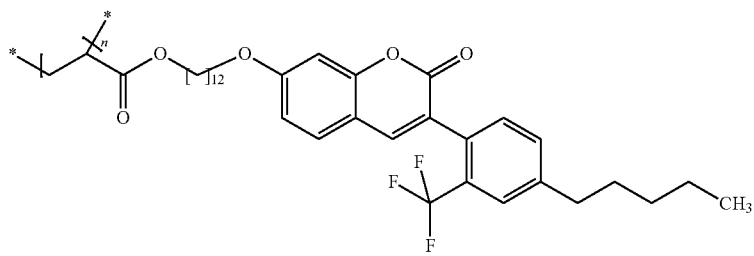
(P-23)
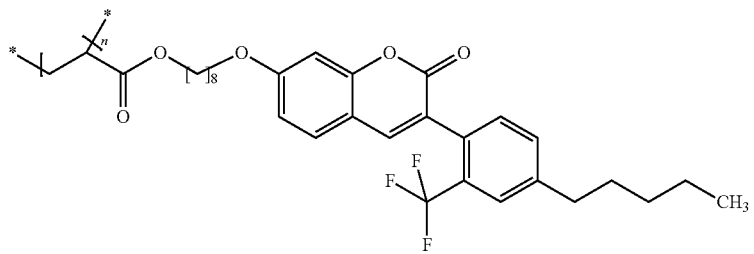
(P-24)
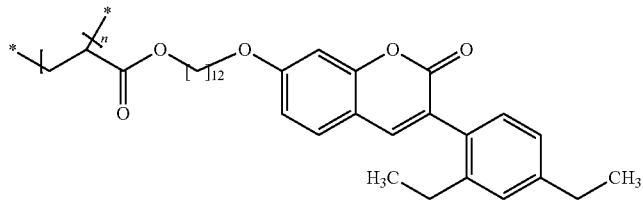
(P-25)
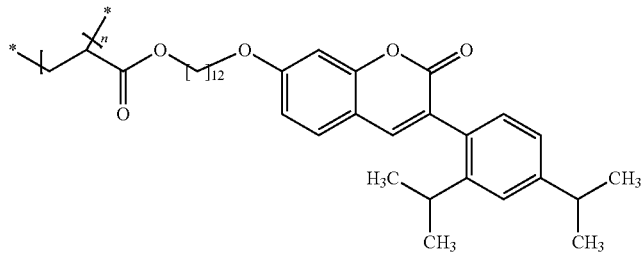
(P-26)

-continued
(P-27)
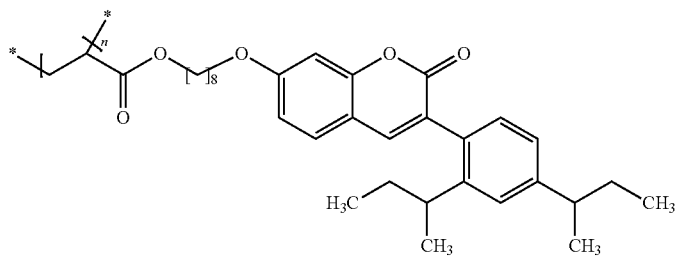
(P-28)
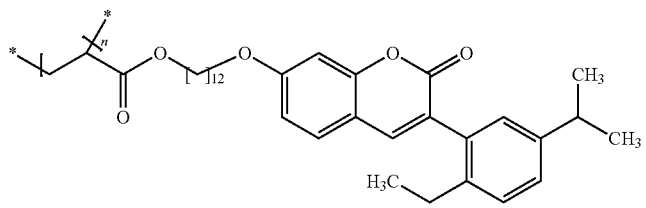
(P-29)
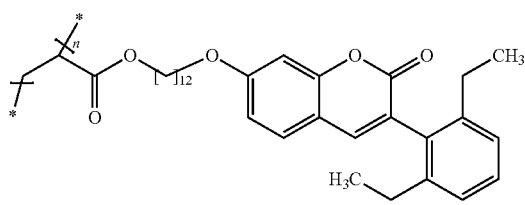
(P-30)
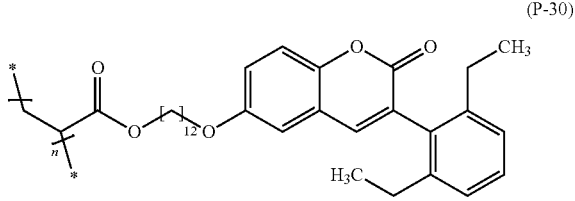
(P-31)
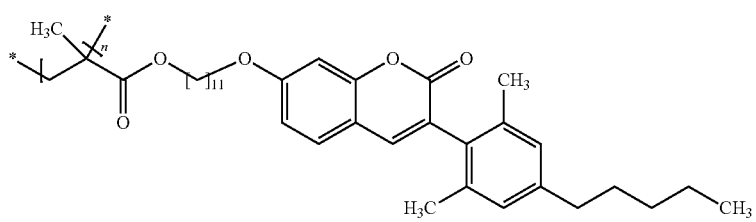
(P-32)
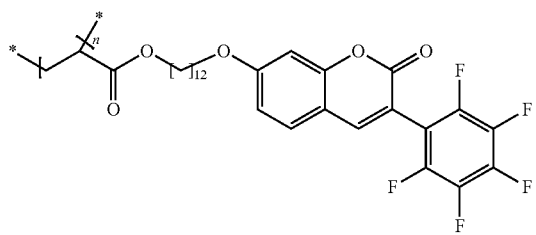
(P-33)
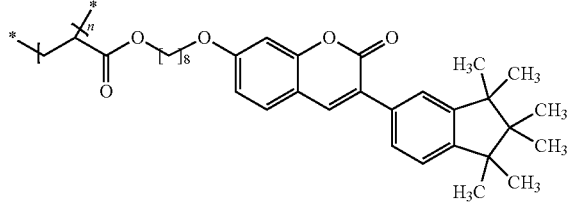
(P-34)
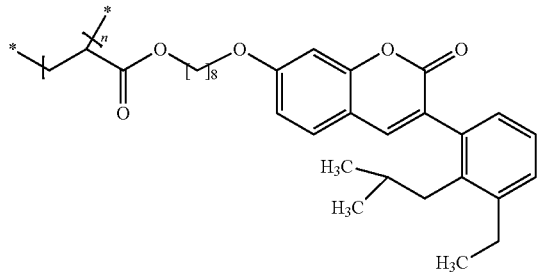
(P-35)
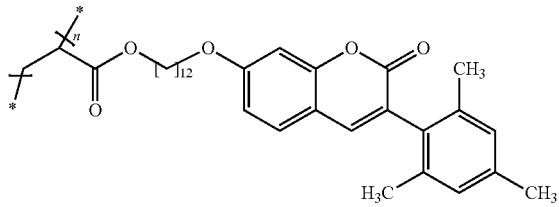

(P-36)
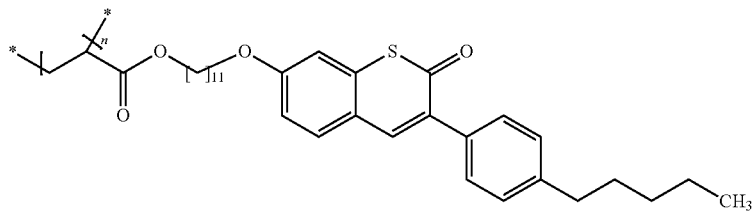
(P-37)
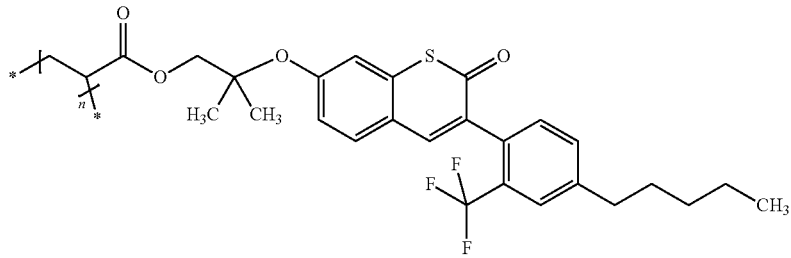
(P-38)
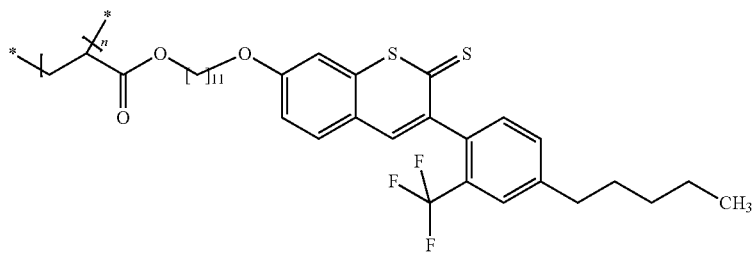
(P-39)
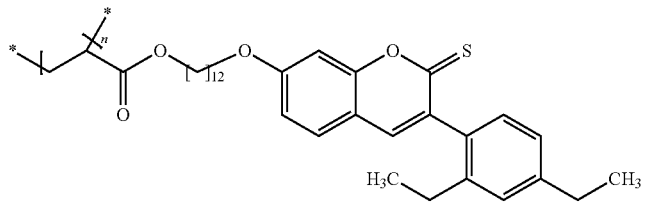
(P-40)
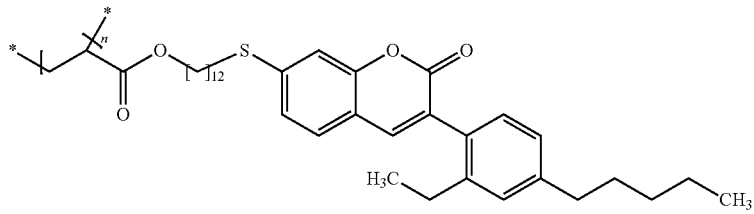
(P-41)
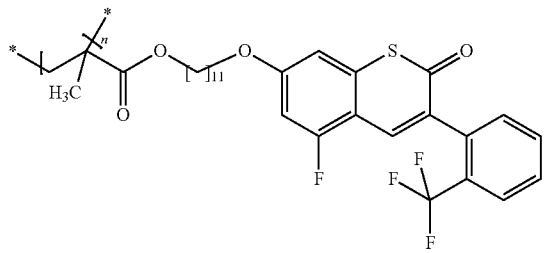

-continued
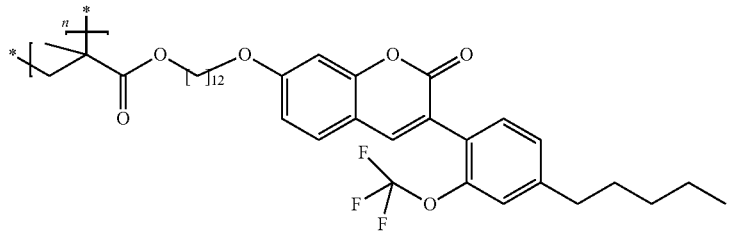
(P-42)
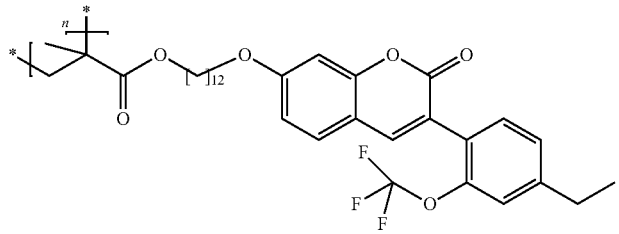
(P-43)
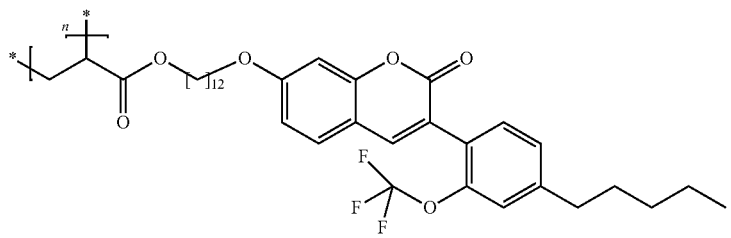
(P-44)
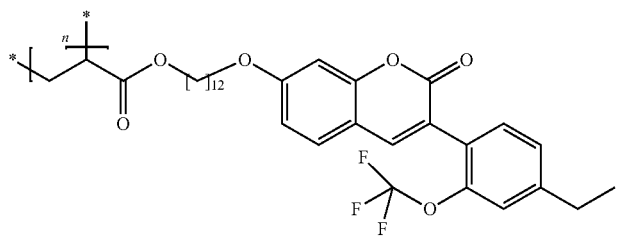
(P-45)
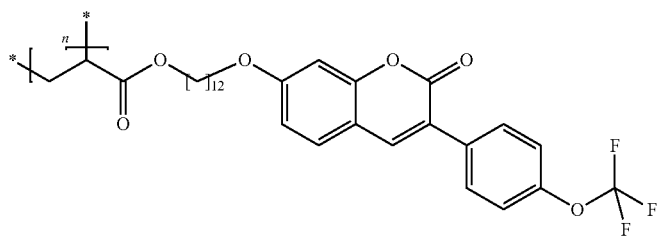
(P-46)
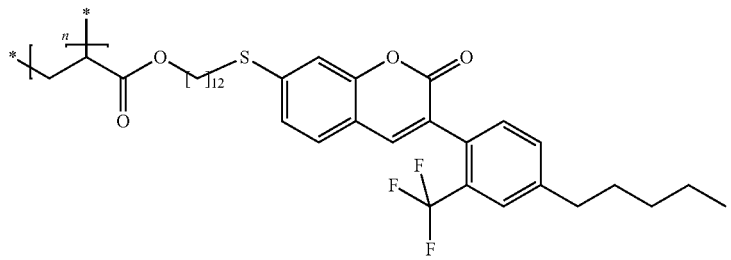
(P-47)

-continued
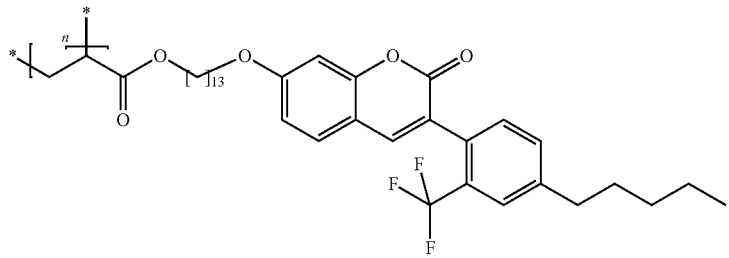
(P-48)
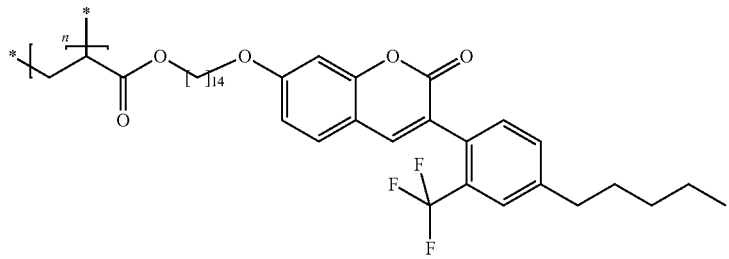
(P-49)
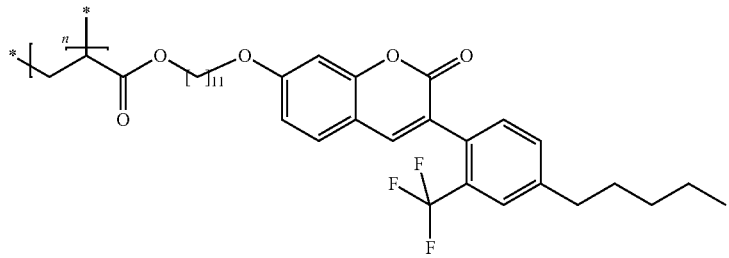
(P-50)
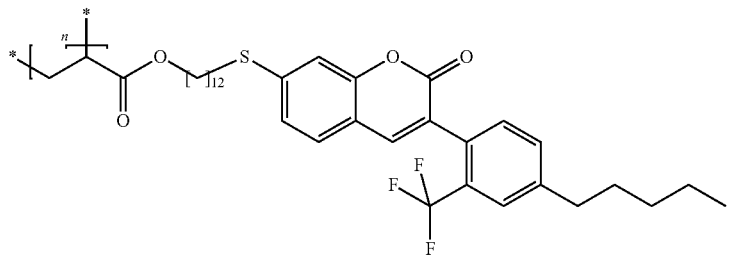
(P-51)
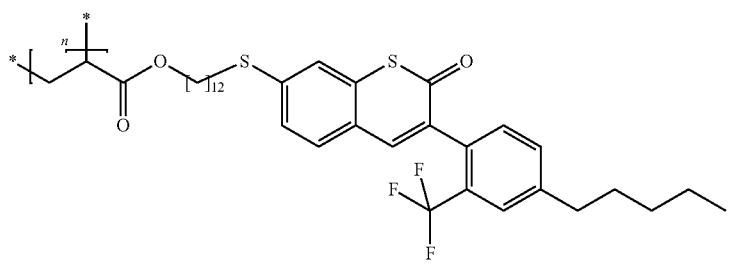
(P-52)
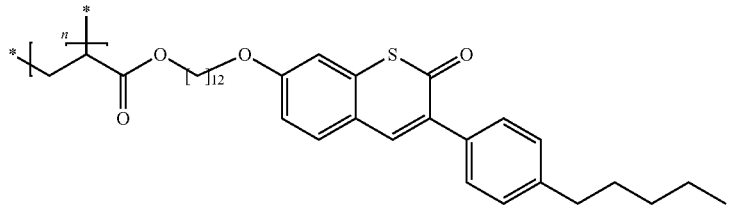
(P-53)

-continued
(P-54)
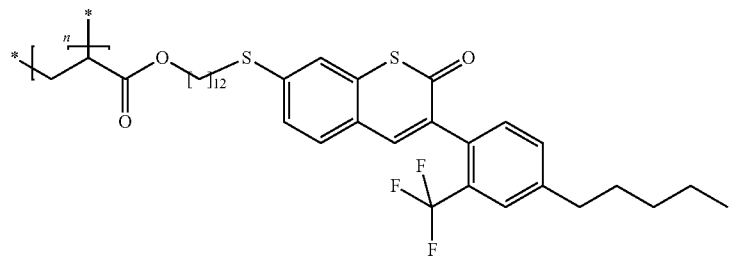
(P-55)
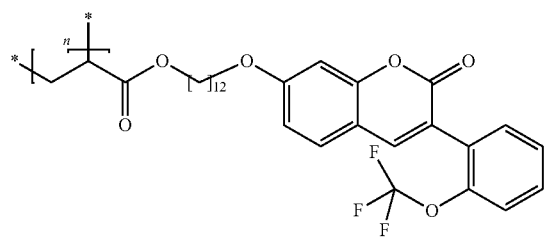
(P-56)
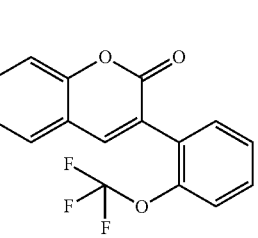
(P-57)
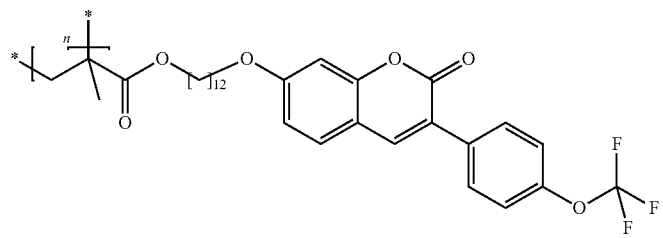
(P-58)
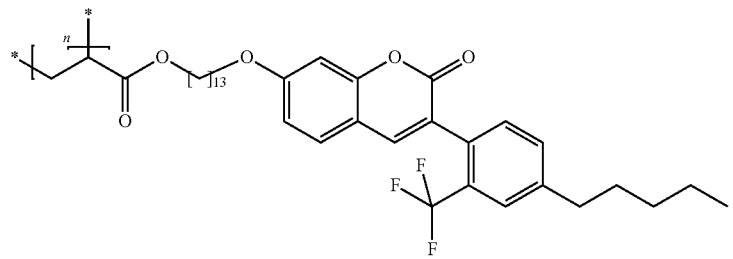
(P-59)
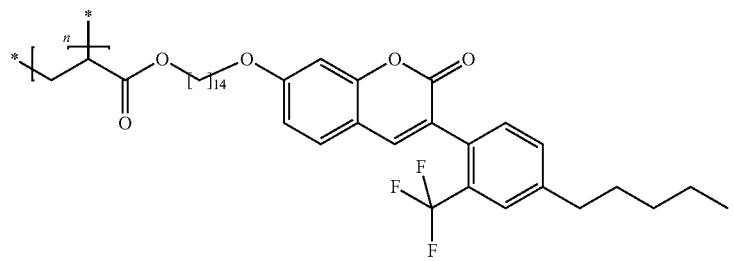
(P-60)
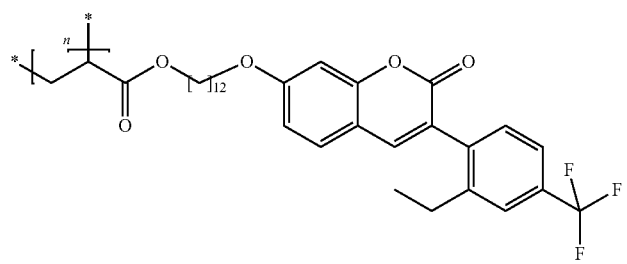

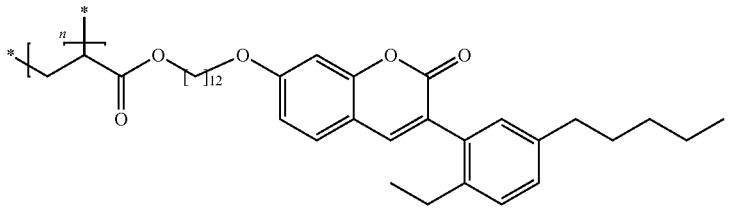

(P-61)

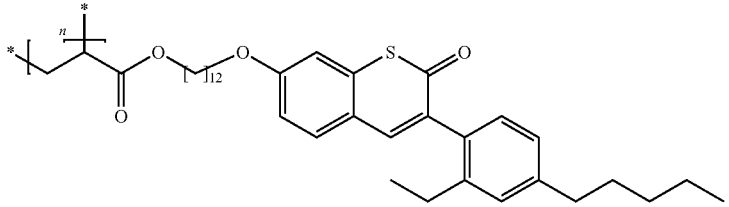

(P-62)

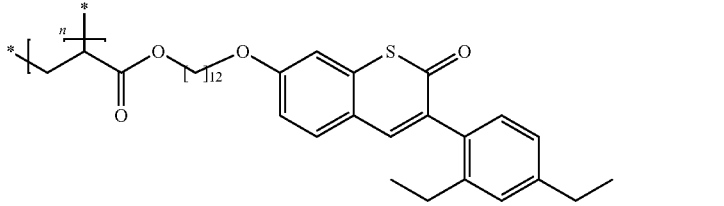

(P-63)

For the purposes of the present application the term "derived by polymerization" is used to indicate that a double bond is formally turned into a single bond and two linkages to other atoms, said linkages being indicated by the two asterisks:

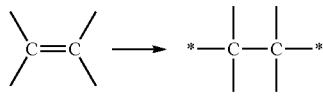

Preferably said copolymer comprises the one or more constitutional units $M^1$ in a molar ratio $m_1$ and the one or more constitutional units $M^2$ in a molar ratio mz, wherein the ratio $m_1:m_2$ is at least 0.01 and at most 100.

The present oligomers and polymers may be made by any suitable method. It is, however, preferred that the present oligomers and polymers are made by radical polymerization, wherein the polymerization reaction is started by means of a suitable radical polymerization initiator. For the purposes of the present application the type of radical polymerization initiator is not particularly limited and may be any suitable radical generating compound. Such compounds are well known to the skilled person. Suitable polymerization initiators may be selected from thermal initiators or photoinitiators, i.e. compounds that generate radicals by exposure to heat or irradiation with light of a suitable wavelength. Examples of suitable thermal polymerization initiators may be selected from the groups of compounds comprising one or more peroxide groups, i.e. compounds comprising a group —O—O—, and/or compounds comprising one or more azo groups, i.e. compounds comprising a group —N=N—.

Suitable polymerization initiators comprising one or more peroxide groups may, for example, be selected from the groups consisting of t-butyl(peroxy-2-ethyl-hexanoate), di-(tert-butylcyclohexyl)peroxydicarbonate and benzoylperoxide.

Suitable polymerization initiators comprising one or more azo groups may, for example, be selected from the group consisting of 1,1'-azobis(cyclohexancarbonitrile and 2,2'azobis(cyclohexanecarbonitrile) (AIBN).

A suitable example of a photoinitiator is dimethylaminobenzoate/champherchinone

If a photoinitiator is used as polymerization initiator, it is preferred that the wavelength required to decompose said photoinitiator is different from the wavelength needed to irradiate the compound of the present application so as to change its optical properties.

Preferably, the radical initiators are used in an amount of at least 0.0001 eq and of at most 0.1 eq of the main monomer. Such radical initiators could be thermal initiators, e.g. azobisisobutyronitrile (AIBN) or photochemical initiators like dimethylaminobenzoate/champherchinone.

The present application also provides for a composition comprising the compound of formula (I). Depending upon the intended use such composition may comprise further different components. Such further components may, for example, be selected from the group consisting of UV absorbers, antioxidants and crosslinkers.

The UV absorber that may be used in the present composition is not particularly limited and can easily be selected from those generally known to the skilled person. Generally suitable UV absorbers are characterized by being unsaturated compounds, preferably compounds comprising one or more selected from group consisting of olefinic groups, aryl groups and heteroaryl groups; these groups may be present in any combination.

Suitable UV-absorbers for use in the present composition may, for example, be selected from those comprising a group selected from benzotriazole, benzophenone and triazine. Suitable UV-absorbers are, for example, disclosed in U.S. Pat. Nos. 5,290,892; 5,331,073 and 5,693,095.

Suitable crosslinkers may be used to impart elastomeric properties to the present composition and the articles produced therewith. Typically any suitable di- or tri-functional monomer may be used as crosslinker. Such monomers are generally well known to the skilled person.

The present compound of formula (I) is particularly well suited for use in optically active devices. Hence the present application also provides for optically active devices comprising the compound of formula (I). Preferred optically active devices are ophthalmic devices. Examples of such ophthalmic devices include lenses, keratoprostheses, and cornea inlays or rings. More preferably, said optically active device is a lens. Most preferably, such optically active device is an intraocular lens, which may, for example, be a posterior chamber intraocular lens or an anterior chamber intraocular lens.

The present optically active devices may be formed by a process comprising the steps of
 a) providing a composition comprising the compound as defined herein; and
 b) subsequently forming the article of said composition.

Intraocular lenses in accordance with the present application are believed to show particularly advantageous properties in that they are flexible enough so as to be rolled or folded and consequently requiring a much smaller incision for them to be inserted into the eye. It is believed that this will allow for improved healing of the eye, particularly in respect to the time for the eye to heal.

The type of intraocular lens is not limited in any way. It may, for example, comprise one or more optic and one or more haptic components, wherein the one or more optic components serve as lens and the one or more haptic components are attached to the one or more optic components and hold the one or more optic components in place in the eye. The present intraocular lens may be of a one-piece design or of multi-piece design, depending on whether the one or more optic components and the one or more haptic components are formed from a single piece of material (one-piece design) or are made separately and then combined (multi-piece design). The present intraocular lens is also designed in such a way that it allows to be, for example, rolled up or folded small enough so that it fits through an incision in the eye, said incision being as small as possible, for example, at most 3 mm in length.

Additionally, intraocular lenses in accordance with the present application allow for the non-invasive adjustment of the optical properties, particularly the refractive power, after implantation of the lens into the eye, thus reducing the need for post-surgery vision aids or reducing or totally avoiding follow-up surgery.

In order to change the optical properties and particularly the refractive power of the intraocular lens it is exposed to irradiation having a wavelength of at least 200 nm and of at most 1500 nm. Hence, the present application also provides for a process of changing the optical properties of an optically active article as defined herein, said process comprising the steps of a) providing an article as defined herein; and b) subsequently exposing said article to irradiation having a wavelength of at least 200 nm and at most 1500 nm.

Preferably, said irradiation has a wavelength of at least 250 nm or 300 nm, more preferably of at least 350 nm, even more preferably of at least 400 nm, still even more preferably of at least 450 nm, and most preferably of at least 500 nm. Preferably, said irradiation has a wavelength of at most 1400 nm or 1300 nm or 1200 nm or 1100 nm or 1000 nm, more preferably of at most 950 nm or 900 nm, even more preferably of at most 850 nm, still even more preferably of at most 800 nm and most preferably of at most 750 nm.

EXAMPLES

The following examples are intended to show the advantages of the present compounds in a non-limiting way.

Unless indicated otherwise, all syntheses were carried out under an inert atmosphere using dried (i.e. water-free) solvents. Solvents and reagents were purchased from Sigma-Aldrich or ABCR.

DCM is used to denote dichloromethane. DMF is used to denote dimethylformamide. EE is used to denote ethyl acetate. THF is used to denote tetra hydrofura n.

Example 1

Acetic Acid 3-(4-bromo-phenyl)-coumarin-7-yl ester

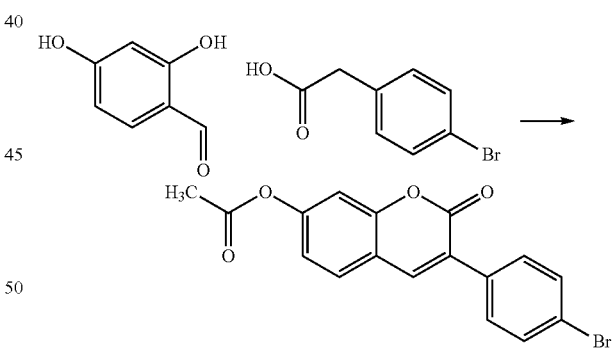

2 g (14.2 mmol) 2,4-Dihydroxy-benzaldehyde and 3.1 g (14.2 mmol) 4-bromophenylacetic acid were dissolved in 4.5 ml acetic anhydride and 4.4 ml pyridine. The batch is stirred at 135° C. for 72 h and is then cooled to room temperature. The solid which has precipitated out is filtered off with suction and rinsed neutral with water. The residue is dried at 40° C. in vacuo. The yield is 4.9 g (13.6 mmol) (96% of theory).

$^1$H NMR (500 MHz, DMSO-d$_6$) δ 6 8.31 (s, 1H), 7.82 (d, J=8.4 Hz, 1H), 7.72-7.62 (m, 4H), 7.32 (d, J=2.1 Hz, 1H), 7.20 (dd, J=8.5, 2.2 Hz, 1H), 2.32 (s, 3H).

The following compounds 1a to 1q are prepared analogously:

| | Reactant 1 | Reactant 2 |
|---|---|---|
| 1a | 4-methoxy-2-hydroxybenzaldehyde | 2-chloro-4-bromophenylacetic acid, CAS 916516-89-7 |
| 1b | 4-methoxy-2-hydroxybenzaldehyde | 2,4-dichlorophenylacetic acid, CAS 19719-28-9 |
| 1c | 2,4-dihydroxybenzaldehyde | 4-chloro-2-(trifluoromethyl)phenylacetic acid, 601513-31-9 |
| 1d | 2,5-dihydroxybenzaldehyde | 2,6-dichlorophenylacetic acid, 6575-24-2 |
| 1e | 4-bromo-2-hydroxybenzaldehyde | 2-(trifluoromethyl)phenylacetic acid |
| 1f | 2,4-dihydroxybenzaldehyde | 4-butoxyphenylacetic acid |
| 1g | 2,4-dihydroxybenzaldehyde | 2-(trifluoromethyl)phenylacetic acid, 3038-48-0 |
| 1h | 4-methoxy-2-hydroxybenzaldehyde | 2-(pentafluoroethyl)phenylacetic acid, 1783371-92-5 |

-continued
| | | |
|---|---|---|
| 1i | 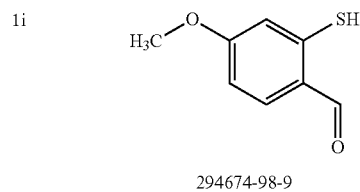 294674-98-9 | 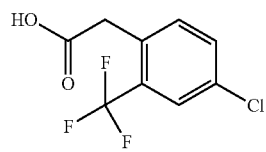 601513-31-9 |
| 1j | 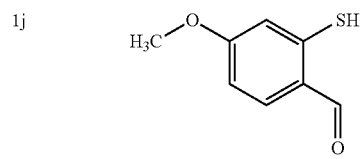 | 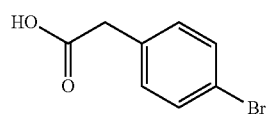 |
| 1k | 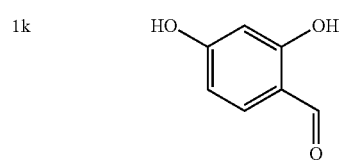 | 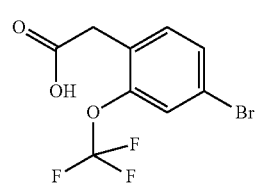 |
| 1l | 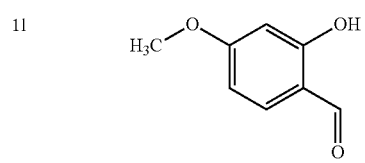 | 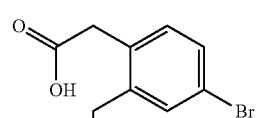 |
| 1m | 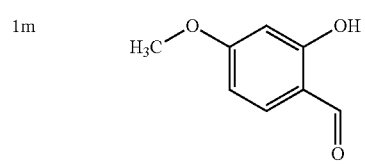 | 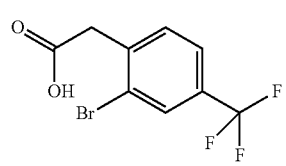 |
| 1n | 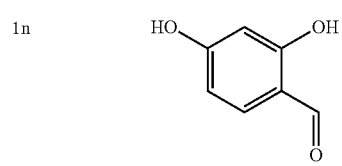 | 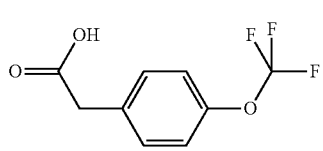 |
| 1o | 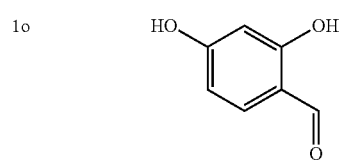 | 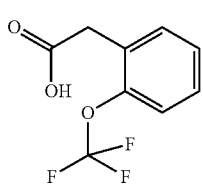 [SMILES: O=C(O)Cc1ccccc1OC(F)(F)F] |
| 1p | 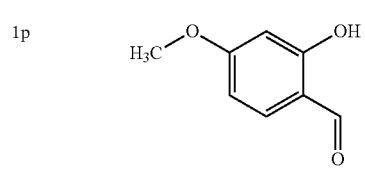 | 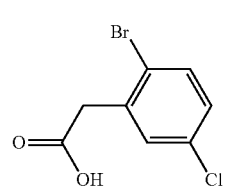 [SMILES: O=C(O)Cc1cc(Cl)ccc1Br] |
| 1q | 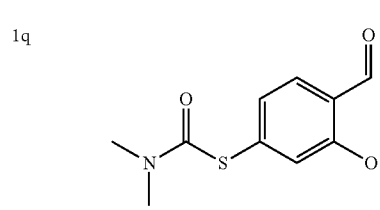 1356543-46-8 | 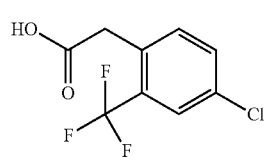 601513-31-9 |

-continued

| | Product | Yield |
|---|---|---|
| 1a | 7-methoxy-3-(4-bromo-2-chlorophenyl)-2H-chromen-2-one | 68% |
| 1b | 7-methoxy-3-(2,4-dichlorophenyl)-2H-chromen-2-one | 89% |
| 1c | 7-(hydroxycarbonyloxy)-3-(4-chloro-2-(trifluoromethyl)phenyl)-2H-chromen-2-one | 57% |
| 1d | 6-acetoxy-3-(2,6-dichlorophenyl)-2H-chromen-2-one | 73% |
| 1e | 7-bromo-3-(2-(trifluoromethyl)phenyl)-2H-chromen-2-one | 68% |
| 1f | 7-acetoxy-3-(4-butoxyphenyl)-2H-chromen-2-one | 99% |
| 1g | 7-acetoxy-3-(2-(trifluoromethyl)phenyl)-2H-chromen-2-one | 64% |

-continued
| | | |
|---|---|---|
| 1h | 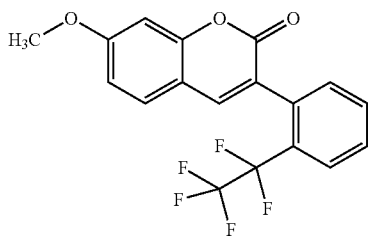 [SMILES: COc1ccc2cc(-c3ccccc3C(F)(F)C(F)(F)F)c(=O)oc2c1] | 72% |
| 1i | 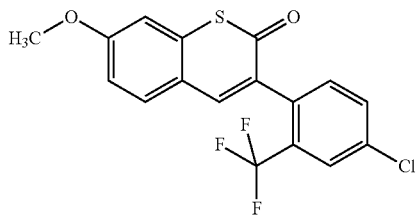 [SMILES: COc1ccc2cc(-c3ccc(Cl)cc3C(F)(F)F)c(=O)sc2c1] | 52% |
| 1j | 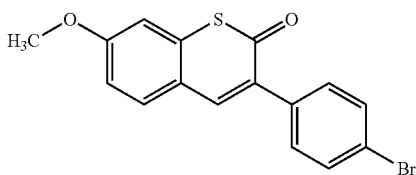 [SMILES: COc1ccc2cc(-c3ccc(Br)cc3)c(=O)sc2c1] | 65% |
| 1k | 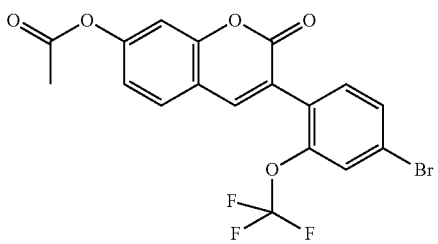 [SMILES: CC(=O)Oc1ccc2cc(-c3ccc(Br)cc3OC(F)(F)F)c(=O)oc2c1] | 69% |
| 1l | 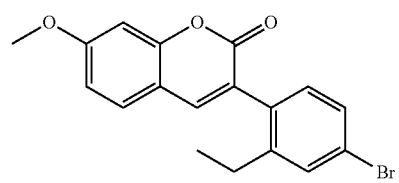 [SMILES: CCc1cc(Br)ccc1-c1cc2ccc(OC)cc2oc1=O] | 62% |
| 1m | 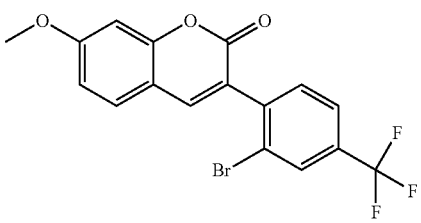 [SMILES: COc1ccc2cc(-c3ccc(C(F)(F)F)cc3Br)c(=O)oc2c1] | 57% |
| 1n | 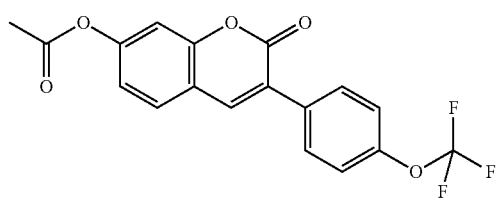 [SMILES: CC(=O)Oc1ccc2cc(-c3ccc(OC(F)(F)F)cc3)c(=O)oc2c1] | 91% |

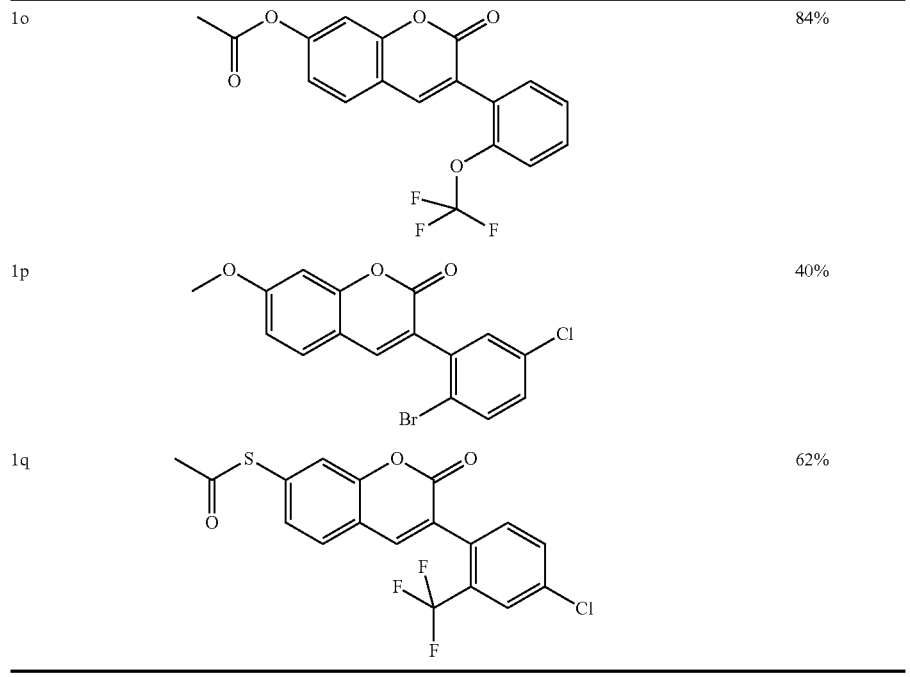

Selected NMR data:

Product 1a—¹H NMR (500 MHz, Chloroform-d) δ 7.61 (s, 1H), 7.59 (d, J=1.8 Hz, 1H), 7.40 (dd, J=8.3, 1.9 Hz, 1H), 7.36 (d, J=8.2 Hz, 1H), 7.22 (d, J=8.3 Hz, 1H), 6.82 (m, 2H), 3.83 (s, 3H).

Product 1b—¹H NMR (500 MHz, Chloroform-d) δ 7.66 (s, 1H), 7.47 (d, J=8.5 Hz, 1H), 7.45 (d, J=1.8 Hz, 1H), 7.28 (d, J=8.3 Hz, 1H), 7.26 (dd, J=8.2, 1.9 Hz, 1H), 7.11 (d, J=2.1 Hz, 1H), 7.03 (dd, J=8.4, 2.2 Hz, 1H), 2.28 (s, 3H).

Product 1c—¹H NMR (500 MHz, Chloroform-d) δ 7.79 (d, J=2.1 Hz, 1H), 7.66 (s, 1H), 7.63 (dd, J=8.2, 2.2 Hz, 1H), 7.55 (d, J=8.4 Hz, 1H), 7.39 (d, J=8.2 Hz, 1H), 7.21 (d, J=2.1 Hz, 1H), 7.13 (dd, J=8.5, 2.2 Hz, 1H), 2.39 (s, 3H).

Product 1e—¹H NMR (500 MHz, Chloroform-d) δ 7.71 (dd, J=7.9, 1.2 Hz, 1H), 7.55 (t, J=7.7 Hz, 1H), 7.53 (d, J=1.9 Hz, 1H), 7.48 (t, J=7.8 Hz, 1H), 7.38 (dd, J=8.2, 1.8 Hz, 1H), 7.34 (d, J=7.6 Hz, 1H), 7.30 (d, J=8.2 Hz, 1H).

Product 1g—¹H NMR (500 MHz, DMSO-d₆) δ 8.08 (s, 1H), 7.87 (d, J=7.9 Hz, 1H), 7.83 (d, J=8.5 Hz, 1H), 7.78 (t, J=7.5 Hz, 1H), 7.69 (t, J=7.7 Hz, 1H), 7.59 (d, J=7.6 Hz, 1H), 7.38 (d, J=1.9 Hz, 1H), 7.23 (dd, J=8.4, 2.1 Hz, 1H), 2.34 (s, 3H).

Product 1h—¹H NMR (500 MHz, DMSO-d₆) δ 7.92 (s, 1H), 7.78 (m, 2H), 7.72 (d, J=7.4 Hz, 1H), 7.68 (d, J=8.6 Hz, 1H), 7.55 (d, J=7.4 Hz, 1H), 7.08 (d, J=2.4 Hz, 1H), 7.01 (dd, J=8.6, 2.4 Hz, 1H), 3.89 (s, 3H).

Product 1i—¹H NMR (500 MHz, Chloroform-d) δ 7.67 (d, J=2.2 Hz, 1H), 7.50 (s, 1H), 7.48 (dd, J=8.4, 2.2 Hz, 1H), 7.45 (d, J=8.4 Hz, 1H), 7.23 (d, J=8.2 Hz, 1H), 6.91 (s, 1H), 6.89 (d, J=9.5, 2.5 Hz, 1H), 3.84 (s, 3H).

Product 1j—¹H NMR (500 MHz, Chloroform-d) δ 7.64 (s, 1H), 7.48 (m, 3H), 7.35 (d, J=8.5 Hz, 2H), 6.91–6.87 (m, 2H), 3.83 (s, 3H).

Product 1k—¹H NMR (500 MHz, DMSO-d₆) δ 8.23 (s, 1H), 7.85 (d, J=8.5 Hz, 1H), 7.79–7.74 (m, 2H), 7.60 (d, J=8.6 Hz, 1H), 7.38 (d, J=2.1 Hz, 1H), 7.24 (dd, J=8.4, 2.2 Hz, 1H), 2.34 (s, 3H).

Product 1l—¹H NMR (500 MHz, DMSO-d₆) δ 7.98 (d, J=1.3 Hz, 1H), 7.68 (dd, J=8.6, 1.4 Hz, 1H), 7.54 (s, 1H), 7.46 (d, J=8.3 Hz, 1H), 7.22 (dd, J=8.2, 1.4 Hz, 1H), 7.07 (s, 1H), 7.01 (d, J=8.6 Hz, 1H), 3.89 (s, 3H), 2.57–2.46 (m, 2H), 1.09 (t, J=7.5 Hz, 3H).

Product 1m—¹H NMR (500 MHz, DMSO-d₆) δ 8.13 (m, 2H), 7.88 (d, J=7.8 Hz, 1H), 7.74 (d, J=8.0 Hz, 1H), 7.71 (d, J=8.7 Hz, 1H), 7.11 (d, J=2.4 Hz, 1H), 7.04 (dd, J=8.6, 2.4 Hz, 1H), 3.91 (s, 3H).

Product 1n—¹H NMR (500 MHz, Chloroform-d) δ 7.84 (s, 1H), 7.76 (d, J=8.8 Hz, 2H), 7.58 (d, J=8.5 Hz, 1H), 7.32 (d, J=8.2 Hz, 2H), 7.19 (d, J=2.1 Hz, 1H), 7.12 (dd, J=8.4, 2.2 Hz, 1H), 2.38 (s, 3H).

Product 1o—¹H NMR (500 MHz, Chloroform-d) δ 7.77 (s, 1H), 7.56 (d, J=8.5 Hz, 1H), 7.53 (dd, J=7.8, 1.7 Hz, 1H), 7.51–7.45 (m, 1H), 7.42–7.38 (m, 2H), 7.20 (d, J=2.2 Hz, 1H), 7.12 (dd, J=8.4, 2.2 Hz, 1H), 2.38 (s, 3H).

Product 1p—¹H NMR (500 MHz, Chloroform-d) δ 7.69 (s, 1H), 7.62 (d, J=8.6 Hz, 1H), 7.46 (d, J=8.4 Hz, 1H), 7.42 (d, J=2.5 Hz, 1H), 7.26 (dd, J=8.6, 2.6 Hz, 1H), 6.94–6.89 (m, 2H), 3.93 (s, 3H).

Product 1q—¹H NMR (500 MHz, Chloroform-d) δ 7.80 (d, J=2.0 Hz, 1H), 7.68 (s, 1H), 7.63 (dd, J=8.2, 2.0 Hz, 1H), 7.57 (d, J=8.0 Hz, 1H), 7.51 (d, J=1.1 Hz, 1H), 7.39 (d, J=8.3 Hz, 1H), 7.39 (dd, J=8.0, 1.6 Hz, 1H), 2.52 (s, 3H).

Example 2

Acetic acid 3-(4-pentyl-phenyl)-coumarin-7-yl ester

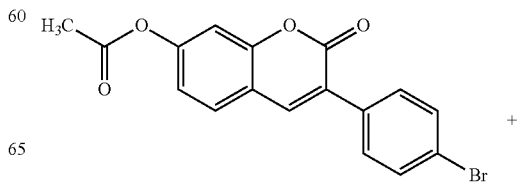

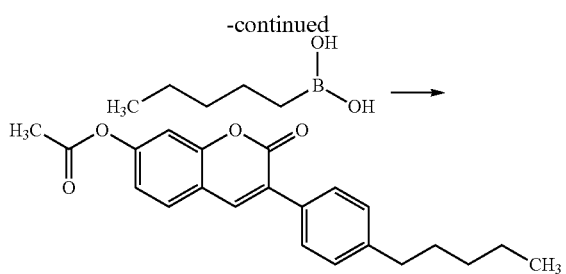

3.0 g (8.4 mmol) of acetic acid 3-(4-bromophenyl)-coumarin-7-yl ester, 1.0 g (8.8 mmol) of n-pentylboronic acid and 3.7 g (17.5 mmol) of tri-potassium phosphate trihydrate are dissolved in 80 ml of toluene and degassed. 171 mg (0.4 mmol) of 2-dicyclohexylphoshino-2',6'-dimethoxy-1,1'-biphenyl and 47 mg (0.2 mmol) of palladium(II) acetate are added. The reaction mixture is subsequently stirred at 110° C. for 24 h under a protective-gas atmosphere. The cooled solution is diluted with ethyl acetate and washed with water, dried and evaporated. The product is purified by column chromatography on silica gel (heptane/ethyl acetate). Yield: 2.5 g (7.1 mmol), 85% of theory.

$^1$H NMR (500 MHz, DMSO-$d_6$) δ 8.29 (s, 1H), 7.86 (d, J=8.4 Hz, 1H), 7.70 (d, J=8.2 Hz, 2H), 7.36 (d, J=2.2 Hz, 1H), 7.34 (d, J=8.3 Hz, 2H), 7.24 (dd, J=8.4, 2.2 Hz, 1H), 2.68 (t, J=7.6 Hz, 2H), 2.37 (s, 3H), 1.66 (p, J=7.5 Hz, 2H), 1.42-1.29 (m, 4H), 0.93 (t, J=7.0 Hz, 3H).

The following compounds 2a to 2g are prepared analogously:

| | Reactant 1 | Reactant 2 |
|---|---|---|
| 2a | | |
| 2b | | |
| 2c | | |
| 2d | | |
| 2e | | |

-continued
| | | |
|---|---|---|
| 2f | 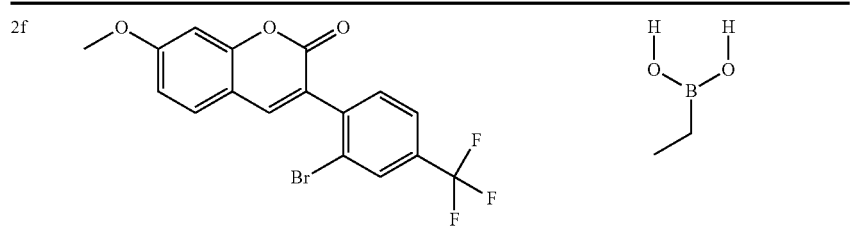 | |
| 2g | 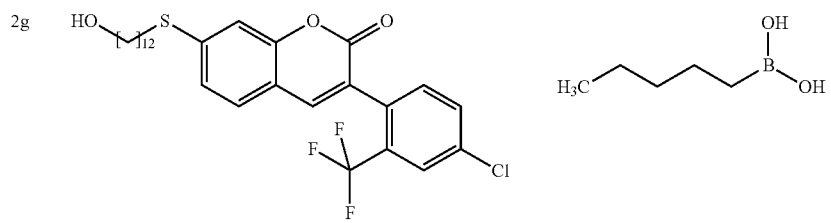 | |
| | Product | Yield |
|---|---|---|
| 2a | 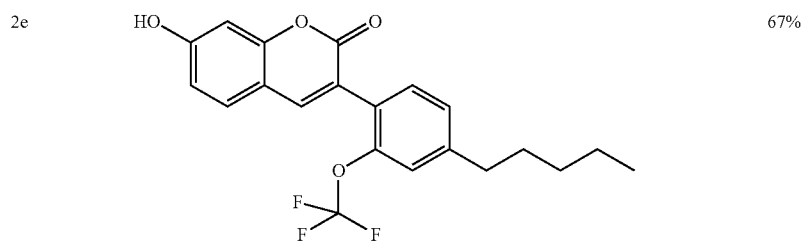 | 31% |
| 2b | | 43% |
| 2c | | 53% |
| 2d | | 76% |
| 2e | | 67% |

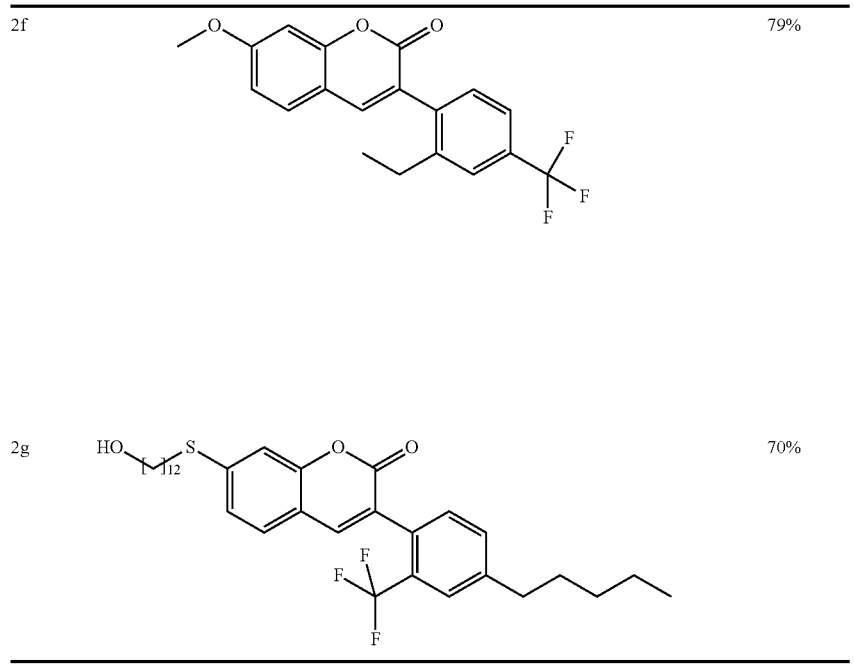

2f 79%

2g 70%

Selected NMR data:

Product 2a—¹H NMR (500 MHz, Chloroform-d) δ 7.60 (s, 1H), 7.34 (d, J=9.2 Hz, 1H), 7.25–7.22 (m, 2H), 7.06 (d, J=8.7 Hz, 1H), 6.82–6.77 (m, 2H), 3.83 (s, 3H), 1.61–1.52 (m, 2H), 1.32–1.22 (m, 4H), 0.84 (t, J=6.8 Hz, 3H).

Product 2b—¹H NMR (500 MHz, Chloroform-d) δ 7.65 (s, 1H), 7.47 (d, J=9.4 Hz, 1H), 7.39 (d, J=7.8 Hz, 2H), 7.14 (d, J=7.9 Hz, 2H), 6.90–6.84 (m, 2H), 3.82 (s, 3H), 2.56 (t, J=7.7 Hz, 2H), 1.62–1.52 (m, 2H), 1.31–1.24 (m, 4H), 0.83 (t, J=6.7 Hz, 3H).

Product 2c—¹H NMR (500 MHz, Chloroform-d) δ 7.55 (s, 1H), 7.50 (d, J=1.7 Hz, 1H), 7.43 (d, J=8.5 Hz, 1H), 7.35 (d, J=8.7 Hz, 1H), 7.23 (d, J=7.8 Hz, 1H), 7.10 (d, J=2.2 Hz, 1H), 7.01 (dd, J=8.4, 2.2 Hz, 1H), 2.66–2.60 (m, 2H), 2.28 (s, 3H), 1.60 (p, J=7.4 Hz, 2H), 1.33–1.24 (m, 4H), 0.92–0.82 (m, 3H).

Product 2d—¹H NMR (500 MHz, Chloroform-d) δ 7.60 (s, 1H), 7.57 (s, 1H), 7.52 (d, J=8.5 Hz, 1H), 7.41 (d, J=7.8 Hz, 1H), 7.27 (d, J=7.9 Hz, 1H), 7.00 (d, J=2.3 Hz, 1H), 6.98 (dd, J=8.6, 2.4 Hz, 1H), 3.93 (s, 2H), 2.75–2.62 (m, 2H), 1.69 (p, J=7.3 Hz, 2H), 1.39 (dt, J=7.2, 3.7 Hz, 4H), 0.95 (t, J=6.8 Hz, 3H).

Product 2e—¹H NMR (500 MHz, Chloroform-d) δ 7.72 (s, 1H), 7.43 (d, J=8.0 Hz, 2H), 7.23–7.15 (m, 2H), 6.98 (d, J=2.4 Hz, 1H), 6.86 (dd, J=8.5, 2.4 Hz, 1H), 6.01 (s, 1H), 2.71–2.66 (m, 2H), 1.67 (m, 2H), 1.38 (m, 4H), 0.94 (t, J=6.9 Hz, 3H).

Product 2f—¹H NMR (500 MHz, DMSO-d₆) δ 8.05 (s, 1H), 7.69 (d, J=8.6 Hz, 1H), 7.69 (s, 1H), 7.63 (d, J=7.9 Hz, 1H), 7.50 (d, J=7.9 Hz, 1H), 7.09 (d, J=2.4 Hz, 1H), 7.02 (dd, J=8.6, 2.4 Hz, 1H), 3.90 (s, 3H), 2.63 (q, J=7.5 Hz, 2H), 1.12 (t, J=7.5 Hz, 3H).

Product 2g—¹H NMR (500 MHz, Chloroform-d) δ 7.60 (s, 1H), 7.59 (s, 1H), 7.44 (d, J=7.8 Hz, 1H), 7.38 (d, J=8.2 Hz, 1H), 7.33 (d, J=7.8 Hz, 1H), 7.23 (s, 1H), 7.18 (dd, J=8.1, 1.7 Hz, 1H), 3.03 (t, J=7.4 Hz, 2H), 2.74–2.65 (m, 2H), 1.75 (p, J=7.5 Hz, 2H), 1.69 (p, J=7.7, 7.3 Hz, 2H), 1.62–1.54 (m, 2H), 1.49 (p, J=7.2 Hz, 2H), 1.38 (p, J=3.7 Hz, 2H), 1.35–1.27 (m, 18H), 0.94 (t, J=6.8 Hz, 3H).

Example 3-3

(2,4-Dichloro-phenyl)-7-methoxy-chromene-2-thione

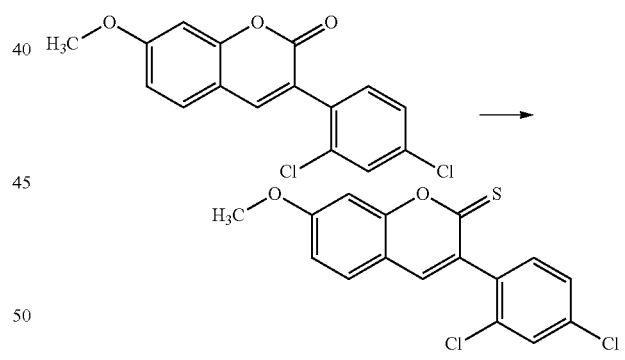

1.0 g (3.1 mmol) 3-(2,4-dichloro-phenyl)-7-methoxy-coumarin and 1.4 g (3.4 mmol) Lawesson's reagent are added to toluene (17 ml). The reaction vessel is heated to 100° C. for 24 h. The cooled reaction mixture is transferred to a separatory funnel, diluted ethyl acetate and extracted with water. The organic layer is dried over MgSO₄, concentrated under reduced pressure and purified by column chromatography. 811 mg (2.4 mmol; 77% of theory) 3-(2,4-dichlorophenyl)-7-methoxy- chromene-2-thione are isolated.

¹H NMR (500 MHz, DMSO-d₆) δ 8.01 (s, 1H), 7.77 (d, J=8.7 Hz, 1H), 7.73 (d, J=2.0 Hz, 1H), 7.52 (dd, J=8.3, 2.1 Hz, 1H), 7.47 (d, J=8.2 Hz, 1H), 7.32 (d, J=2.3 Hz, 1H), 7.12 (dd, J=8.7, 2.4 Hz, 1H), 3.94 (s, 3H).

The following compound 3a is prepared analogously:

| | Reactant | Product | Yield |
|---|---|---|---|
| 3a | 7-methoxy-3-(4-pentyl-2-(trifluoromethyl)phenyl)-2H-chromene-2-one structure | 7-methoxy-3-(4-pentyl-2-(trifluoromethyl)phenyl)-2H-chromene-2-thione structure | 68% |

Example 4

(2,4-Diisopropyl-phenyl)-7-methoxy-coumarin

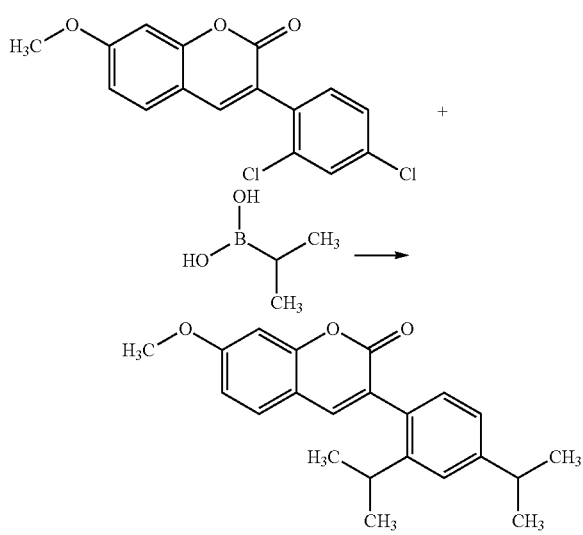

161 mg (0.5 mmol) 3-(2,4-dichloro-phenyl)-7-methoxy-coumarin, 132 mg (1.5 mmol) isopropylboronic acid, 414 mg (3 mmol) potassium carbonate and 28.6 mg (0.05 mmol) methanesulfonato(tri-t-butylphosphino)(2'-amino-1,1'-biphenyl-2-yl)palladium(II) are added to a flask. Degassed toluene (1 ml) and water (0.50 ml) are then added via syringe. The reaction vessel is heated to 100° C. for 24 h. The cooled reaction mixture is diluted with ethyl acetate, filtered, concentrated under reduced pressure, and purified by column chromatography. 128 mg (0.4 mmol; 76% of theory) 3-(2,4-Diisopropyl-phenyl)-7-methoxy-chromen-2-one are isolated.

$^1$H NMR (500 MHz, DMSO-d$_6$) δ 7.92 (s, 1H), 7.65 (d, J=8.7 Hz, 1H), 7.33 (d, J=8.3 Hz, 1H), 7.26 (s, 1H), 7.11 (s, 1H), 7.05 (d, J=2.4 Hz, 1H), 6.99 (dd, J=8.6, 2.5 Hz, 1H), 3.88 (s, 3H), 2.94 (p, J=6.8 Hz, 1H), 2.81 (p, J=6.8 Hz, 1H), 1.25 (s, 6H), 1.24 (s, 6H).

The following compounds 4a to 4e are prepared analogously:

| | Reactant 1 | Reactant 2 |
|---|---|---|
| 4a | 3-(3,4-dichlorophenyl)-7-methoxy-2H-chromen-2-one | sec-butylboronic acid, 88496-88-2 |
| 4b | 3-(2-chloro-4-pentylphenyl)-7-methoxy-2H-chromen-2-one | ethylboronic acid |
| 4c | 7-acetoxy-3-(2,6-dichlorophenyl)-2H-chromen-2-one | ethylboronic acid |

| | | |
|---|---|---|
| 4d | ![7-methoxy-3-(3,5-dichlorophenyl)coumarin structure] | ![ethylboronic acid structure] |
| 4e | ![7-methoxy-3-(2,4-dichlorophenyl)-2H-chromene-2-thione structure] | ![ethylboronic acid structure] |

| | Product | Yield |
|---|---|---|
| 4a | ![7-methoxy-3-(2,4-di-sec-butylphenyl)coumarin structure] | 53% |
| 4b | ![7-methoxy-3-(2-ethyl-4-pentylphenyl)coumarin structure] | 42% |
| 4c | ![6-acetoxy-3-(2,6-diethylphenyl)coumarin structure] | 31% |
| 4d | ![7-methoxy-3-(2,4-diethylphenyl)coumarin structure] | 20% |
| 4e | ![7-methoxy-3-(2,4-diethylphenyl)-2H-chromene-2-thione structure] | 27% |

Selected NMR data:

Product 4b—$^1$H NMR (500 MHz, DMSO-d$_6$) δ 7.92 (s, 1H), 7.65 (d, J=8.7 Hz, 1H), 7.13 (s, 1H), 7.12 (d, J=8.3 Hz, 1H), 7.06 (dd, J=7.9, 1.9 Hz, 1H), 7.05 (d, J=2.4 Hz, 1H), 6.98 (dd, J=8.6, 2.4 Hz, 1H), 3.88 (s, 3H), 2.62–2.55 (m, 2H), 2.49–2.46 (m, 2H), 1.67–1.54 (m, 2H), 1.35–1.26 (m, 4H), 1.07 (t, J=7.5 Hz, 3H), 0.88 (t, J=7.0 Hz, 3H).

Product 4d—$^1$H NMR (500 MHz, DMSO-d$_6$) δ 7.92 (s, 1H), 7.66 (d, J=8.6 Hz, 1H), 7.16 (s, 1H), 7.14 (d, J=7.7 Hz, 1H), 7.09 (dd, J=7.8, 1.5 Hz, 1H), 7.06 (d, J=2.4 Hz, 1H), 7.00 (dd, J=8.6, 2.4 Hz, 1H), 3.89 (s, 3H), 2.64 (q, J=7.6 Hz, 2H), 2.50 (q, J=7.2 Hz, 2H), 1.22 (t, J=7.6 Hz, 3H), 1.09 (t, J=7.5 Hz, 3H).

Product 4e—$^1$H NMR (500 MHz, DMSO-d$_6$) δ 8.03 (s, 1H), 7.69 (d, J=8.6 Hz, 1H), 7.42 (d, J=1.4 Hz, 1H), 7.40 (d, J=7.8 Hz, 1H), 7.28 (dd, J=7.8, 1.6 Hz, 1H), 7.07 (d, J=2.4 Hz, 1H), 7.01 (dd, J=8.6, 2.4 Hz, 1H), 3.90 (s, 3H), 2.67 (q, J=7.6 Hz, 2H), 2.50 (q, J=7.2 Hz, 2H), 1.23 (t, J=7.6 Hz, 3H), 1.09 (t, J=7.5 Hz, 3H).

Example 5

7-Hydroxy-3-(4-pentyl-phenyl)-thiocoumarin

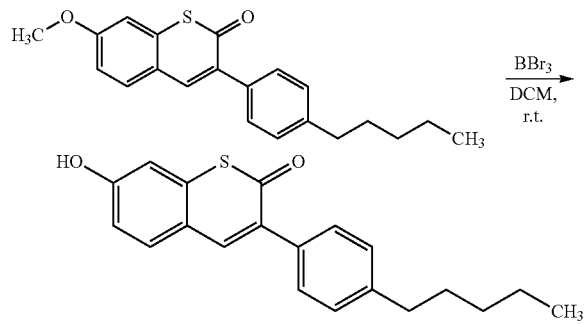

1.4 g (4.3 mmol) of 7-Methoxy-3-(4-pentyl-phenyl)-thiocoumarin are dissolved in 50 ml of dichloromethane and cooled to 5° C. 0.4 ml (4.3 mmol) of boron tribromide are added dropwise to this solution over the course of 10 min, and stirring is continued overnight. Water is subsequently slowly added to the mixture, and the organic phase is diluted with ethyl acetate, washed three times with water, dried over MgSO$_4$, evaporated in a rotary evaporator and purified by recrystallization from ethanol. Yield: 1.3 g (4 mmol), 94% of theory.

$^1$H NMR (500 MHz, DMSO-d$_6$) δ10.60 (s, 1H), 8.05 (s, 1H), 7.79 (d, J=8.6 Hz, 1H), 7.45 (d, J=8.2 Hz, 1H), 7.25 (d, J=8.2 Hz, 2H), 6.97 (d, J=2.3 Hz, 1H), 6.93 (dd, J=8.6, 2.4 Hz, 1H), 2.61 (t, J=7.6 Hz, 2H), 1.61 (p, J=7.5 Hz, 2H), 1.39-1.26 (m, 4H), 0.88 (t, J=7.0 Hz, 3H).

The following compounds 5a to 5g are prepared analogously:

| | Reactant | Product | Yield |
|---|---|---|---|
| 5a | | | 98% |
| 5b | | | 90% |
| 5c | | | 92% |
| 5d | | | 95% |
| 5e | | | 97% |

| | Reactant | Product | Yield |
|---|---|---|---|
| 5f | 7-methoxy-coumarin-2-thione with 2,4-diethylphenyl substituent | 7-hydroxy-coumarin-2-thione with 2,4-diethylphenyl substituent | 95% |
| 5g | 7-methoxy-thiocoumarin-2-thione with 2-CF₃-4-pentylphenyl substituent | 7-hydroxy-thiocoumarin-2-thione with 2-CF₃-4-pentylphenyl substituent | 82% |

Selected NMR data:

Product 5a—¹H NMR (500 MHz, DMSO-d₆) δ 7.90 (s, 1H), 7.74 (d, J=8.6 Hz, 1H), 7.62 (s, 1H), 7.55 (d, J=7.6 Hz, 1H), 7.35 (d, J=7.8 Hz, 1H), 7.01 (d, J=2.1 Hz, 1H), 6.94 (dd, J=8.6, 2.3 Hz, 1H), 2.74–2.68 (m, 2H), 1.63 (p, J=7.5 Hz, 2H), 1.40–1.24 (m, 4H), 0.89 (t, J=6.9 Hz, 3H).

Product 5c—¹H NMR (500 MHz, DMSO-d₆) δ 7.92 (s, 1H), 7.65 (d, J=8.7 Hz, 1H), 7.33 (d, J=8.3 Hz, 1H), 7.26 (s, 1H), 7.11 (s, 1H), 7.05 (d, J=2.4 Hz, 1H), 6.99 (dd, J=8.6, 2.5 Hz, 1H), 2.94 (p, J=6.8 Hz, 1H), 2.81 (p, J=6.8 Hz, 1H), 1.25 (s, 6H), 1.24 (s, 6H).

Product 5d—¹H NMR (500 MHz, DMSO-d₆) δ 7.86 (s, 1H), 7.55 (d, J=8.5 Hz, 1H), 7.13 (d, J=1.7 Hz, 1H), 7.11 (d, J=7.7 Hz, 1H), 7.06 (dd, J=7.8, 1.4 Hz, 1H), 6.82 (dd, J=8.4, 2.2 Hz, 1H), 6.77 (d, J=2.1 Hz, 1H), 2.63–2.55 (m, 2H), 2.50–2.45 (m, 2H), 1.60 (q, J=7.5 Hz, 2H), 1.38–1.28 (m, 4H), 1.08 (t, J=7.5 Hz, 3H), 0.89 (t, J=7.0 Hz, 3H).

Product 5e—¹H NMR (500 MHz, DMSO-d₆) δ 10.59 (s, 1H), 7.86 (s, 1H), 7.55 (d, J=8.5 Hz, 1H), 7.15 (s, 1H), 7.12 (d, J=7.7 Hz, 1H), 7.08 (dd, J=7.7, 1.8 Hz, 1H), 6.82 (dd, J=8.5, 2.3 Hz, 1H), 6.77 (d, J=2.3 Hz, 1H), 2.64 (q, J=7.6 Hz, 2H), 2.56–2.42 (m, 2H), 1.22 (t, J=7.6 Hz, 3H), 1.08 (t, J=7.5 Hz, 3H).

Example 6

7-Hydroxy-3-(4-pentyl-phenyl)-coumarin

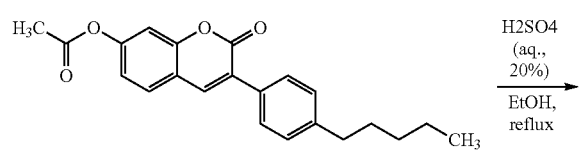

2.5 g (7.1 mmol) acetic acid 3-(4-pentyl-phenyl)-coumarin-7-yl ester are suspended in a mixture of 14 ml ethanol and 10 ml sulfuric acid (20%, aq.) and refluxed for 2 h. The batch is then cooled to room temperature, and the solid which has precipitated out is filtered off with suction and rinsed neutral with water. The yield is 2.2 g (7.1 mmol), 99% of theory.

¹H NMR (500 MHz, DMSO-d₆) δ 10.56 (s, 1H), 8.12 (s, 1H), 7.61 (d, J=8.2 Hz, 2H), 7.59 (d, J=8.6 Hz, 1H), 7.25 (d, J=8.1 Hz, 2H), 6.83 (dd, J=8.5, 2.2 Hz, 1H), 6.76 (d, J=2.1 Hz, 1H), 2.61 (t, J=7.6 Hz, 2H), 1.60 (p, J=7.5 Hz, 2H), 1.37–1.36 (m, 4H), 0.88 (t, J=7.0 Hz, 3H).

The following compounds 6a to 6h were prepared analogously:

| | Reactant | Product | Yield |
|---|---|---|---|
| 6a | acetoxy-coumarin with 2-(trifluoromethyl)phenyl substituent | 7-hydroxy-coumarin with 2-(trifluoromethyl)phenyl substituent | 90% |

-continued

| | Reactant | Product | Yield |
|---|---|---|---|
| 6b | 7-acetoxy-3-[2-(pentafluoroethyl)phenyl]-2H-chromen-2-one | 7-hydroxy-3-[2-(pentafluoroethyl)phenyl]-2H-chromen-2-one | 89% |
| 6c | 7-acetoxy-3-[4-pentyl-2-(trifluoromethyl)phenyl]-2H-chromen-2-one | 7-hydroxy-3-[4-pentyl-2-(trifluoromethyl)phenyl]-2H-chromen-2-one | 99% |
| 6d | 7-acetoxy-3-(4-butoxyphenyl)-2H-chromen-2-one | 7-hydroxy-3-(4-butoxyphenyl)-2H-chromen-2-one | 80% |
| 6e | 6-acetoxy-3-(2,6-diethylphenyl)-2H-chromen-2-one | 6-hydroxy-3-(2,6-diethylphenyl)-2H-chromen-2-one | 99% |
| 6f | S-{3-[4-chloro-2-(trifluoromethyl)phenyl]-2-oxo-2H-chromen-7-yl} ethanethioate | 7-mercapto-3-[4-chloro-2-(trifluoromethyl)phenyl]-2H-chromen-2-one | 59% |
| 6g | 7-acetoxy-3-[4-(trifluoromethoxy)phenyl]-2H-chromen-2-one | 7-hydroxy-3-[4-(trifluoromethoxy)phenyl]-2H-chromen-2-one | 75% |
| 6h | 7-acetoxy-3-[2-(trifluoromethoxy)phenyl]-2H-chromen-2-one | 7-hydroxy-3-[2-(trifluoromethoxy)phenyl]-2H-chromen-2-one | 89% |

Selected NMR data:

Product 6a—¹H NMR (500 MHz, DMSO-d₆) δ 10.65 (s, 1H), 7.92 (s, 1H), 7.84 (d, J=7.9 Hz, 1H), 7.75 (t, J=7.5 Hz, 1H), 7.66 (t, J=7.7 Hz, 1H), 7.59 (d, J=8.5 Hz, 1H), 7.54 (d, J=7.6 Hz, 1H), 6.84 (dd, J=8.5, 2.3 Hz, 1H), 6.80 (d, J=2.2 Hz, 1H).

Product 6b—¹H NMR (500 MHz, DMSO-d₆) δ 10.64 (s, 1H), 7.86 (s, 1H), 7.80-7.75 (m, 2H), 7.70 (t, J=7.4 Hz, 1H), 7.58 (d, J=8.5 Hz, 1H), 7.52 (d, J=7.3 Hz, 1H), 6.84 (dd, J=8.5, 2.3 Hz, 1H), 6.79 (d, J=2.2 Hz, 1H).

Product 6c—¹H NMR (500 MHz, DMSO-d₆) δ 10.63 (s, 1H), 7.89 (s, 1H), 7.63 (s, 1H), 7.57 (d, J=8.5 Hz, 1H), 7.56 (d, J=7.7 Hz, 1H), 7.42 (d, J=7.8 Hz, 1H), 6.83 (dd, J=8.5, 2.2 Hz, 1H), 6.79 (d, J=2.2 Hz, 1H), 2.76-2.69 (m, 2H), 1.64 (p, J=7.5 Hz, 2H), 1.40-1.26 (m, 4H), 0.89 (t, J=6.9 Hz, 3H).

Product 6d—¹H NMR (500 MHz, DMSO-d₆) δ 10.51 (s, 1H), 8.08 (s, 1H), 7.65 (d, J=8.9 Hz, 2H), 7.59 (d, J=8.5 Hz, 1H), 6.99 (d, J=8.9 Hz, 2H), 6.82 (dd, J=8.5, 2.3 Hz, 1H), 6.75 (d, J=2.2 Hz, 1H), 4.02 (t, J=6.5 Hz, 2H), 1.78-1.66 (m, 2H), 1.51-1.41 (m, 2H), 0.95 (t, J=7.4 Hz, 2H).

Product 6f—¹H NMR (500 MHz, Chloroform-d) δ 7.77 (d, J=2.0 Hz, 1H), 7.61 (dd, J=8.4, 2.2 Hz, 1H), 7.60 (s, 1H), 7.40-7.36 (m, 2H), 7.28 (d, J=1.4 Hz, 1H), 7.18 (dd, J=8.1, 1.7 Hz, 1H), 3.80 (s, 1H).

Product 6g—¹H NMR (500 MHz, DMSO-d₆) δ 10.68 (s, 1H), 8.23 (s, 1H), 7.84 (d, J=8.8 Hz, 2H), 7.62 (d, J=8.5 Hz, 1H), 7.45 (d, J=8.2 Hz, 2H), 6.85 (dd, J=8.5, 2.3 Hz, 1H), 6.78 (d, J=2.2 Hz, 1H).

Product 6h—¹H NMR (500 MHz, DMSO-d₆) δ 10.68 (s, 1H), 8.04 (s, 1H), 7.61 (d, J=8.5 Hz, 1H), 7.57 (td, J=7.4, 1.7 Hz, 1H), 7.49 (dd, J=7.2, 1.3 Hz, 1H), 7.46 (d, J=7.6 Hz, 1H), 6.85 (dd, J=8.5, 2.3 Hz, 1H), 6.80 (d, J=2.1 Hz, 1H).

Example 7

7-(11-Hydroxy-undecyloxy)-3-(4-pentyl-phenyl)-coumarin

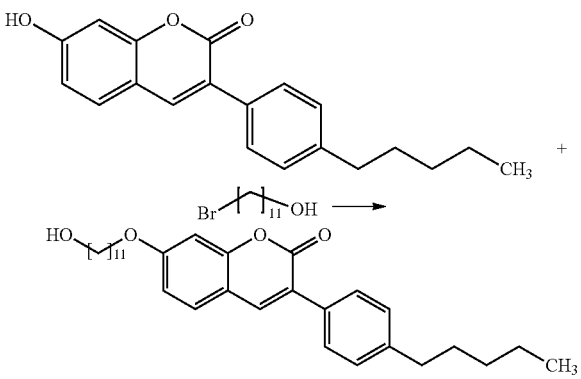

2.37 g (7.7 mmol) 7-hydroxy-3-(4-pentyl-phenyl)-coumarin and 2.0 g (8.0 mmol) 11-bromo-1-undecanol are dissolved in 23 ml acetone and 4.3 g (30.7 mmol) potassium carbonate are added. The suspension is refluxed for 2 d. The hot reaction mixture is filtered, washed with hot acetone (2x). The filtrate is evaporated under reduced pressure. The remaining solid is purified by column chromatography (SiO₂, heptane/ethyl acetate). 7-(11-Hydroxy-undecyloxy)-3-(4-pentyl-phenyl)-coumarin is isolated. The yield is 2.8 g (5.9 mmol) (76% of theory).

¹H NMR (500 MHz, DMSO-d₆) δ 8.17 (s, 1H), 7.67 (d, J=8.7 Hz, 1H), 7.63 (d, J=8.2 Hz, 2H), 7.27 (d, J=8.3 Hz, 2H), 7.01 (d, J=2.3 Hz, 1H), 6.97 (dd, J=8.6, 2.4 Hz, 1H), 4.29 (t, J=4.4 Hz, 1H), 4.09 (t, J=6.5 Hz, 2H), 3.38 (q, J=6.4 Hz, 2H), 2.62 (t, J=7.6 Hz, 2H), 1.75 (p, J=6.6 Hz, 2H), 1.61 (p, J=7.5 Hz, 2H), 1.48-1.37 (m, 4H), 1.37-1.21 (m, 16H), 0.88 (t, J=7.0 Hz, 3H).

The following compounds 7a to 7w are prepared analogously:

| | Reactant 1 | Reactant 2 |
|---|---|---|
| 7a | 7-hydroxy-thiocoumarin with 3-(4-pentyl-phenyl) substituent | Br(CH₂)₁₁OH |
| 7b | 7-hydroxy-thiocoumarin with 3-[2-(CF₃)-4-pentyl-phenyl] substituent | 4-bromo-2,2-dimethyl-1-butanol |

1246447-80-2

-continued
| | | |
|---|---|---|
| 7c | 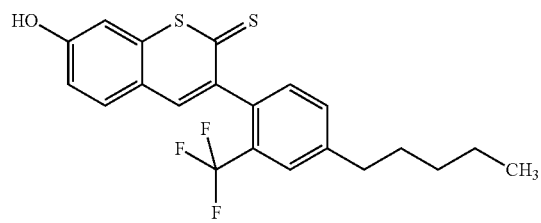 | 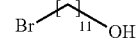 |
| 7d | 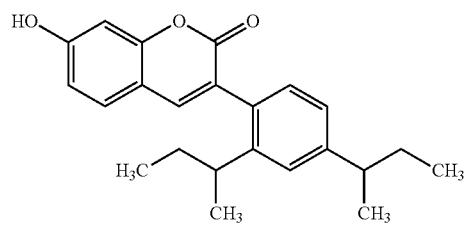 [SMILES: CCC(C)c1ccc(-c2cc3ccc(O)cc3oc2=O)c(C(C)CC)c1] | 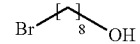 |
| 7e | 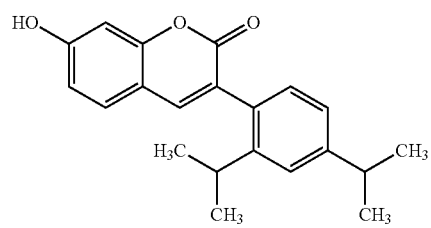 [SMILES: CC(C)c1ccc(-c2cc3ccc(O)cc3oc2=O)c(C(C)C)c1] | 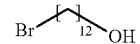 |
| 7f | 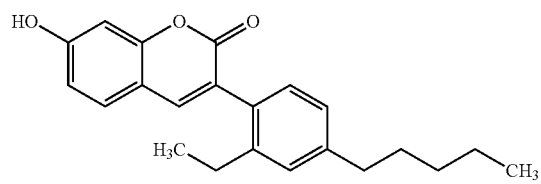 [SMILES: CCCCCc1ccc(-c2cc3ccc(O)cc3oc2=O)c(CC)c1] | 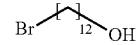 |
| 7g | 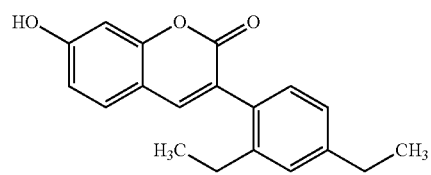 | 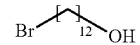 |
| 7h | 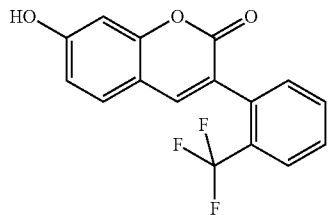 [SMILES: O=c1oc2cc(O)ccc2cc1-c1ccccc1C(F)(F)F] | 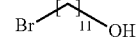 |
| 7i | 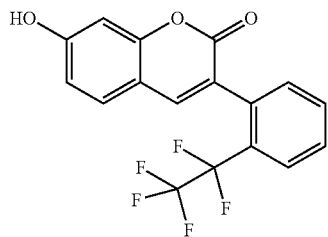 [SMILES: O=c1oc2cc(O)ccc2cc1-c1ccccc1C(F)(F)C(F)(F)F] | 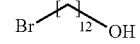 |

-continued
| | | |
|---|---|---|
| 7j | 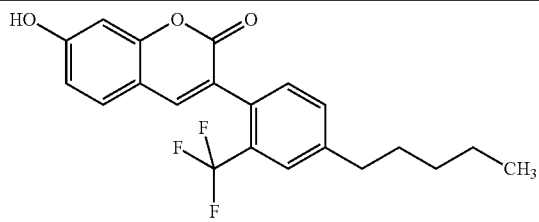 | 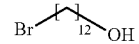 |
| 7k | 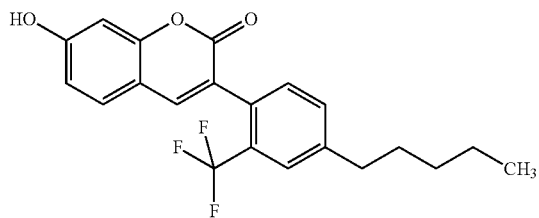 | 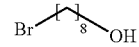 |
| 7m | 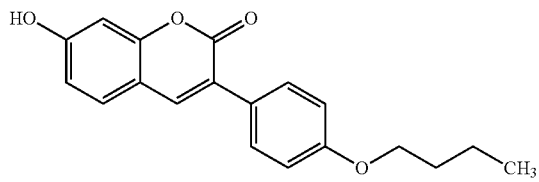 [SMILES: CCCCOc1ccc(-c2cc3ccc(O)cc3oc2=O)cc1] | 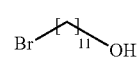 |
| 7n | 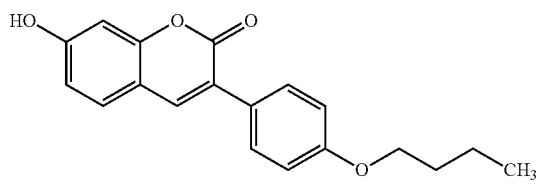 [SMILES: CCCCOc1ccc(-c2cc3ccc(O)cc3oc2=O)cc1] | 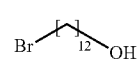 |
| 7o | 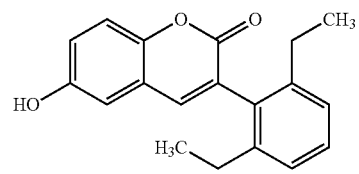 [SMILES: CCc1cccc(CC)c1-c1cc2cc(O)ccc2oc1=O] | 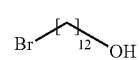 |
| 7p | 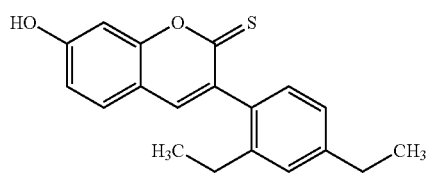 | 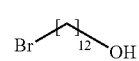 |
| 7q | 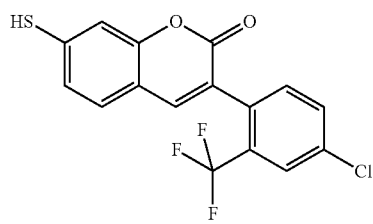 [SMILES: O=c1oc2cc(S)ccc2cc1-c1ccc(Cl)cc1C(F)(F)F] | 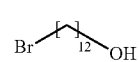 |
| 7r | 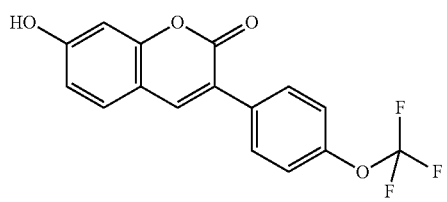 [SMILES: O=c1oc2cc(O)ccc2cc1-c1ccc(OC(F)(F)F)cc1] |  |

| | | |
|---|---|---|
| 7s | 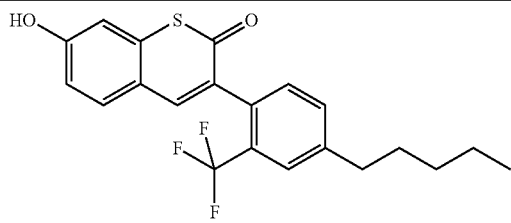 | 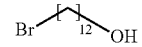 |
| 7t | 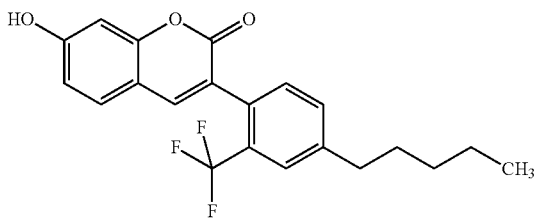 | 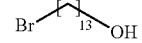 |
| 7u | 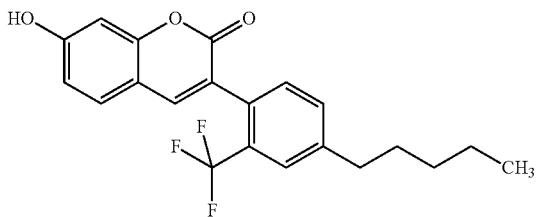 | 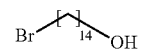 |
| 7v | 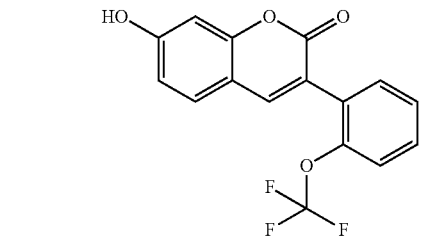 [SMILES: O=c1oc2cc(O)ccc2cc1-c1ccccc1OC(F)(F)F] | 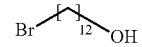 |
| 7w | 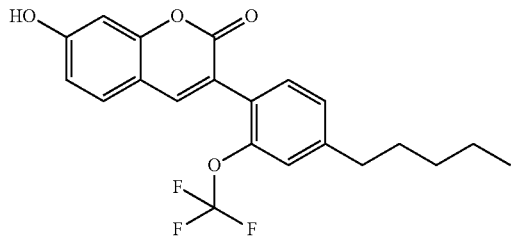 [SMILES: CCCCCc1ccc(-c2cc3ccc(O)cc3oc2=O)c(OC(F)(F)F)c1] | 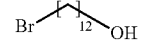 |
| | Product | Yield |
|---|---|---|
| 7a | 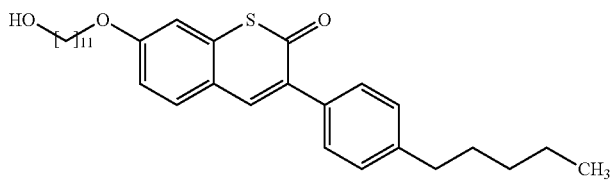 | 83% |
| 7b | 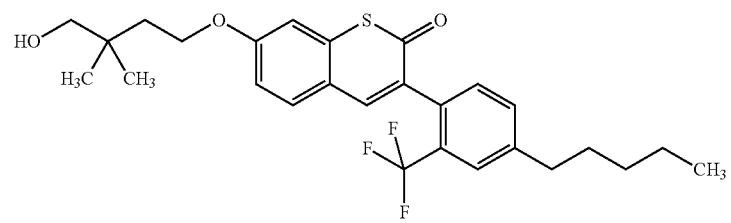 [SMILES: CCCCCc1ccc(-c2cc3ccc(OCCC(C)(C)CO)cc3sc2=O)c(C(F)(F)F)c1] | 76% |

| | | |
|---|---|---|
| 7c | [structure: 7-(hydroxy-(CH2)11-O) thiochromene-2-thione with 3-aryl substituent bearing CF3 and pentyl] | 77% |
| 7d | [structure: 7-(HO-(CH2)8-O)-coumarin with 3-(2,4-di-sec-butylphenyl)] | 73% |
| 7e | [structure: 7-(HO-(CH2)12-O)-coumarin with 3-(2,4-diisopropylphenyl)] | 85% |
| 7f | [structure: 7-(HO-(CH2)12-O)-coumarin with 3-(2-ethyl-4-pentylphenyl)] | 50% |
| 7g | [structure: 7-(HO-(CH2)12-O)-coumarin with 3-(2,4-diethylphenyl)] | 63% |
| 7h | [structure: 7-(HO-(CH2)11-O)-coumarin with 3-(2-(trifluoromethyl)phenyl)] | 76% |
| 7i | [structure: 7-(HO-(CH2)12-O)-coumarin with 3-(2-(pentafluoroethyl)phenyl)] | 69% |

| | | |
|---|---|---|
| 7j | HO-(—)₁₂-O- [coumarin-2-one]-3-(2-(CF₃)-4-pentyl-phenyl) | 68% |
| 7k | HO-(—)₈-O- [coumarin-2-one]-3-(2-(CF₃)-4-pentyl-phenyl) | 69 |
| 7m | HO-(—)₁₁-O- [coumarin-2-one]-3-(4-butoxyphenyl) | 79% |
| 7n | HO-(—)₁₂-O- [coumarin-2-one]-3-(4-butoxyphenyl) | 99% |
| 7o | HO-(—)₁₂-O- [6-O-coumarin-2-one]-3-(2,6-diethylphenyl) | 52% |
| 7p | HO-(—)₁₂-O- [coumarin-2-thione]-3-(2,4-diethylphenyl) | 65% |
| 7q | HO-(—)₁₂-S- [coumarin-2-one]-3-(2-(CF₃)-4-chloro-phenyl) | 71% |
| 7r | HO-(—)₁₂-O- [coumarin-2-one]-3-(4-(OCF₃)phenyl) | 34% |

| | | |
|---|---|---|
| 7s | [structure: 7-(HO-(CH2)12-O)-2H-thiochromen-2-one with 3-(2-(trifluoromethyl)-4-pentylphenyl) substituent] | 79% |
| 7t | [structure: 7-(HO-(CH2)12-O)-coumarin with 3-(2-(trifluoromethyl)-4-pentylphenyl) substituent] | 77% |
| 7u | [structure: 7-(HO-(CH2)14-O)-coumarin with 3-(2-(trifluoromethyl)-4-pentylphenyl) substituent] | 83% |
| 7v | [structure: 7-(HO-(CH2)12-O)-coumarin with 3-(2-(trifluoromethoxy)phenyl) substituent] | 59% |
| 7w | [structure: 7-(HO-(CH2)12-O)-coumarin with 3-(2-(trifluoromethoxy)-4-pentylphenyl) substituent] | 92% |

Selected NMR data:

Product 7a—$^1$H NMR (500 MHz, DMSO-d$_6$) δ 8.10 (s, 1H), 7.86 (d, J=8.9 Hz, 1H), 7.47 (d, J=8.2 Hz, 2H), 7.27–7.23 (m, 3H), 7.08 (dd, J=8.7, 2.5 Hz, 1H), 4.29 (t, J=5.2 Hz, 1H), 4.10 (t, J=6.5 Hz, 2H), 3.42–3.34 (m, 2H), 2.62 (t, J=7.6 Hz, 2H), 1.75 (p, J=6.6 Hz, 2H), 1.61 (p, J=7.5 Hz, 2H), 1.42 (h, J=6.9 Hz, 4H), 1.37–1.20 (m, 16H), 0.88 (t, J=7.0 Hz, 3H).

Product 7f—$^1$H NMR (500 MHz, DMSO-d$_6$) δ 7.91 (s, 1H), 7.64 (d, J=8.7 Hz, 1H), 7.14 (s, 1H), 7.13 (d, J=7.8 Hz, 1H), 7.07 (d, J=7.7 Hz, 1H), 7.03 (d, J=2.2 Hz, 1H), 6.97 (dd, J=8.6, 2.4 Hz, 1H), 4.29 (t, J=5.1 Hz, 1H), 4.10 (t, J=6.5 Hz, 2H), 3.38 (q, J=6.5 Hz, 2H), 2.63–2.57 (m, 2H), 2.53–2.42 (m, 2H), 1.75 (p, J=6.6 Hz, 2H), 1.61 (p, J=7.4 Hz, 2H), 1.47–1.38 (m, 4H), 1.26 (s, 14H), 1.08 (t, J=7.5 Hz, 3H), 0.89 (t, J=6.9 Hz, 3H).

Product 7g—$^1$H NMR (500 MHz, DMSO-d$_6$) δ 7.91 (s, 1H), 7.64 (d, J=8.7 Hz, 1H), 7.16 (s, 1H), 7.14 (d, J=7.7 Hz, 1H), 7.09 (dd, J=7.8, 1.5 Hz, 1H), 7.03 (d, J=2.3 Hz, 1H), 6.98 (dd, J=8.6, 2.4 Hz, 1H), 4.29 (t, J=5.2 Hz, 1H), 4.10 (t, J=6.5 Hz, 2H), 3.41–3.34 (m, 2H), 2.64 (q, J=7.6 Hz, 2H), 2.54–2.45 (m, 2H), 1.78–1.72 (m, 2H), 1.47–1.37 (m, 4H), 1.37–1.25 (m, 14H), 1.22 (t, J=7.6 Hz, 3H), 1.08 (t, J=7.5 Hz, 3H).

Product 7h—$^1$H NMR (500 MHz, Chloroform-d) δ 7.68 (d, J=7.9 Hz, 1H), 7.54–7.48 (m, 2H), 7.43 (t, J=7.7 Hz, 1H), 7.33 (d, J=7.6 Hz, 1H), 7.31 (d, J=9.0 Hz, 1H), 6.81–6.76 (m, 2H), 3.96 (t, J=6.5 Hz, 2H), 3.59–3.51 (m, 2H), 1.79–1.70 (m, 2H), 1.49 (p, J=6.7 Hz, 2H), 1.40 (p, J=7.1 Hz, 2H), 1.33–1.19 (m, 12H).

Product 7i—$^1$H NMR (500 MHz, DMSO-d$_6$) δ 7.91 (s, 1H), 7.80–7.75 (m, 2H), 7.72 (d, J=7.4 Hz, 1H), 7.66 (d, J=8.7 Hz, 1H), 7.54 (t, J=7.5 Hz, 1H), 7.06 (d, J=2.2 Hz, 1H), 6.99 (dd, J=8.6, 2.4 Hz, 1H), 4.29 (t, J=5.2 Hz, 1H), 4.11 (t, J=6.5 Hz, 2H), 3.38 (q, J=6.5 Hz, 2H), 1.76 (p, J=6.6 Hz, 2H), 1.42 (dp, J=13.2, 6.9 Hz, 4H), 1.37–1.22 (m, 14H).

Product 7j—$^1$H NMR (500 MHz, DMSO-$d_6$) δ 7.94 (s, 1H), 7.66 (d, J=8.8 Hz, 1H), 7.64 (s, 1H), 7.57 (d, J=7.9 Hz, 1H), 7.44 (d, J=7.8 Hz, 1H), 7.05 (d, J=2.2 Hz, 1H), 6.98 (dd, J=8.6, 2.3 Hz, 1H), 4.29 (t, J=5.1 Hz, 1H), 4.10 (t, J=6.5 Hz, 2H), 3.38 (q, J=6.5 Hz, 2H), 2.75-2.67 (m, 2H), 1.75 (p, J=6.7 Hz, 2H), 1.64 (p, J=7.4 Hz, 2H), 1.46-1.39 (m, 4H), 1.37-1.23 (m, 18H), 0.89 (t, J=6.9 Hz, 3H).

Product 7k—$^1$H NMR (500 MHz, DMSO-$d_6$) δ 7.87 (s, 1H), 7.58 (d, J=8.7 Hz, 1H), 7.56 (s, 1H), 7.50 (d, J=8.5 Hz, 1H), 7.36 (d, J=7.9 Hz, 1H), 6.98 (d, J=2.3 Hz, 1H), 6.91 (dd, J=8.6, 2.4 Hz, 1H), 4.22 (s, 1H), 4.03 (t, J=6.5 Hz, 2H), 3.31 (t, J=6.5 Hz, 2H), 2.68-2.60 (m, 2H), 1.68 (p, J=6.6 Hz, 2H), 1.56 (p, J=7.5 Hz, 2H), 1.42-1.32 (m, 4H), 1.32-1.18 (m, 10H), 0.82 (t, J=7.0 Hz, 3H).

Product 7n—$^1$H NMR (500 MHz, DMSO-$d_6$) δ 8.13 (s, 1H), 7.68-7.65 (m, 3H), 7.02-6.99 (m, 3H), 6.97 (dd, J=8.6, 2.4 Hz, 1H), 4.29 (s, 1H), 4.09 (t, J=6.5 Hz, 2H), 4.03 (t, J=6.5 Hz, 2H), 3.38 (t, J=6.6 Hz, 2H), 1.79-1.69 (m, 4H), 1.53-1.37 (m, 6H), 1.36 -1.22 (m, 14H), 0.96 (t, J=7.4 Hz, 3H).

Product 7q—$^H$NMR (500 MHz, Chloroform-d) δ 7.78 (d, J=1.9 Hz, 1H), 7.62 (dd, J=8.0, 1.8 Hz, 1H), 7.61 (s, 1H), 7.40 (d, J=8.1 Hz, 2H), 7.23 (s, 1H), 7.19 (dd, J=8.2, 1.5 Hz, 1H), 3.67 (q, J=6.4 Hz, 2H), 3.03 (t, J=7.4 Hz, 2H), 1.76 (p, J=7.5 Hz, 2H), 1.60 (p, J=7.2 Hz, 2H), 1.49 (p, J=7.2 Hz, 2H), 1.38-1.27 (m, 14H).

Product 7r—$^1$H NMR (500 MHz, Chloroform-d) δ 7.79 (s, 1H), 7.76 (d, J=8.7 Hz, 2H), 7.46 (d, J=8.6 Hz, 1H), 7.30 (d, J=8.6 Hz, 2H), 6.90 (dd, J=8.6, 2.3 Hz, 1H), 6.87 (d, J=2.1 Hz, 1H), 4.06 (t, J=6.5 Hz, 2H), 3.67 (t, J=6.6 Hz, 2H), 1.85 (p, J=6.7 Hz, 2H), 1.59 (p, J=6.7 Hz, 2H), 1.50 (p, J=7.1 Hz, 2H), 1.44-1.21 (m, 14H).

Product 7s—$^1$H NMR (500 MHz, DMSO-$d_6$) δ 6 7.96 (s, 1H), 7.81 (d, J=8.9 Hz, 1H), 7.65-7.61 (m, 1H), 7.56 (d, J=7.5 Hz, 1H), 7.37 (d, J=7.8 Hz, 1H), 7.30 (d, J=2.4 Hz, 1H), 7.09 (dd, J=8.7, 2.5 Hz, 1H), 4.31 (t, J=5.2 Hz, 1H), 4.11 (t, J=6.5 Hz, 2H), 3.40-3.35 (m, 2H), 2.77-2.68 (m, 2H), 1.75 (p, J=6.6 Hz, 2H), 1.63 (p, J=7.5 Hz, 2H), 1.45-1.38 (m, 4H), 1.37-1.31 (m, 4H), 1.30-1.23 (m, 14H), 0.89 (t, J=7.0 Hz, 3H).

Product 7u—$^1$H NMR (500 MHz, DMSO-$d_6$) δ 7.94 (s, 1H), 7.66 (d, J=8.7 Hz, 1H), 7.64 (d, J=1.2 Hz, 1H), 7.57 (d, J=8.0 Hz, 1H), 7.43 (d, J=7.8 Hz, 1H), 7.05 (d, J=2.3 Hz, 1H), 6.98 (dd, J=8.6, 2.4 Hz, 1H), 4.29 (t, J=5.2 Hz, 2H), 4.10 (t, J=6.5 Hz, 2H), 3.42-3.35 (m, 2H), 2.75-2.67 (m, 2H), 1.75 (p, J=6.6 Hz, 2H), 1.64 (p, J=7.5 Hz, 2H), 1.45-1.23 (m, 24H), 0.89 (t, J=7.0 Hz, 3H).

Product 7v—$^1$H NMR (500 MHz, DMSO-$d_6$) δ 8.10 (s, 1H), 7.69 (d, J=8.7 Hz, 1H), 7.62-7.55 (m, 2H), 7.53-7.45 (m, 2H), 7.06 (d, J=2.3 Hz, 1H), 7.00 (dd, J=8.6, 2.4 Hz, 1H), 4.11 (t, J=6.5 Hz, 2H), 3.38 (t, J=6.6 Hz, 2H), 1.81-1.70 (m, 4H), 1.51-1.37 (m, 4H), 1.37-1.22 (m, 12H).

Product 7w—$^1$H NMR (500 MHz, Chloroform-d) δ 7.70 (s, 1H), 7.43 (d, J=7.8 Hz, 1H), 7.42 (d, J=8.5 Hz, 1H), 7.22-7.16 (m, 2H), 6.92-6.87 (m, 2H), 4.06 (t, J=6.5 Hz, 2H), 3.67 (td, J=6.4, 3.8 Hz, 2H), 2.71-2.65 (m, 2H), 1.85 (p, J=6.6 Hz, 2H), 1.67 (pi, J=7.5 Hz, 2H), 1.50 (p, J=7.0 Hz, 2H), 1.44-1.28 (m, 20H), 0.94 (t, J=6.9 Hz, 3H).

Example 8

7-[((-Octa-4,7-dienyl)oxy]-3-(4-pentyl-phenyl)-coumarin

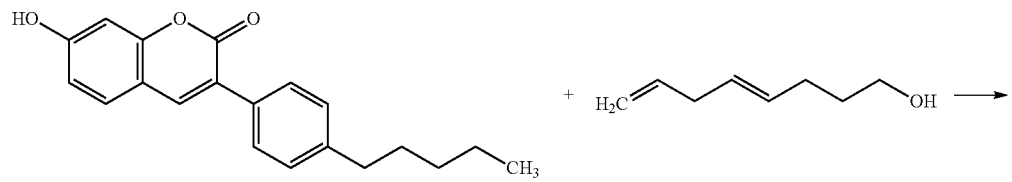

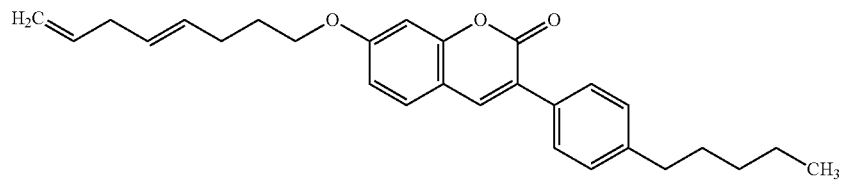

To an ice-cooled solution of 2.8 g (8.1 mmol) 7-Hydroxy-3-(4-pentyl-phenyl)-coumarin, 1.0 g (4E)-Octa-4,7-dien-1-ol (8.1 mmol), 2.4 g (11.6 mmol) triphenylphosphine in THF (18 ml), 2.32 ml (11.6 mmol) diisopropyl azodicarboxylate is added dropwise. After stirring at room temperature overnight, the reaction mixture was evaporated. The crude product is purified by column chromatography to give 2.25 g of 7-[((E)-Octa-4,7-dienyl)oxy]-3-(4-pentyl-phenyl)-coumarin (6.50 mmol, 67% of theory) as a white solid. For further purification, the product was recrystallized in EtOH.

$^1$H NMR (500 MHz, DMSO-$d_6$) δ 8.21 (s, 1H), 7.72 (d, J=7.2 Hz, 2H), 7.70 (d, J=8.6 Hz, 1H), 7.46 (t, J=7.4 Hz, 2H), 7.02 (d, J=2.3 Hz, 1H), 6.99 (dd, J=8.6, 2.4 Hz, 1H), 5.82 (ddt, J=16.7, 10.1, 6.4 Hz, 1H), 5.59-5.36 (m, 2H), 5.02 ($d_q$, J=17.2, 1.7 Hz, 1H), 4.98 (dq, J=10.1, 1.3 Hz, 1H), 4.10 (t, J=6.4 Hz, 2H), 2.75 (t, J=5.7 Hz, 2H), 2.61 (t, J=7.6 Hz, 2H) 2.17 (q, J=6.4, 5.9 Hz, 2H), 1.83 (p, J=6.5 Hz, 2H), 1.60 (p, J=7.5 Hz, 2H), 1.31-1.24 (m, 4H), 0.83 (t, J=6.7 Hz, 3H).

Example 9

7-((E)-8-Hydroxy-oct-4-enyloxy)-3-(4-pentyl-phenyl)-coumarin

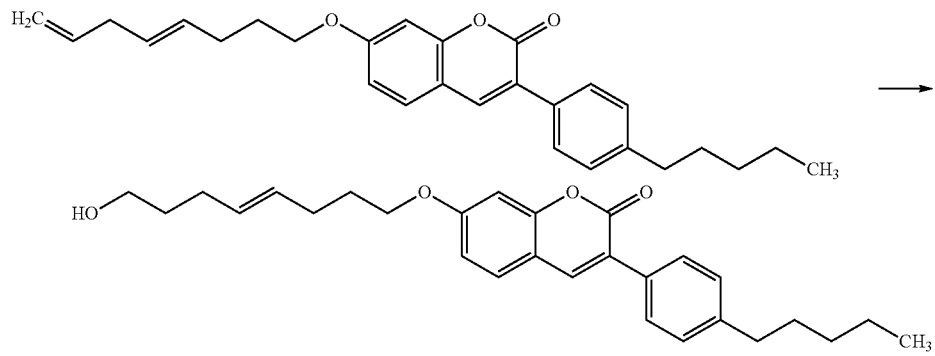

A Schlenk flask is charged with THF (0.5 ml) and 100 mg (0.24 mmol) 7-[((E)-octa-4,7-dienyl)oxy]-3-(4-pentyl-phenyl)-coumarin. The solution is cooled to 0° C. After 10 min, 0.48 ml (0.24 mmol) 9-BBN (0.5 M in THF) is added dropwise via syringe over 30 min. The reaction is stirred for 1 h at 0° C., then 1 h at 25° C. 0.34 ml (0.69 mmol) NaOH (aq, 2M) is added and the reaction cooled to 0° C. 0.20 ml (1.97 mmol) H2O2 (30% in water) is added dropwise over 10 min. The reaction is diluted with Et2O, filtered through Celite. The organic filtrate is concentrated to give 53 mg (0.15 mmol) crude 7-((E)-8-hydroxy-oct-4-enyloxy)-3-(4-pentyl-phenyl)-coumarin 50% of theory).

$^1$H NMR (500 MHz, DMSO-d$_6$) δ 8.21 (s, 1H), 7.72 (d, J=7.4 Hz, 2H), 7.70 (d, J=8.7 Hz, 1H), 7.46 (t, J=7.5 Hz, 2H), 7.02 (d, J=2.2 Hz, 1H), 6.99 (dd, J=8.6, 2.3 Hz, 1H), 5.47 (dd, J=4.5, 2.9 Hz, 2H), 4.33 (t, J=5.2 Hz, 1H), 4.10 (t, J=6.4 Hz, 2H), 3.46-3.35 (m, 2H), 2.61 (t, J=7.6 Hz, 2H), 2.18-2.11 (m, 2H), 2.06-1.96 (m, 2H), 1.87-1.76 (m, 2H), 1.68 (p, J=6.8 Hz, 2H), 1.55-1.41 (m, 2H), 1.31-1.24 (m, 4H), 0.83 (t, J=6.7 Hz, 3H).

Example 10

2-[11-(4,4,5,5-Tetrannethyl-[1,3,2]clioxaborolan-2-yl)-undecyloxyl-tetrahydro-pyran

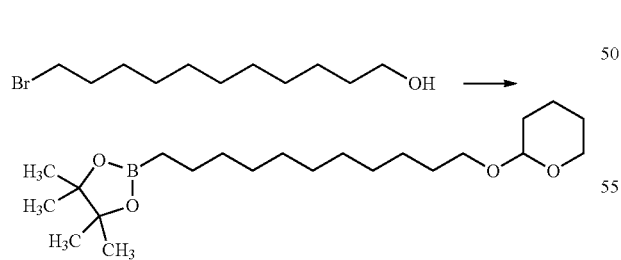

12 g (46 mmol) 11-Bromo-undecan-1-ol and 4.6 ml (51 mmol) 3,4-Dihydropyran in 45 ml THF are treated with 400 mg (2.32 mmol) p-toluenesulfonic acid and stirred overnight. The reaction mixture was filtered and washed with THF. The solvent was evaporated. The residual oil (9.6 g; 28.7 mmol), 547 mg (2.87 mmol), 1.1 mg (4.3 mmol) triphenylphosphine and 10.94 g (43.08 mmol) bis-(pinacolato)-diboron were added to a Schlenk tube equipped with a stir bar. The vessel was evacuated and filled with argon (three cycles). DMF (55.8 ml) was added under argon atmosphere. The resulting reaction mixture was stirred vigorously at 25° C. for 18 h. The reaction mixture was then diluted with EtOAc, filtered through silica gel with copious washings (EtOAc), concentrated, and purified by column chromatography. 2-[11-(4,4,5,5-Tetrannethyl-[1,3,2]dioxaborolan-2-yl)-undecyloxy]-tetrahydro-pyran (7.66 g; 16.00 mmol) was received as oil, 55.7% of theory.

$^1$H NMR (500 MHz, DMSO-d$_6$) δ 4.53 (dd, J=4.4, 2.8 Hz, 2H), 3.73 (ddd, J=11.2, 8.1, 3.1 Hz, 2H), 3.60 (dt, J=9.7, 6.7 Hz, 2H), 3.46-3.37 (m, 2H), 3.35-3.30 (m, 2H), 1.77-1.67 (m, 2H), 1.64-1.57 (m, 2H), 1.54-1.41 (m, 9H), 1.36-1.22 (m, 8H), 1.18 (s, 12H).

Example 11

3-(2-trifluoromethyl-phenyl)-7-(11-hydroxy-undecyl)-coumarin

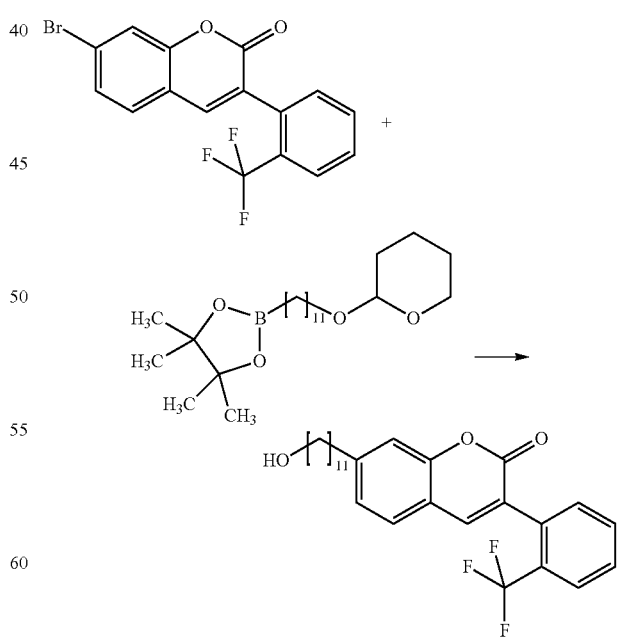

155 mg (0.4 mmol) 7-Bromo-3-(2-trifluoromethyl-phenyl)-coumarin, 167 mg (0.4 mmol) 2411-(4,4,5,5-Tetramethyl-[1,3,2]clioxa borola n-2-yl)-undecyloxyl-tetrahydropyran, 120 mg (1.3 mmol) sodium tert-butylate and 12 mg (0.02 mmol) bis(dibenzylideneacetone)palladium(0) are added to a flask equipped with a stirbar. Degassed toluene (2.9 ml) is then added. The reaction vessel is heated to 100° C. for 24 h. The cooled reaction mixture is filtered and washed thoroughly with diluted HCl. The organic phase is concentrated under reduced pressure, and purified by column chromatography. 63 mg (0.1 mmol; 32% of theory) 3-(2-trifluoromethyl-phenyl)-7-(11-hydroxy-undecyl)-coumarin are isolated.

Example 12

Acrylic acid 11-[2-oxo-3-(4-pentyl-phenyl)-coumarin-7-yloxy]-undecyl ester

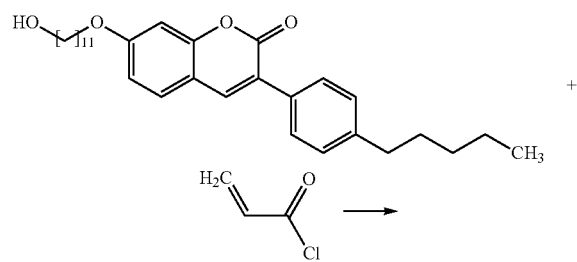

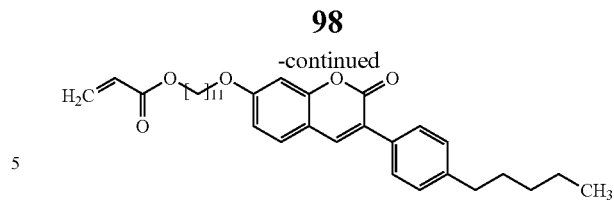

Acryloyl chloride (0.3 ml; 3.5 mmol) is slowly added to an ice-cooled solution of 1.4 g (2.9 mmol) 7-(11-hydroxy-undecyloxy)-3-(4-pentyl-phenyl)-coumarin in dry 10 ml THF and 1.6 ml (11.7 mmol) triethylamine. Afterwards, the reaction is stirred for 2 h at room temperature. The solid which has precipitated out is filtered off with suction and the filtrate is concentrated under reduced pressure. The residue is purified by column chromatography. 1.1 g (2.1 mmol; 71% of theory) Acrylic acid 11-[2-oxo-3-(4-pentyl-phenyl)-coumarin-7-yloxy]-undecyl ester are isolated.

$^1$H NMR (500 MHz, Chloroform-d) δ 7.64 (s, 1H), 7.52 (d, J=8.2 Hz, 2H), 7.31 (d, J=8.4 Hz, 1H), 7.15 (d, J=8.3 Hz, 2H), 6.78-6.75 (m, 1H), 6.74 (d, J=2.2 Hz, 1H), 6.31 (dd, J=17.4, 1.5 Hz, 1H), 6.04 (dd, J=17.3, 10.4 Hz, 1H), 5.72 (dd, J=10.3, 1.5 Hz, 1H), 4.07 (t, J=6.8 Hz, 2H), 3.93 (t, J=6.5 Hz, 2H), 2.58-2.43 (m, 2H), 1.73 (dt, J=14.5, 6.6 Hz, 2H), 1.58 (dq, J=15.4, 8.1, 7.4 Hz, 4H), 1.39 (p, J=7.0 Hz, 2H), 1.30-1.21 (m, 16H), 0.82 (t, J=6.9 Hz, 3H).

The following compounds 12a to 12z are prepared analogously:

| | Reactant 1 | Reactant 2 |
|---|---|---|
| 12a | ![structure] 7-(11-hydroxyundecyloxy)-3-(4-pentyl-phenyl)-coumarin | methacryloyl chloride |
| 12b | ![structure] 7-(11-hydroxyundecyloxy)-3-(4-pentyl-phenyl)-thiocoumarin (S in ring) | acryloyl chloride |
| 12c | ![structure] 3,3-dimethyl-4-hydroxybutyloxy thiocoumarin with 2-(trifluoromethyl)-4-pentyl-phenyl | acryloyl chloride |
| 12d | ![structure] 7-(11-hydroxyundecyloxy)-3-[2-(trifluoromethyl)-4-pentyl-phenyl]-thiocoumarin-2-thione | acryloyl chloride |

-continued
| | | |
|---|---|---|
| 12e | 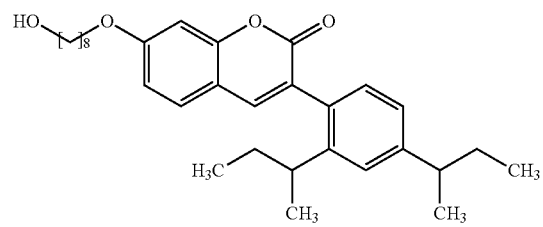 | 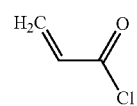 |
| 12f | 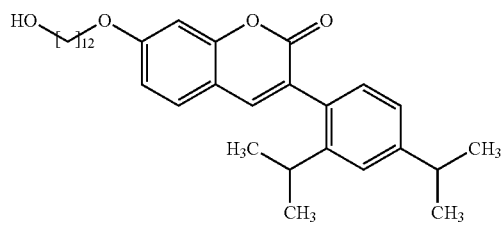 | 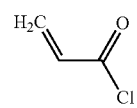 |
| 12g | 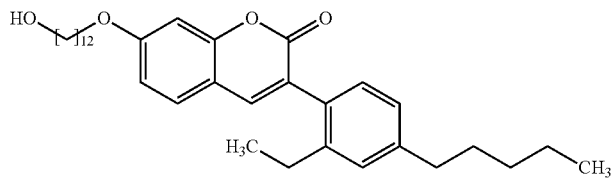 | 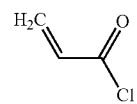 |
| 12h | 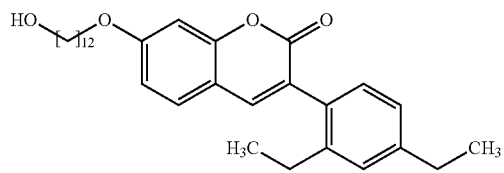 | 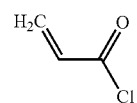 |
| 12i | 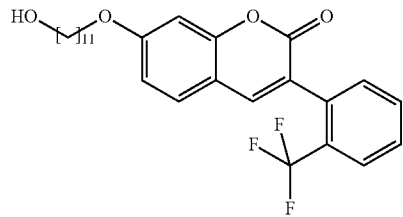 | 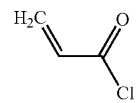 |
| 12j | 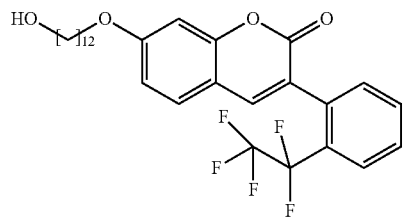 | 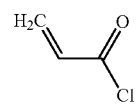 |
| 12k | 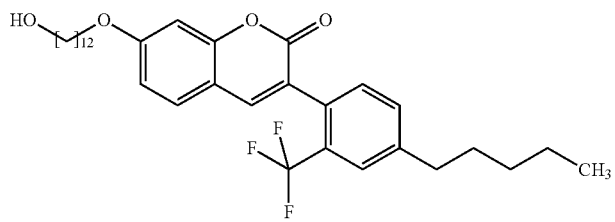 | 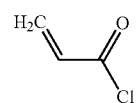 |

| | 101 | 102 |
|---|---|---|
| | -continued | |
| 12l | 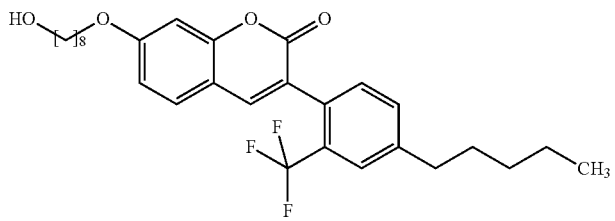 | 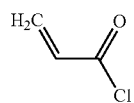 |
| 12m | 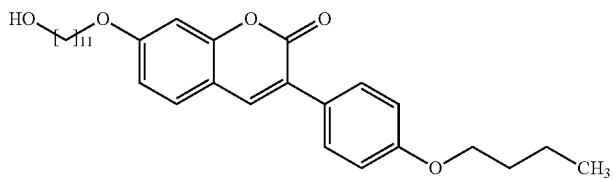 | 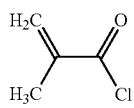 |
| 12n | 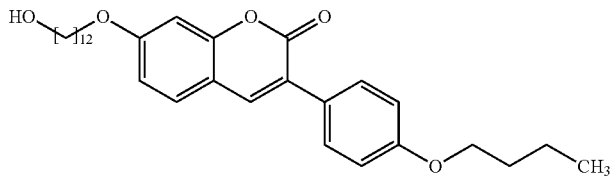 | 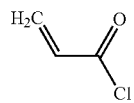 |
| 12o | 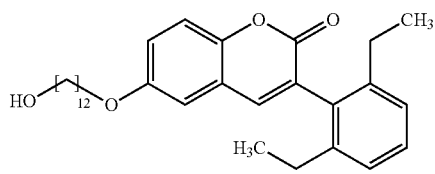 | 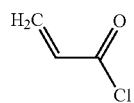 |
| 12p | 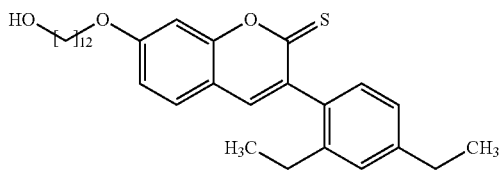 | 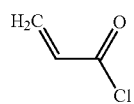 |
| 12q | 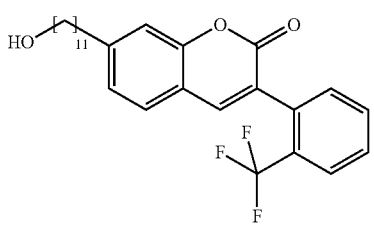 | 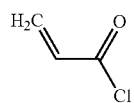 |
| 12r | 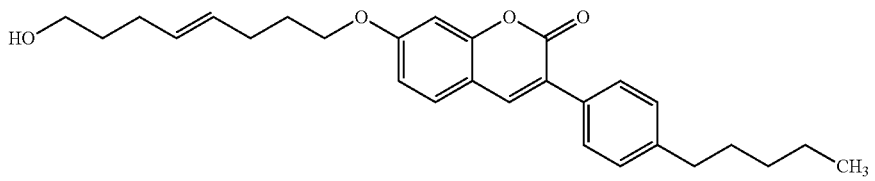 [SMILES: CCCCCc1ccc(-c2cc3ccc(OCCC/C=C/CCCO)cc3oc2=O)cc1] | 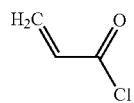 |
| 12s | 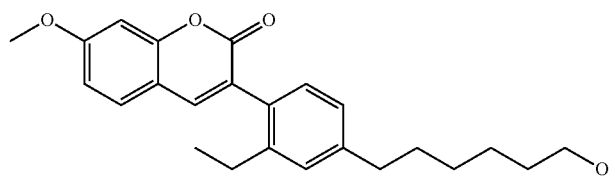 [SMILES: CCc1cc(CCCCCCO)ccc1-c1cc2ccc(OC)cc2oc1=O] | 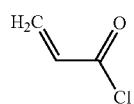 |

-continued
| | | |
|---|---|---|
| 12t | 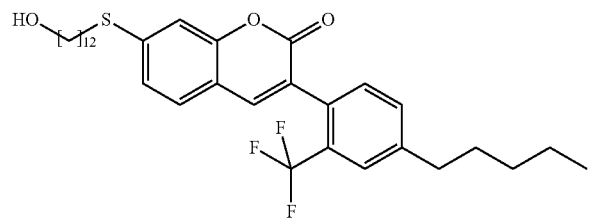 | 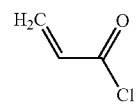 |
| 12u | 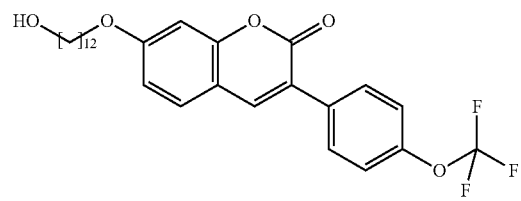 | 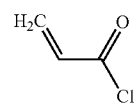 |
| 12v | 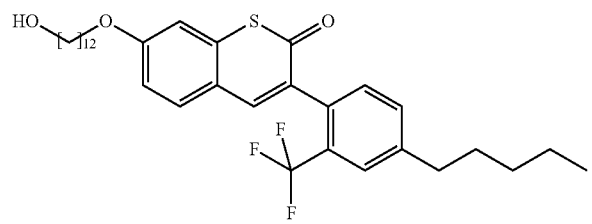 | 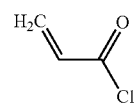 |
| 12w | 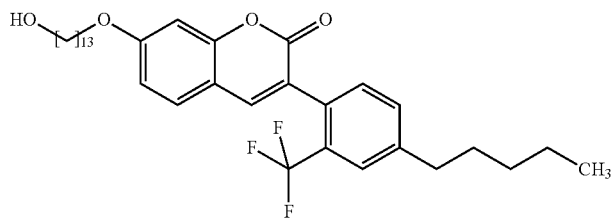 | 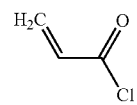 |
| 12x | 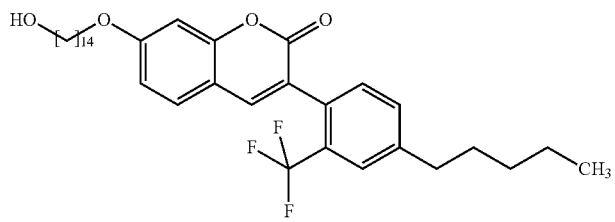 | 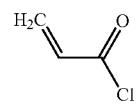 |
| 12y | 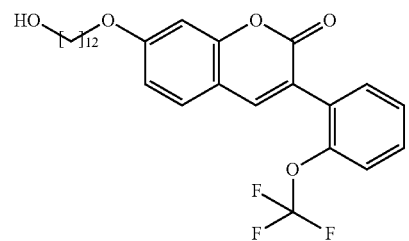 | 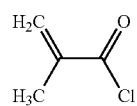 |
| 12z | 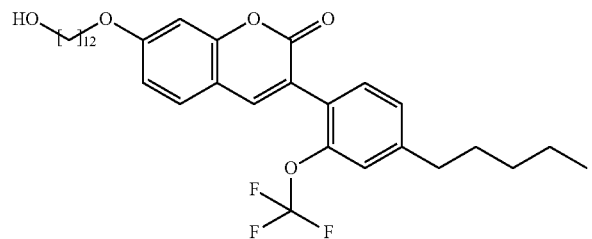 | 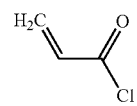 |

-continued

| | Product | Yield |
|---|---|---|
| 12a | methacrylate-O-(CH₂)₁₁-O-[7-coumarin-2-one]-3-(4-pentylphenyl) | 77% |
| 12b | acrylate-O-(CH₂)₁₁-O-[7-thiocoumarin-2-one]-3-(4-pentylphenyl) | 54% |
| 12c | acrylate-O-CH₂-C(CH₃)₂-CH₂-CH₂-O-[7-thiocoumarin-2-one]-3-(2-trifluoromethyl-4-pentylphenyl) | 70% |
| 12d | acrylate-O-(CH₂)₁₁-O-[7-thiocoumarin-2-thione]-3-(2-trifluoromethyl-4-pentylphenyl) | 91% |
| 12e | acrylate-O-(CH₂)₈-O-[7-coumarin-2-one]-3-(2,4-di-sec-butylphenyl) | 67% |
| 12f | acrylate-O-(CH₂)₁₂-O-[7-coumarin-2-one]-3-(2,4-diisopropylphenyl) | 75% |
| 12g | acrylate-O-(CH₂)₁₂-O-[7-coumarin-2-one]-3-(2-ethyl-4-pentylphenyl) | 66% |

-continued
| | | |
|---|---|---|
| 12h | 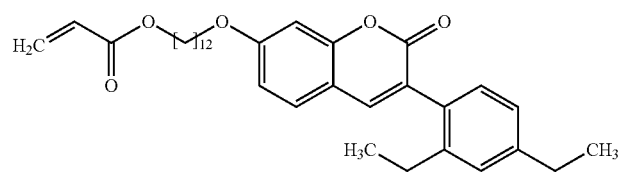 | 84% |
| 12i | 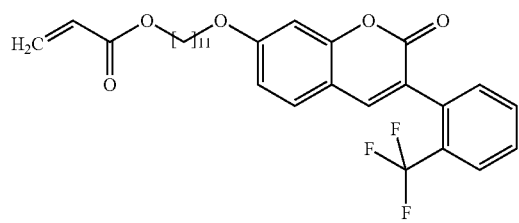 | 81% |
| 12j | 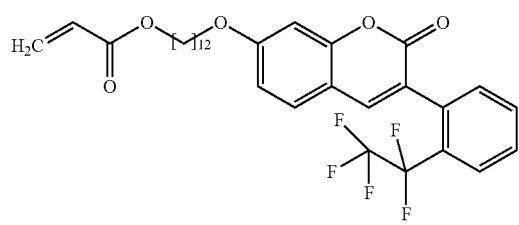 | 59% |
| 12k | 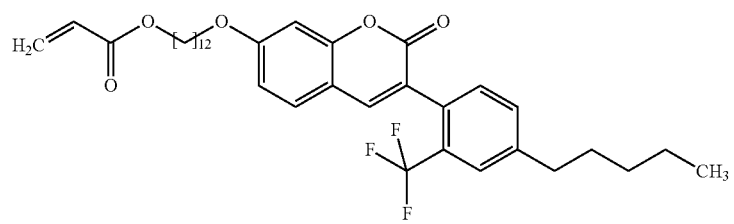 | 75% |
| 12l | 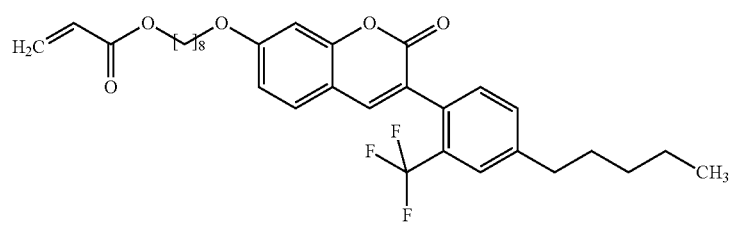 | 60% |
| 12m | 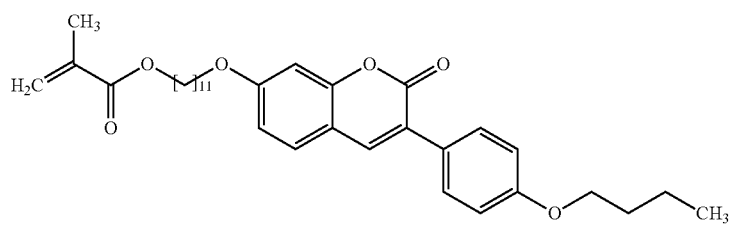 | 77% |
| 12n | 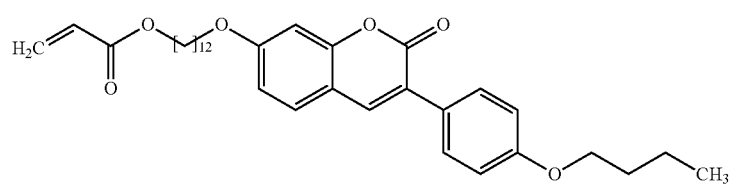 | 59% |

-continued
| | | |
|---|---|---|
| 12o | 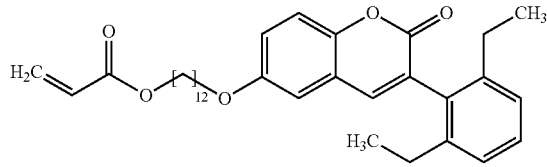 | 86% |
| 12p | 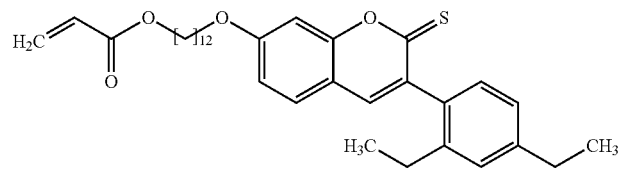 | 74% |
| 12q | 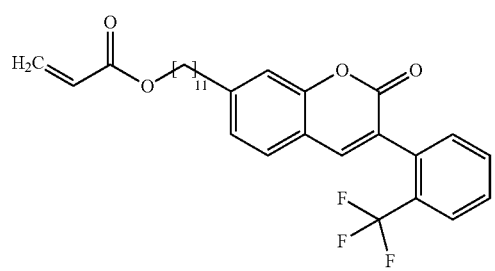 | 88% |
| 12r | 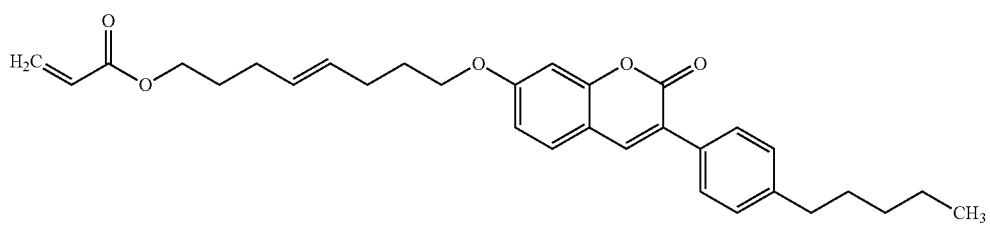 [SMILES: C=CC(=O)OCCC/C=C/CCCOc1ccc2cc(-c3ccc(CCCCC)cc3)c(=O)oc2c1] | 97% |
| 12s | 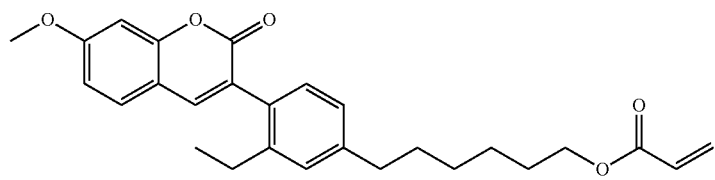 [SMILES: C=CC(=O)OCCCCCCc1ccc(-c2cc3ccc(OC)cc3oc2=O)c(CC)c1] | 57% |
| 12t | 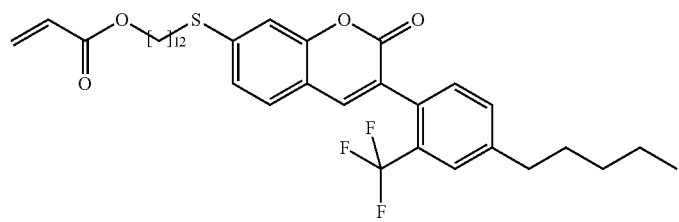 | 34% |
| 12u | 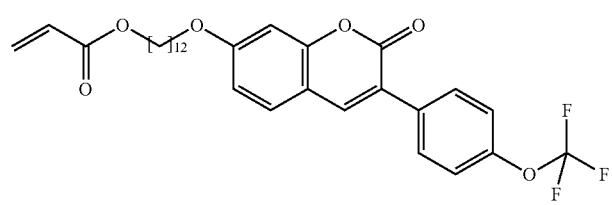 | 76% |

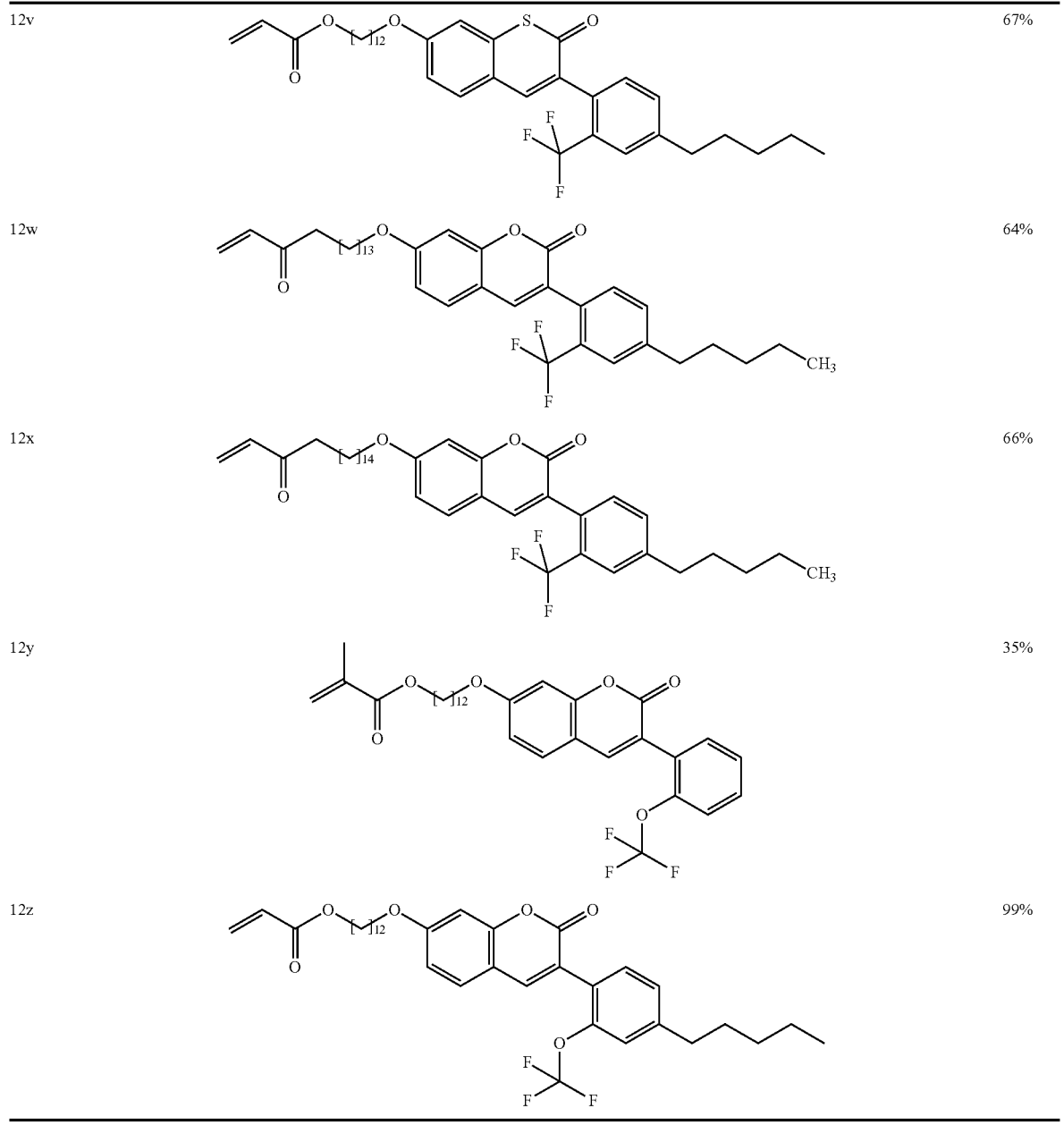

Selected NMR data

Product 12a—$^1$H NMR (500 MHz, Chloroform-d) δ 7.66 (s, 1H), 7.54 (d, J=8.2 Hz, 2H), 7.33 (d, J=8.3 Hz, 1H), 7.17 (d, J=8.2 Hz, 2H), 6.79 (d, J=8.2, 2.4 Hz, 1H), 6.77 (s, 1H), 6.02 (s, 1H), 5.47 (s, 1H), 4.07 (t, J=6.7 Hz, 2H), 3.95 (t, J=6.5 Hz, 2H), 2.60–2.51 (m, 2H), 1.87 (s, 3H), 1.75 (dt, J=14.5, 6.6 Hz, 2H), 1.59 (dp, J=15.7, 7.1 Hz, 4H), 1.40 (p, J=7.0 Hz, 2H), 1.34–1.18 (m, 16H), 0.85–0.82 (m, 3H).

Product 12b—$^1$H NMR (500 MHz, DMSO-d$_6$) δ 8.10 (s, 1H), 7.86 (d, J=8.8 Hz, 1H), 7.47 (d, J=8.2 Hz, 2H), 7.26 (d, J=8.2 Hz, 2H), 7.25 (d, J=2.5 Hz, 1H), 7.08 (dd, J=8.7, 2.5 Hz, 1H), 6.32 (dd, J=17.3, 1.6 Hz, 1H), 6.17 (dd, J=17.3, 10.3 Hz, 1H), 5.93 (dd, J=10.3, 1.6 Hz, 1H), 4.10 (t, J=6.6 Hz, 4H), 2.62 (t, J=7.6 Hz, 2H), 1.75 (p, J=6.6 Hz, 2H), 1.61 (p, J=7.7, 7.0 Hz, 4H), 1.43 (p, J=6.8 Hz, 2H), 1.36–1.24 (m, 16H), 0.88 (t, J=7.0 Hz, 3H).

Product 12g—$^1$H NMR (500 MHz, DMSO-d$_6$) δ 7.91 (s, 1H), 7.64 (d, J=8.7 Hz, 1H), 7.14 (s, 1H), 7.12 (d, J=7.8 Hz, 1H), 7.07 (dd, J=7.8, 1.4 Hz, 1H), 7.03 (d, J=2.3 Hz, 1H), 6.97 (dd, J=8.6, 2.4 Hz, 1H), 6.32 (dd, J=17.3, 1.5 Hz, 1H), 6.17 (dd, J=17.3, 10.3 Hz, 1H), 5.93 (dd, J=10.3, 1.5 Hz, 1H), 4.10 (t, J=6.6 Hz, 4H), 2.64-2.57 (m, 2H), 2.52–2.45 (m, 2H), 1.75 (p, J=6.7 Hz, 2H), 1.60 (q, J=6.3 Hz, 4H), 1.43 (p, J=6.7 Hz, 2H), 1.37–1.26 (m, 20H), 1.08 (t, J=7.5 Hz, 3H), 0.89 (t, J=6.9 Hz, 3H).

Product 12h—$^1$H NMR (500 MHz, DMSO-d$_6$) δ 7.91 (s, 1H), 7.64 (d, J=8.7 Hz, 1H), 7.16 (s, 1H), 7.13 (d, J=7.7 Hz, 1H), 7.09 (dd, J=7.8, 1.5 Hz, 1H), 7.03 (d, J=2.3 Hz, 1H), 6.98 (dd, J=8.6, 2.4 Hz, 1H), 6.32 (dd, J=17.3, 1.6 Hz, 1H), 6.17 (dd, J=17.3, 10.3 Hz, 1H), 5.93 (dd, J=10.3, 1.6 Hz, 1H), 4.10 (t, J=6.6 Hz, 4H), 2.64 (q, J=7.6 Hz, 2H), 2.51–2.47 (m, 2H), 1.75 (p, J=6.7 Hz, 2H), 1.61 (p, J=6.7

Hz, 2H), 1.43 (p, J=7.0 Hz, 2H), 1.36–1.25 (m, 14H), 1.22 (t, J=7.6 Hz, 3H), 1.08 (t, J=7.5 Hz, 3H).

Product 12i—¹H NMR (500 MHz, Chloroform-d) δ 7.69 (d, J=7.9 Hz, 1H), 7.53 (t, J=7.5 Hz, 1H), 7.50 (s, 1H), 7.45 (t, J=7.7 Hz, 1H), 7.35 (d, J=7.6 Hz, 1H), 7.32 (d, J=9.3 Hz, 1H), 6.80–6.78 (m, 2H), 6.32 (dd, J=17.4, 1.5 Hz, 1H), 6.05 (dd, J=17.3, 10.4 Hz, 1H), 5.74 (dd, J=10.4, 1.5 Hz, 1H), 4.08 (t, J=6.8 Hz, 2H), 3.97 (t, J=6.5 Hz, 2H), 1.80–1.72 (m, 2H), 1.67–1.55 (m, 2H), 1.41 (p, J=7.1 Hz, 2H), 1.34–1.21 (m, 12H).

Product 12j—¹H NMR (500 MHz, DMSO-d₆) δ 7.91 (s, 1H), 7.82-7.74 (m, 2H), 7.71 (t, J=7.7 Hz, 1H), 7.66 (d, J=8.7 Hz, 1H), 7.54 (d, J=7.4 Hz, 1H), 7.06 (d, J=2.3 Hz, 1H), 6.99 (dd, J=8.6, 2.4 Hz, 1H), 6.32 (dd, J=17.3, 1.6 Hz, 1H), 6.17 (dd, J=17.3, 10.3 Hz, 1H), 5.93 (dd, J=10.3, 1.6 Hz, 1H), 4.10 (td, J=6.5, 3.3 Hz, 4H), 1.75 (p, J=6.6 Hz, 2H), 1.61 (p, J=6.7 Hz, 2H), 1.43 (p, J=7.8, 7.1 Hz, 2H), 1.37–1.23 (m, 14H).

Product 12k—¹H NMR (500 MHz, DMSO-d₆) δ 7.94 (s, 1H), 7.65 (d, J=8.7 Hz, 1H), 7.64 (s, 1H), 7.57 (d, J=7.9 Hz, 1H), 7.43 (d, J=7.8 Hz, 1H), 7.04 (d, J=2.3 Hz, 1H), 6.98 (dd, J=8.6, 2.4 Hz, 1H), 6.31 (dd, J=17.3, 1.6 Hz, 1H), 6.16 (dd, J=17.3, 10.3 Hz, 1H), 5.92 (dd, J=10.3, 1.6 Hz, 1H), 4.10 (t, J=6.7 Hz, 4H), 2.76–2.68 (m, 2H), 1.75 (p, J=6.6 Hz, 2H), 1.68–1.56 (m, 4H), 1.43 (p, J=6.9 Hz, 2H), 1.38–1.22 (m, 20H), 0.89 (t, J=7.0 Hz, 3H).

Product 12m—¹H NMR (500 MHz, DMSO-d₆) δ 8.13 (s, 1H), 7.66 (m, 3H), 7.04–6.93 (m, 4H), 6.01 (s, 1H), 5.66 (s, 1H), 4.09 (t, J=6.6 Hz, 4H), 4.02 (t, J=6.5 Hz, 2H), 1.88 (s, 3H), 1.73 (q, J=8.1, 7.6 Hz, 4H), 1.64–1.58 (m, 2H), 1.50–1.40 (m, 4H), 1.29 (d, J=11.6 Hz, 12H), 0.96 (t, J=7.4 Hz, 3H).

Product 12n—¹H NMR (500 MHz, Chloroform-d) δ 7.62 (s, 1H), 7.56 (d, J=8.7 Hz, 2H), 7.32 (d, J=8.3 Hz, 1H), 6.87 (d, J=8.7 Hz, 2H), 6.80–6.72 (m, 2H), 6.32 (dd, J=17.4, 1.6 Hz, 1H), 6.05 (dd, J=17.3, 10.4 Hz, 1H), 5.73 (dd, J=10.4, 1.6 Hz, 1H), 4.08 (t, J=6.7 Hz, 2H), 3.94 (q, J=6.5 Hz, 4H), 1.73 (tt, J=14.7, 6.6 Hz, 4H), 1.59 (p, J=6.8 Hz, 2H), 1.48–1.35 (m, 4H), 1.34–1.17 (m, 14H), 0.91 (t, J=7.4 Hz, 3H).

Product 12s—¹H NMR (500 MHz, DMSO-d₆) δ 7.92 (s, 1H), 7.66 (d, J=8.6 Hz, 1H), 7.14 (s, 1H), 7.13 (d, J=7.9 Hz, 1H), 7.07 (dd, J=7.7, 1.1 Hz, 1H), 7.06 (d, J=2.3 Hz, 1H), 6.99 (dd, J=8.6, 2.4 Hz, 1H), 6.33 (dd, J=17.3, 1.5 Hz, 1H), 6.18 (dd, J=17.3, 10.3 Hz, 1H), 5.94 (dd, J=10.3, 1.5 Hz, 1H), 4.12 (t, J=6.6 Hz, 2H), 3.89 (s, 3H), 2.61 (t, J=7.7 Hz, 2H), 2.51–2.47 (m, 2H), 1.66–1.58 (m, 4H), 1.40–1.36 (m, 4H), 1.08 (t, J=7.5 Hz, 3H).

Product 12t—¹H NMR (500 MHz, Chloroform-d) δ 7.59 (s, 1H), 7.58 (s, 1H), 7.44 (d, J=7.5 Hz, 1H), 7.38 (d, J=8.2 Hz, 1H), 7.33 (d, J=7.8 Hz, 1H), 7.24 (d, J=1.4 Hz, 1H), 7.18 (dd, J=8.2, 1.7 Hz, 1H), 6.42 (dd, J=17.4, 1.5 Hz, 1H), 6.14 (dd, J=17.3, 10.4 Hz, 1H), 5.83 (dd, J=10.4, 1.4 Hz, 1H), 4.18 (t, J=6.8 Hz, 2H), 3.03 (t, J=7.4 Hz, 2H), 2.79–2.64 (m, 2H), 1.76 (p, J=7.6 Hz, 2H), 1.69 (p, J=6.9 Hz, 4H), 1.49 (p, J=7.3 Hz, 2H), 1.39 (p, J=3.6 Hz, 4H), 1.33–1.28 (m, 14H), 0.97–0.92 (m, 3H).

Product 12u—¹H NMR (500 MHz, Chloroform-d) δ 7.79 (s, 1H), 7.76 (d, J=8.8 Hz, 2H), 7.45 (d, J=8.6 Hz, 1H), 7.30 (d, J=8.2 Hz, 2H), 6.90 (dd, J=8.5, 2.4 Hz, 1H), 6.87 (d, J=2.2 Hz, 1H), 6.42 (dd, J=17.3, 1.4 Hz, 1H), 6.15 (dd, J=17.3, 10.4 Hz, 1H), 5.83 (dd, J=10.4, 1.4 Hz, 1H), 4.18 (t, J=6.8 Hz, 2H), 4.06 (t, J=6.5 Hz, 2H), 1.70 (p, J=6.8 Hz, 2H), 1.50 (p, J=7.0 Hz, 2H), 1.43–1.28 (m, 16H).

Product 12v—¹H NMR (500 MHz, Chloroform-d) δ 7.59 (s, 1H), 7.57 (s, 1H), 7.51 (d, J=8.6 Hz, 1H), 7.41 (d, J=7.8 Hz, 1H), 7.27 (d, J=7.8 Hz, 1H), 6.98 (d, J=2.3 Hz, 1H), 6.96 (dd, J=8.6, 2.4 Hz, 1H), 6.42 (dd, J=17.3, 1.4 Hz, 1H), 6.15 (dd, J=17.3, 10.4 Hz, 1H), 5.84 (dd, J=10.4, 1.4 Hz, 1H), 4.18 (t, J=6.8 Hz, 2H), 4.06 (t, J=6.5 Hz, 2H), 2.74–2.66 (m, 2H), 1.85 (dt, J=14.4, 6.6 Hz, 2H), 1.69 (dq, J=10.2, 5.1, 3.6 Hz, 2H), 1.50 (p, J=7.0 Hz, 2H), 1.44–1.29 (m, 20H), 0.94 (t, J=6.9 Hz, 3H).

Product 12w—¹H NMR (500 MHz, DMSO-d₆) δ 7.94 (s, 1H), 7.66 (d, J=8.8 Hz, 1H), 7.64 (s, 1H), 7.57 (d, J=8.0 Hz, 1H), 7.43 (d, J=7.8 Hz, 1H), 7.05 (d, J=2.3 Hz, 1H), 6.98 (dd, J=8.6, 2.4 Hz, 1H), 6.31 (dd, J=17.3, 1.6 Hz, 1H), 6.17 (dd, J=17.3, 10.3 Hz, 1H), 5.93 (dd, J=10.3, 1.6 Hz, 1H), 4.15–4.04 (m, 2H), 2.75–2.69 (m, 2H), 1.75 (p, J=6.6 Hz, 2H), 1.68–1.57 (m, 4H), 1.43 (p, J=6.9 Hz, 2H), 1.38–1.23 (m, 22H), 0.89 (t, J=7.0 Hz, 3H).

Product 12x—¹H NMR (500 MHz, Chloroform-d) δ 7.61–7.57 (m, 2H), 7.43 (d, J=8.1 Hz, 1H), 7.40 (d, J=9.3 Hz, 1H), 7.34 (d, J=7.8 Hz, 1H), 6.88 (d, J=6.7 Hz, 2H), 6.42 (dd, J=17.3, 1.3 Hz, 1H), 6.15 (dd, J=17.4, 10.4 Hz, 1H), 5.83 (dd, J=10.4, 1.3 Hz, 1H), 4.18 (t, J=6.8 Hz, 2H), 4.06 (t, J=6.5 Hz, 2H), 2.75–2.67 (m, 2H), 1.85 (p, J=6.6 Hz, 2H), 1.69 (p, J=6.8 Hz, 4H), 1.50 (p, J=7.3 Hz, 2H), 1.44–1.25 (m, 22H), 0.94 (t, J=6.8 Hz, 3H).

Product 12y—¹H NMR (500 MHz, Chloroform-d) δ 7.69 (s, 1H), 7.51 (dd, J=7.8, 1.8 Hz, 1H), 7.45–7.42 (m, 1H), 7.41 (d, J=8.3 Hz, 1H), 7.38–7.34 (m, 2H), 6.90–6.85 (m, 2H), 6.09 (s, 1H), 5.56–5.51 (m, 1H), 4.14 (t, J=6.7 Hz, 2H), 4.04 (t, J=6.5 Hz, 2H), 1.94 (t, J=1.2 Hz, 3H), 1.88–1.79 (m, 2H), 1.73–1.62 (m, 2H), 1.51–1.44 (m, 2H), 1.41–1.27 (m, 14H).

Product 12z—¹H NMR (500 MHz, Chloroform-d) δ 7.70 (s, 1H), 7.43 (d, J=7.7 Hz, 1H), 7.42 (d, J=8.6 Hz, 1H), 7.21–7.16 (m, 2H), 6.93–6.86 (m, 2H), 6.42 (dd, J=17.4, 1.4 Hz, 1H), 6.15 (dd, J=17.3, 10.4 Hz, 1H), 5.83 (dd, J=10.4, 1.4 Hz, 1H), 4.18 (t, J=6.8 Hz, 2H), 4.06 (t, J=6.5 Hz, 2H), 2.71–2.65 (m, 2H), 1.91–1.79 (m, 2H), 1.74–1.63 (m, 4H), 1.53–1.47 (m, 2H), 1.43–1.29 (m, 18H), 0.94 (t, J=6.9 Hz, 3H).

Example 13

General Polymerization Procedure

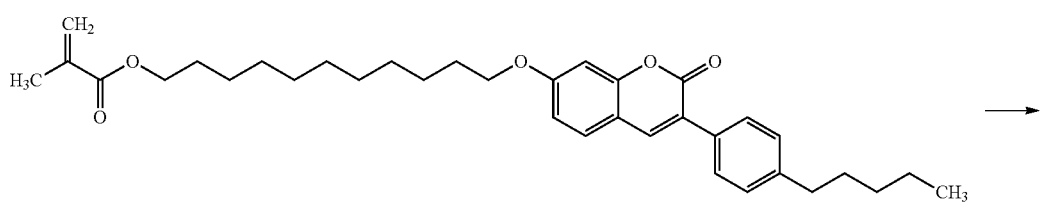

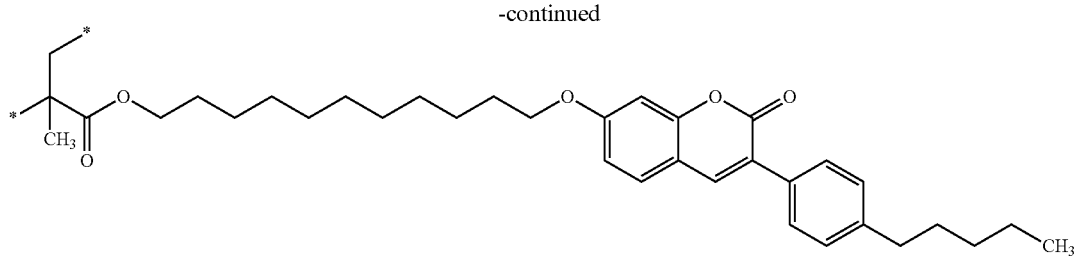

1.00 g (1.83 mmol) 2-Methyl-acrylic acid 11-[3-(4-pentyl-phenyl)-coumarin-7-yloxy]-undecyl undecyl ester is dissolved in DMF (11 ml). The solution is degassed by three freeze-pump-thaw cycles. 12 mg (0.07 mmol) azobisisobutyronitrile are added to the solution and the reaction vessel is then placed in a 65° C. preheated oil bath for 3 d. At the end of the reaction, the mixture is poured into cold methanol (1 l). The precipitated polymer is collected by filtration and yielded 698 mg (70% of theory).

The following polymers 13a to 13r are prepared analogously:

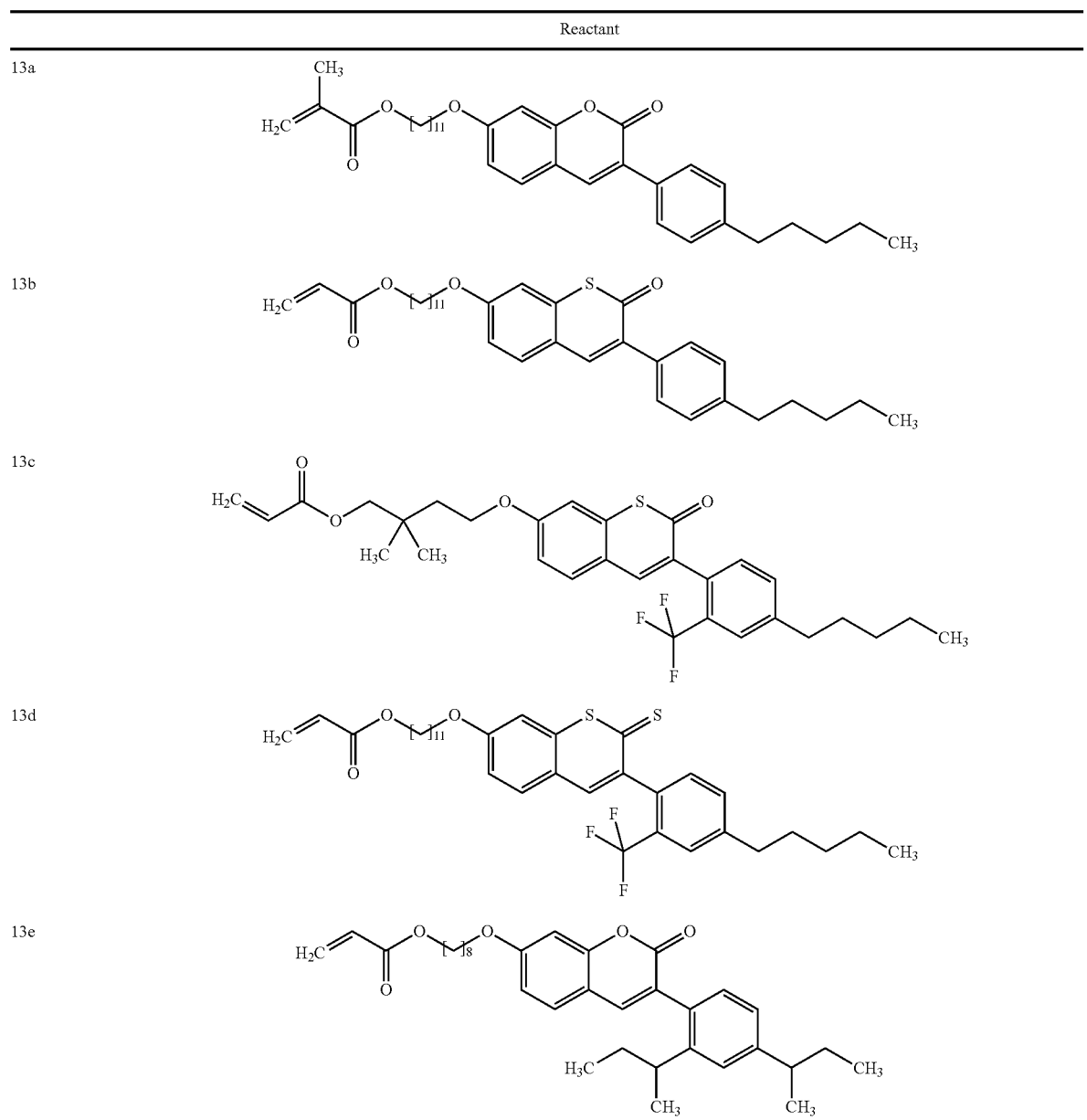

-continued
13f 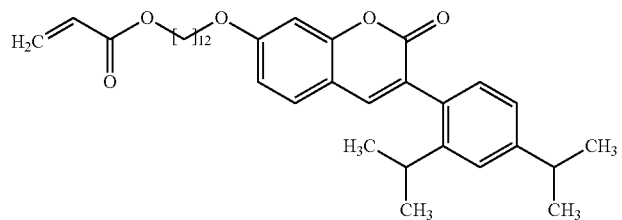
13g 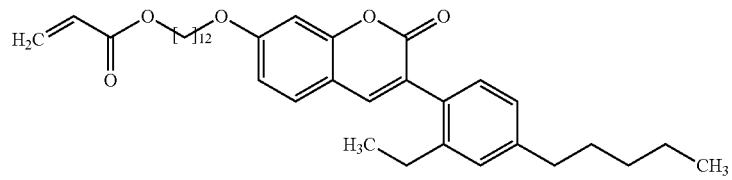
13h 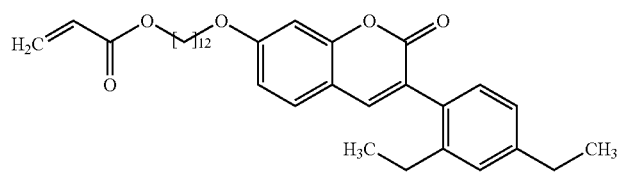
13i 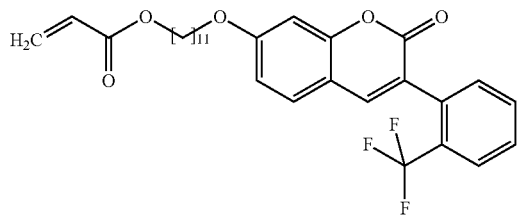
13j 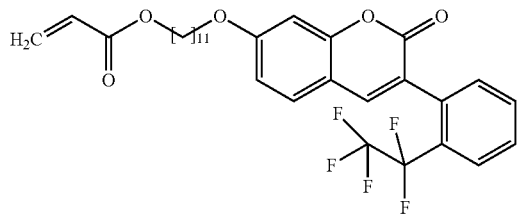
13k 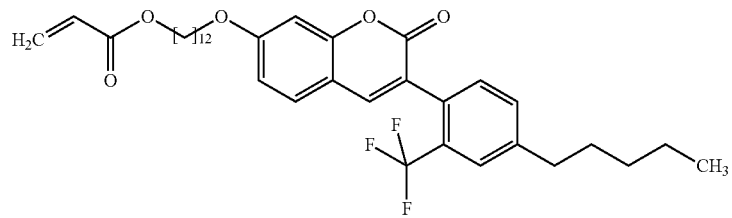
13l 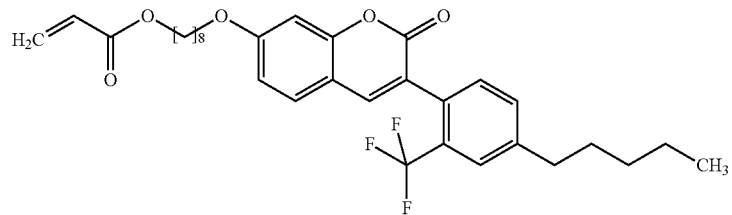

-continued
| | | |
|---|---|---|
| 13m | 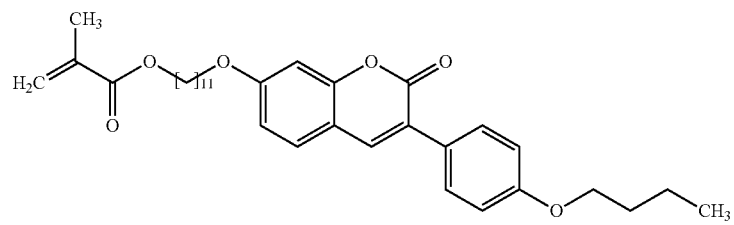 | |
| 13n | 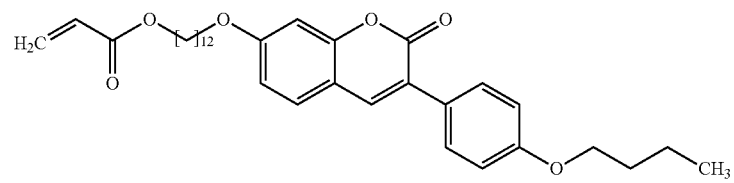 | |
| 13o | 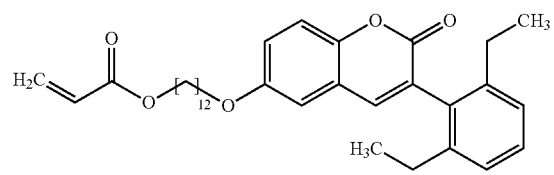 | |
| 13p | 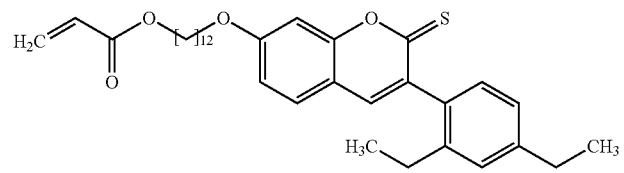 | |
| 13q | 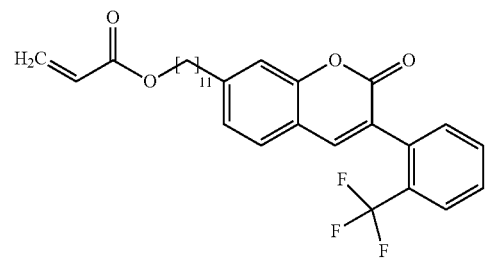 | |
| 13r | 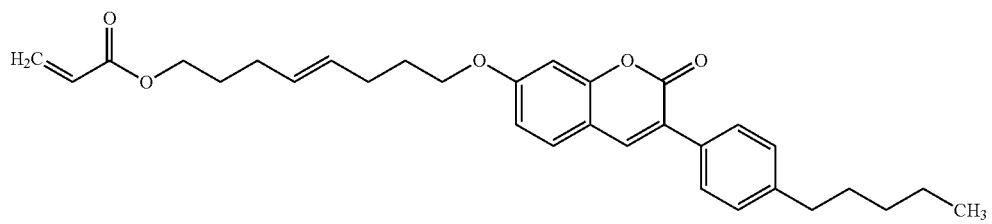 [SMILES: C=CC(=O)OCCC/C=C/CCCOc1ccc2cc(-c3ccc(CCCCC)cc3)c(=O)oc2c1] | |
| | Product | Yield |
|---|---|---|
| 13a | 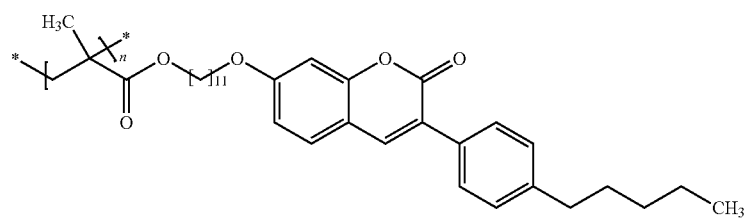 | 70% |

-continued
| | | |
|---|---|---|
| 13b | 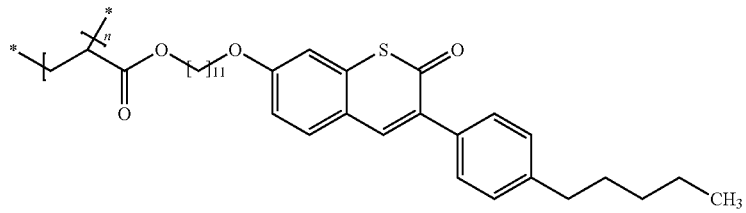 | 80% |
| 13c | 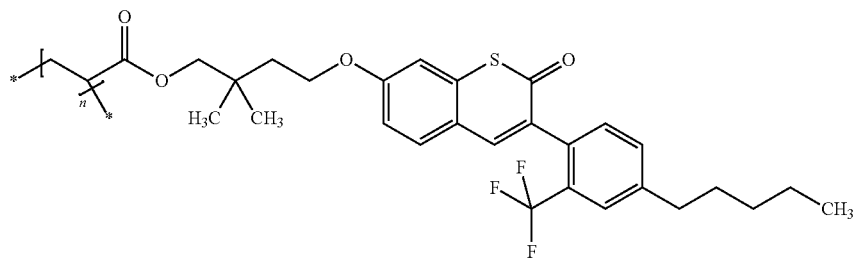 | 67% |
| 13d | 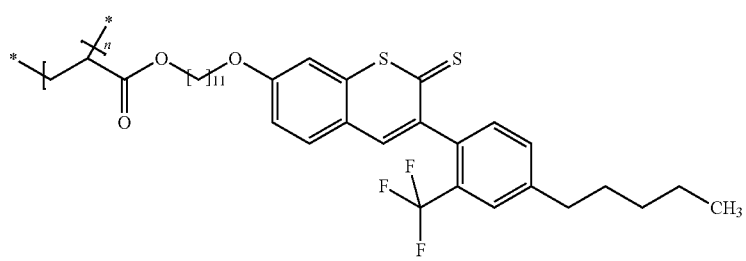 | 36% |
| 13e | 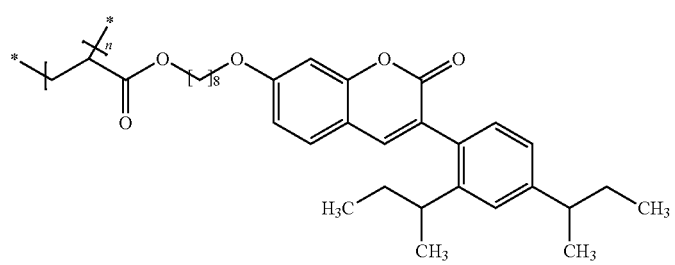 | 50% |
| 13f | 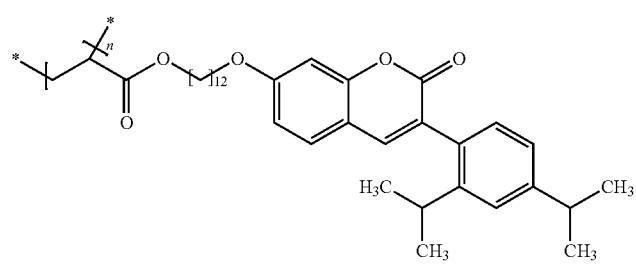 | 52% |
| 13g | 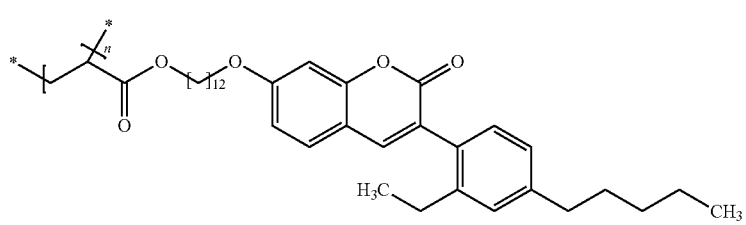 | 62% |

-continued
| | | |
|---|---|---|
| 13h | 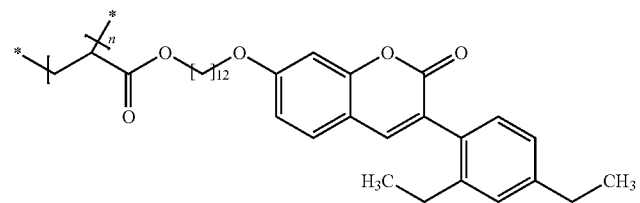 | 71% |
| 13i | 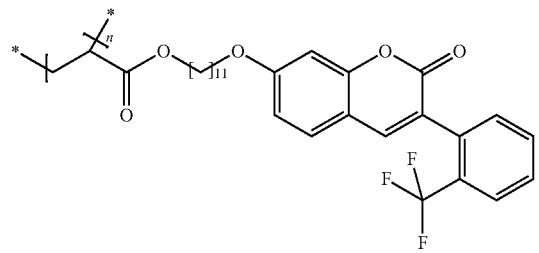 | 4% |
| 13j | 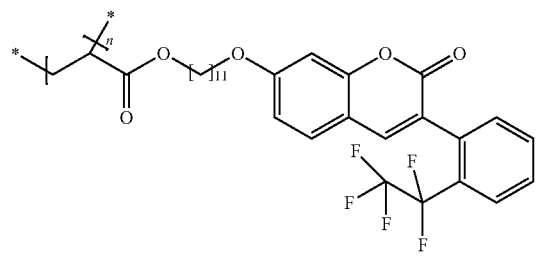 | 76% |
| 13k | 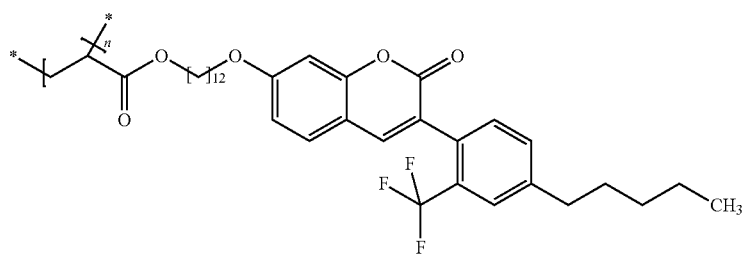 | 44% |
| 13l | 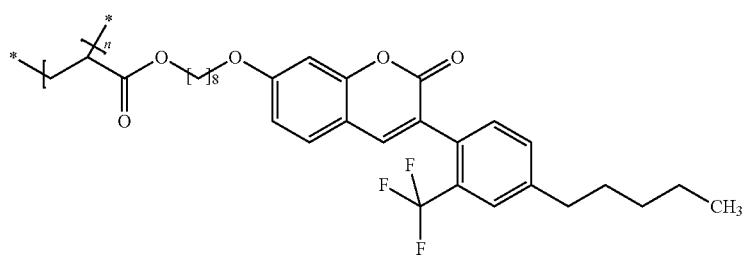 | 48% |
| 13m | 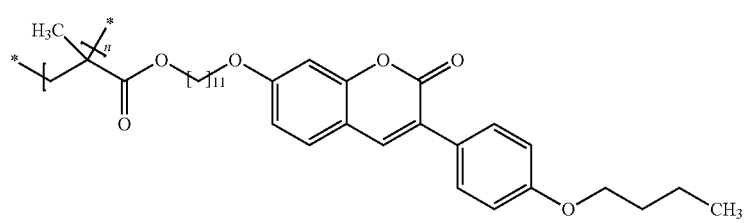 | 53% |

-continued

| | | % |
|---|---|---|
| 13n | 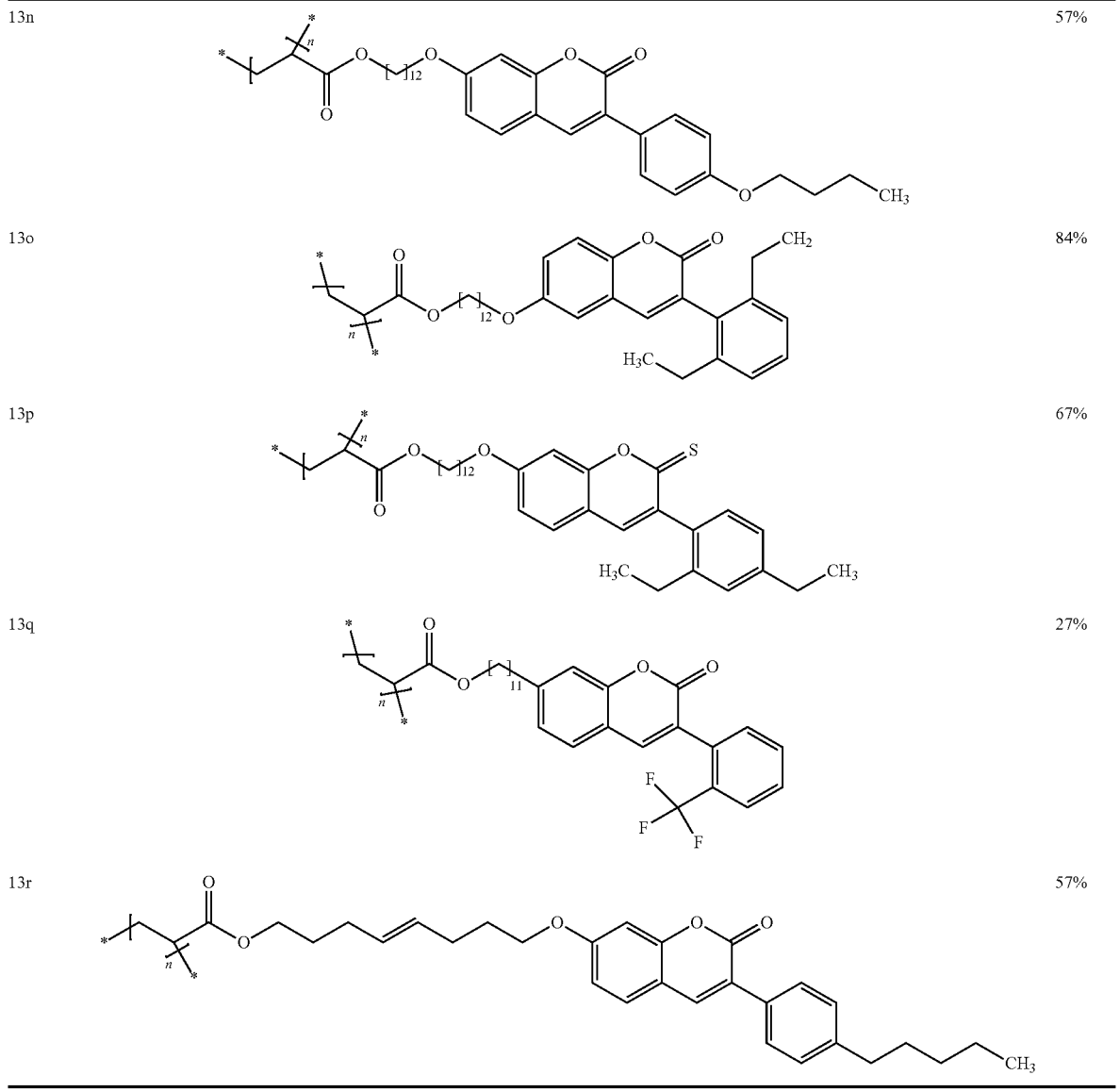 | 57% |
| 13o | | 84% |
| 13p | | 67% |
| 13q | | 27% |
| 13r | | 57% |

Example 14

3-[2-Ethyl-4-(6-hydroxy-hexyl)-phenyl]-7-methoxy-coumarin

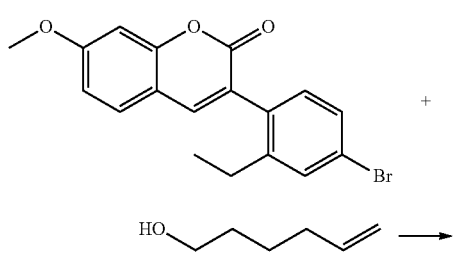

+

-continued

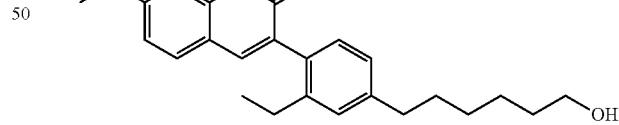

A solution of 5-Hexenol (1.00 ml; 8.35 mmol) in anhydrous 15 ml THF under argon at room temperature was treated dropwise with 9-Borabicyclo[3.3.1]nonane (0.5 M in THF) (20.04 ml; 10.02 mmol). The reaction was then heated 30 min at 90° C. The resulting solution was then transferred into a stirred mixture of 3-(4-Bromo-2-ethyl-phenyl)-7-methoxy-coumarin (750.00 mg; 2.09 mmol) and Tripotassium phosphate monohydrate (2.12 g; 9.19 mmol) in anhydrous Dimethylformamide (3.90 ml; 50.11 mmol) and Water (0.79 ml; 43.85 mmol) under argon. After bubbling argon through the reaction for 5 min at room temperature, Tetrakis(triphenylphosphine)palladium(0) (120.63 mg; 0.10 mmol)

was added. Then the reaction mixture was heated to 80° C. for 12 h. The cooled reaction mixture was then concentrated in vacuo, diluted with DCM and aqueous ammonia solution, the organic phase separated, washed with brine, dried over MgSO$_4$ and concentrated in vacuo. Chromatography Heptane/EtOAc gave 3-[2-Ethyl-4-(6-hydroxy-hexyl)-phenyl]-7-methoxy-coumarin (774.00 mg; 2.03 mmol; 97.4%). $^1$H NMR (500 MHz, DMSO-d$_6$) δ 7.92 (s, 1H), 7.66 (d, J=8.6 Hz, 1H), 7.15–7.11 (m, 2H), 7.06 (m, 2H), 6.99 (dd, J=8.6, 2.5 Hz, 1H), 3.88 (s, 3H), 3.40 (q, J=6.4 Hz, 2H), 2.60 (t, J=7.7 Hz, 2H), 2.50 (m, 2H), 1.63–1.57 (m, 2H), 1.47–1.39 (m, 2H), 1.37–1.30 (m, 4H), 1.08 (t, J=7.5 Hz, 3H).

The invention claimed is:

1. An optically active intraocular lens article which comprises, a copolymer comprising: one or more polymer units M$^1$ selected from units of the following formulae (P-1) to (P-63); and one or more different polymer units:

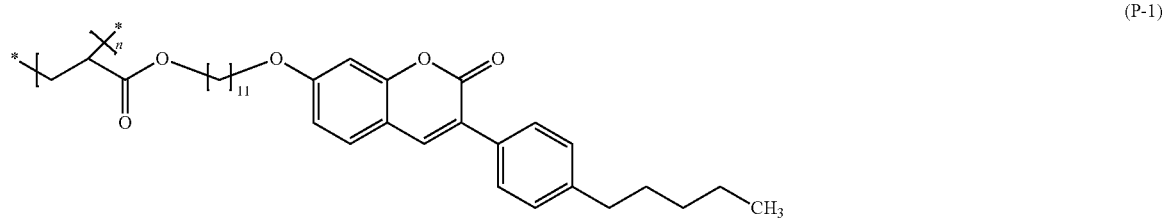

(P-1)

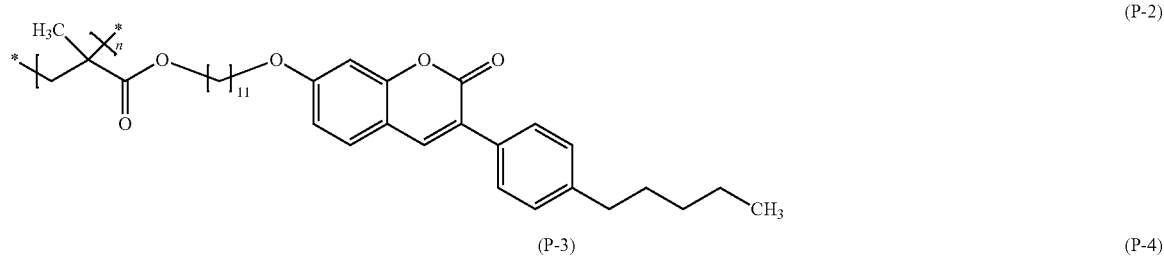

(P-2)

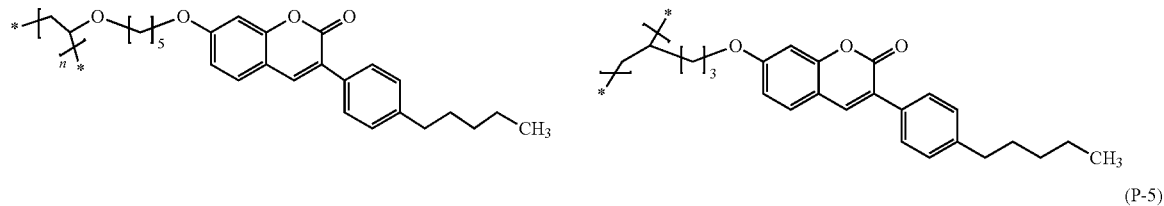

(P-3) (P-4)

(P-5)

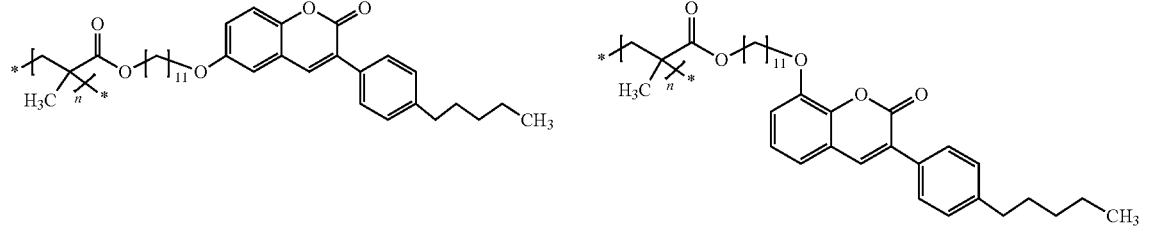

(P-6) (P-7)

(P-8)

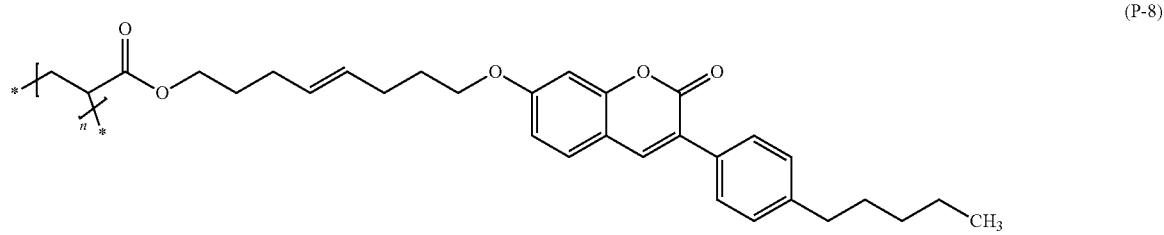

-continued
(P-9)
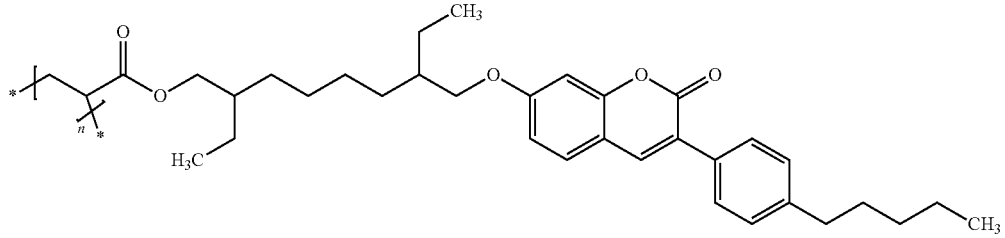
(P-10)
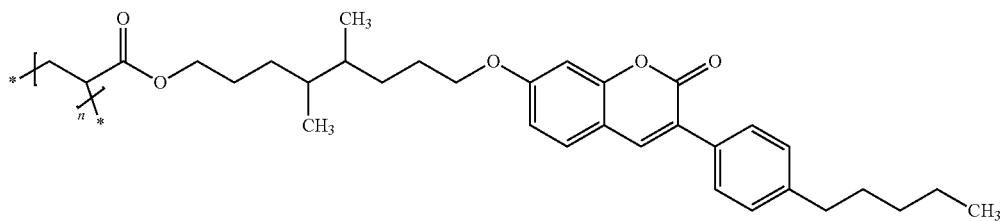
(P-11)
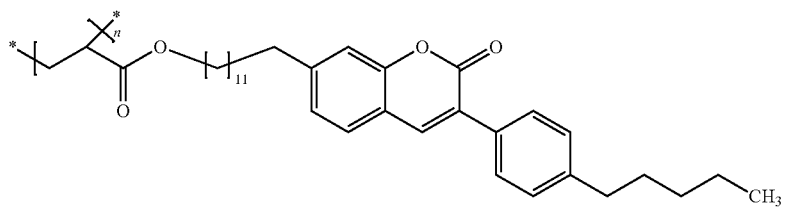
(P-12)
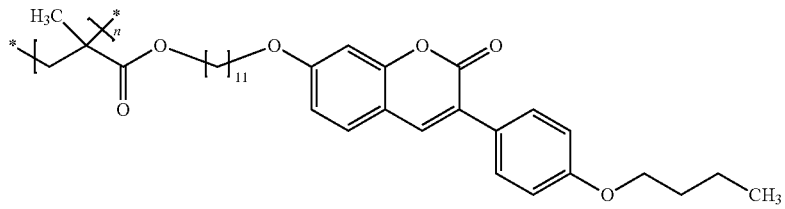
(P-13)
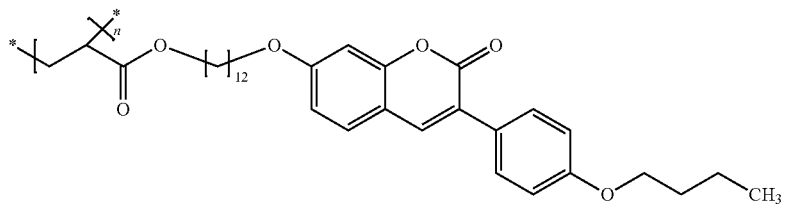
(P-14)
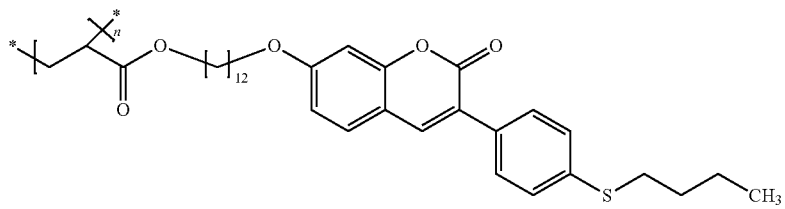
(P-15)
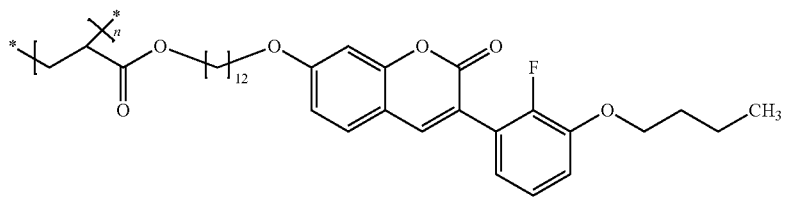

(P-16)
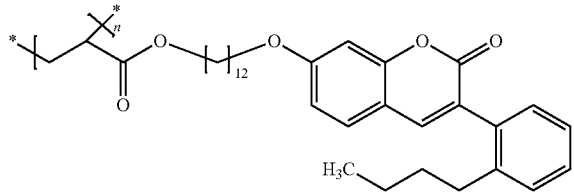
(P-17)
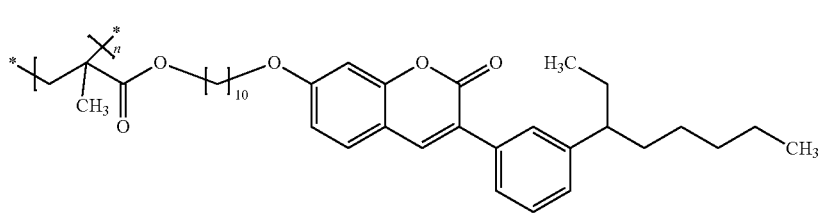
(P-18)
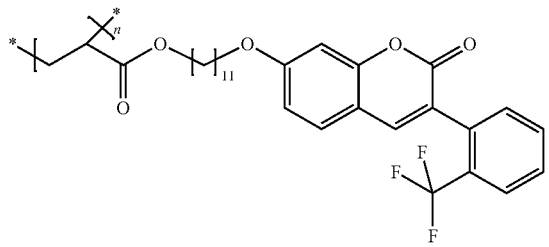
(P-19)
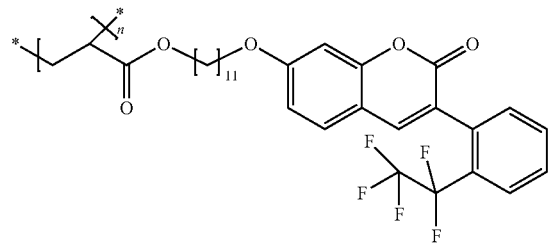
(P-20)
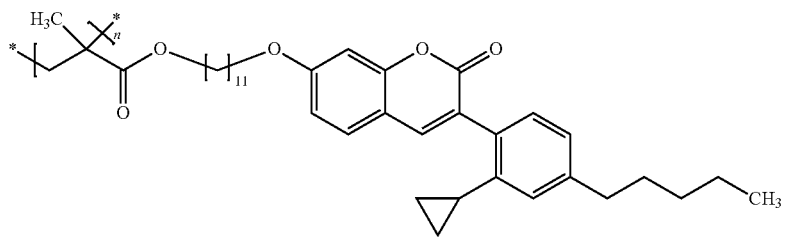
(P-21)
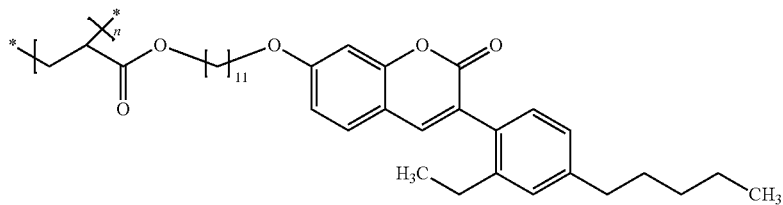
(P-22)
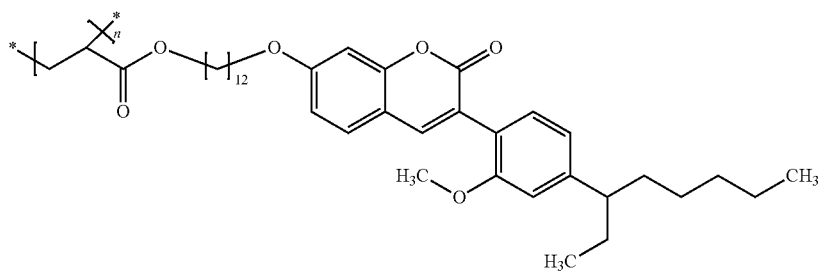

-continued
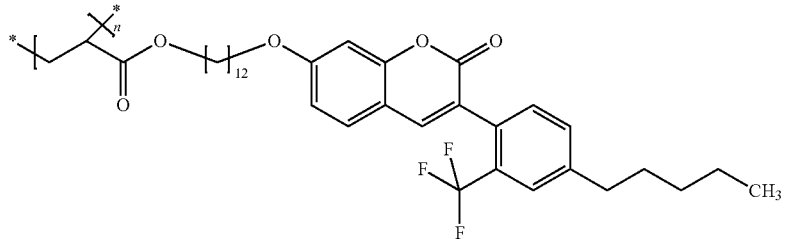
(P-23)
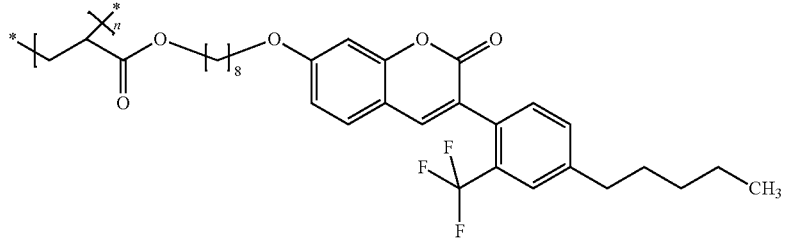
(P-24)
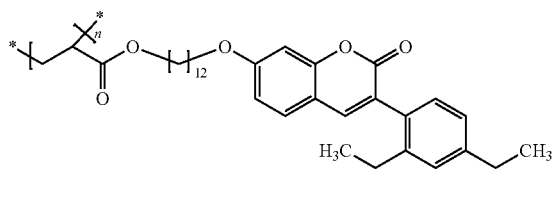
(P-25)
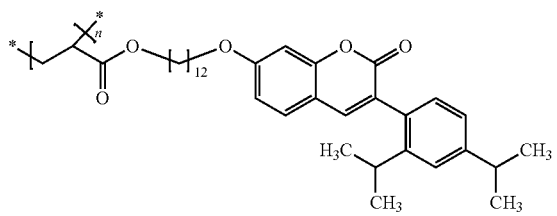
(P-26)
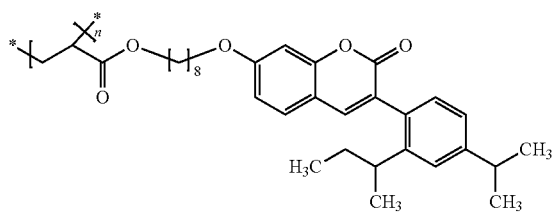
(P-27)
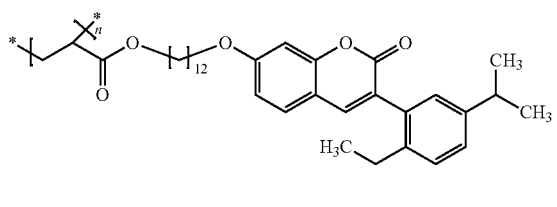
(P-28)
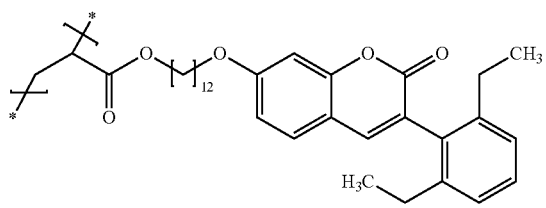
(P-29)
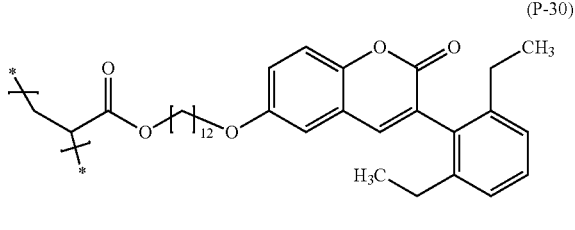
(P-30)
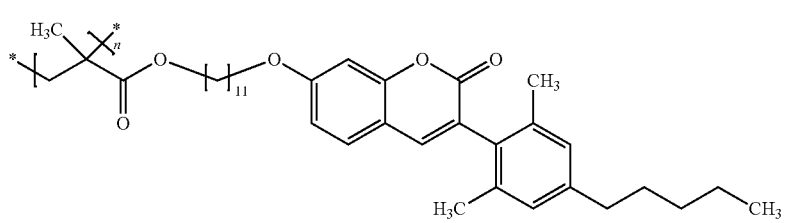
(P-31)

-continued
(P-32)
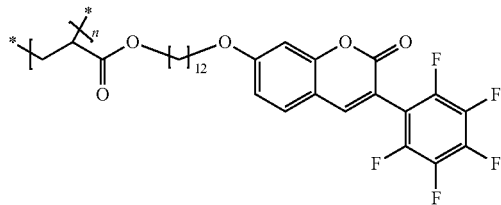
(P-33)
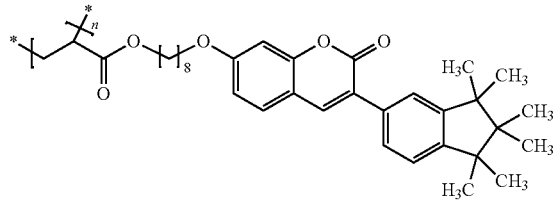
(P-34)
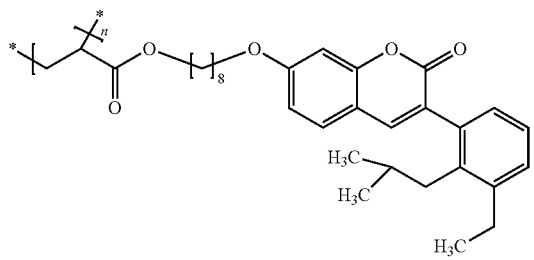
(P-35)
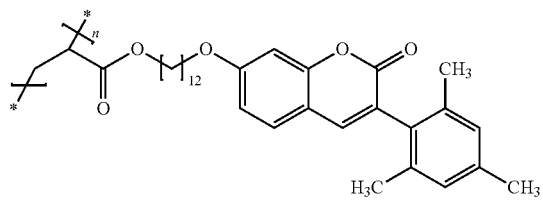
(P-36)
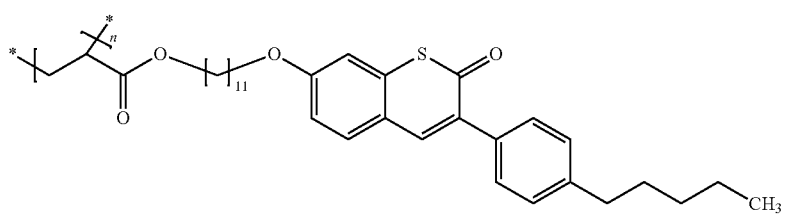
(P-37)
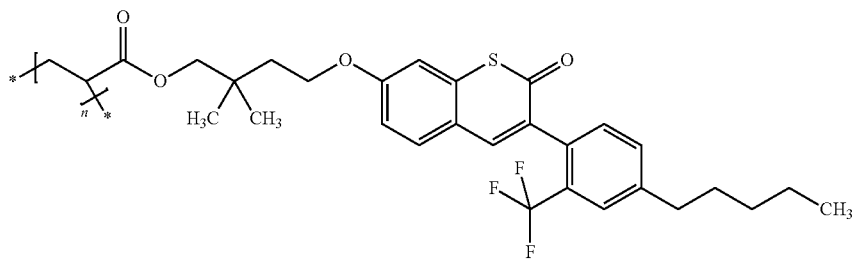
(P-38)
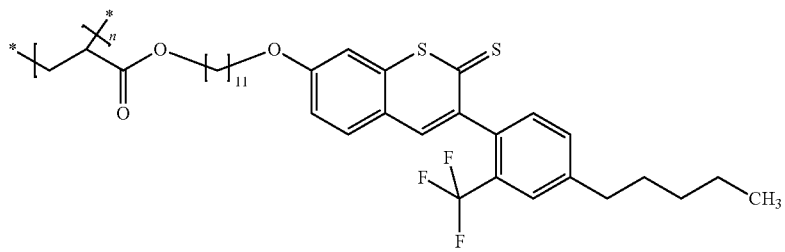
(P-39)
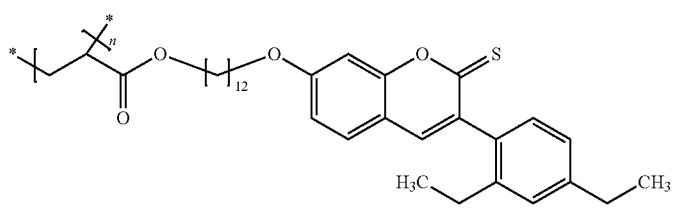

-continued
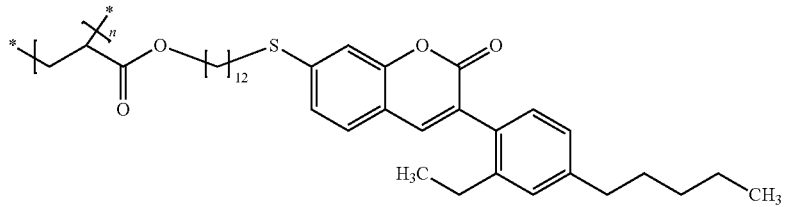
(P-40)
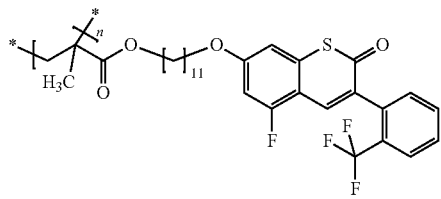
(P-41)
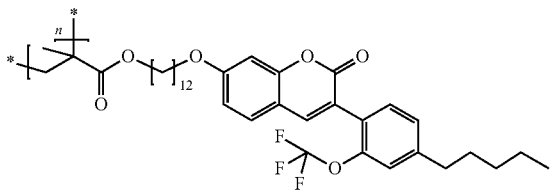
(P-42)
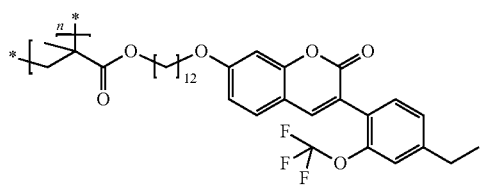
(P-43)
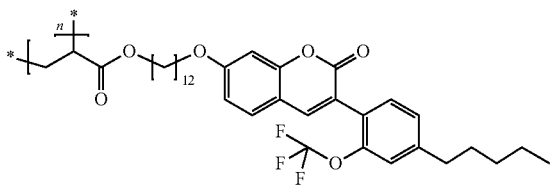
(P-44)
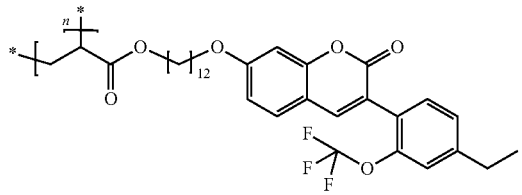
(P-45)
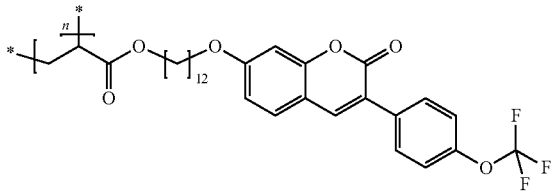
(P-46)
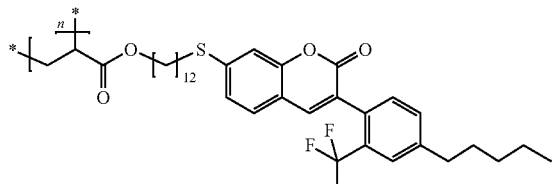
(P-47)
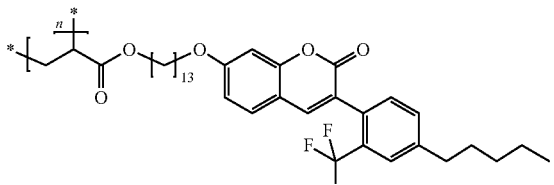
(P-48)
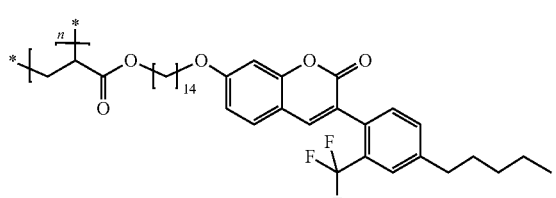
(P-49)
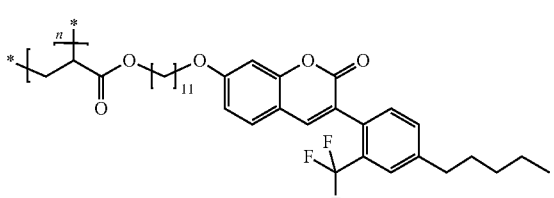
(P-50)
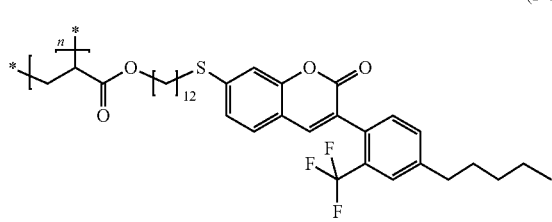
(P-51)
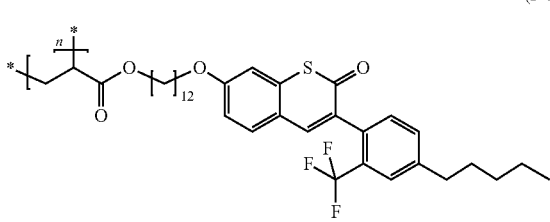
(P-52)

-continued

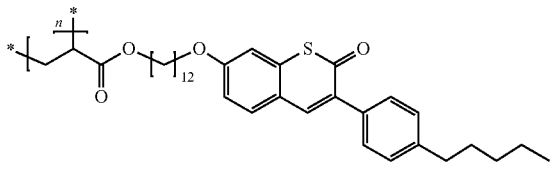
(P-53)

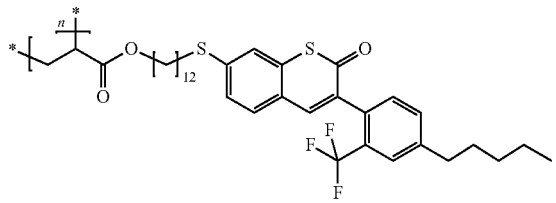
(P-54)

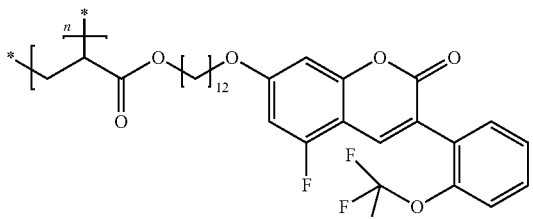
(P-55)

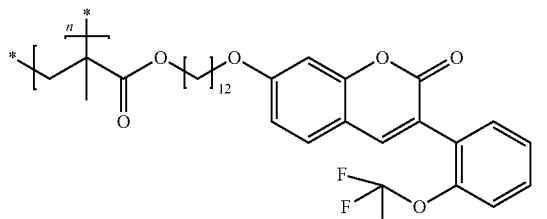
(P-56)

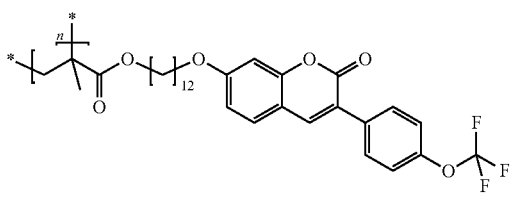
(P-57)

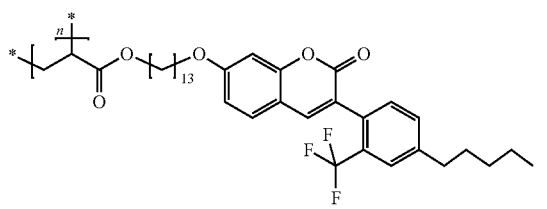
(P-58)

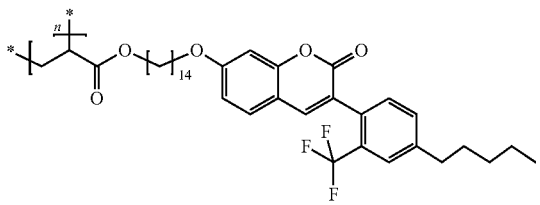
(P-59)

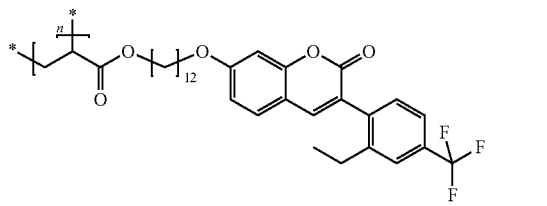
(P-60)

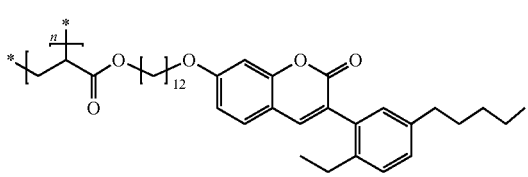
(P-61)

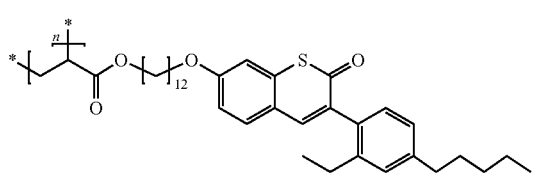
(P-62)

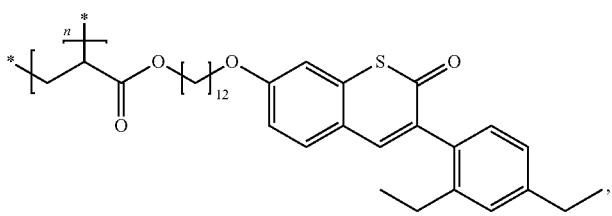
(P-63)

wherein,
each * in the formulae indicates a linkage to an adjacent unit of the copolymer, and
n indicates the number of units of the formula.

2. The intraocular lens article according to claim 1, wherein the one or more different polymer units in the copolymer comprise at least one unit $M^2$, which at each occurrence is independently selected from the group consisting of a polymerized unit derived from ethylene, propylene, an acrylate, a methacrylate and a styrene.

3. The intraocular lens article according to claim 2, wherein the copolymer comprises units $M^1$ and $M^2$ in a ratio $m_1:m_2$ of from 0.01 to 100.

4. The intraocular lens article according to claim 1, wherein intraocular lens article further comprises a UV absorber.

5. A process of forming the intraocular lens article of claim 1, said process comprising:
   a) providing a composition comprising the copolymer; and b) subsequently forming the intraocular lens article from said composition.

6. A process of changing the optical properties of an intraocular lens article of claim 1, said process comprising:
a) providing the intraocular lens article, and
b) subsequently exposing said article to irradiation having a wavelength of at least 200 nm and at most 1500 nm, whereby at least one optical property of the article is changed.

7. An intraocular lens article produced by the process according to claim 6.

8. The intraocular lens article according to claim 1, wherein one or more polymer units $M^1$ and/or one or more different polymer units in the copolymer are crosslinked with each other.

9. The intraocular lens article according to claim 1, wherein the lens article further comprises one or more optic components and one or more haptic components, wherein the one or more optic components serve as a lens and the one or more haptic components are attached to the one or more optic components and hold the one or more optic components in place in the eye.

10. The intraocular lens article according to claim 9, wherein the lens article has a one-piece design wherein the one or more optic components and the one or more haptic components are formed from a single piece of material.

11. The intraocular lens article according to claim 9, wherein the lens article has a multi-piece design wherein the one or more optic components and the one or more haptic components are formed separately and then combined.

12. A process of forming the intraocular lens article of claim 1, said process comprising:
a) polymerizing a compound according to formulae (M-1) to (M-63) together with precursor materials to produce the copolymer having one or more polymer units $M^1$ and the one or more different polymer units

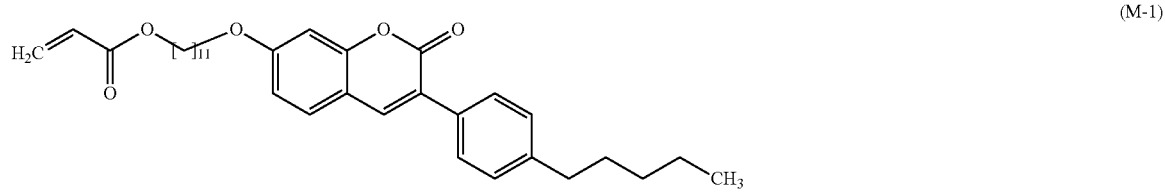
(M-1)

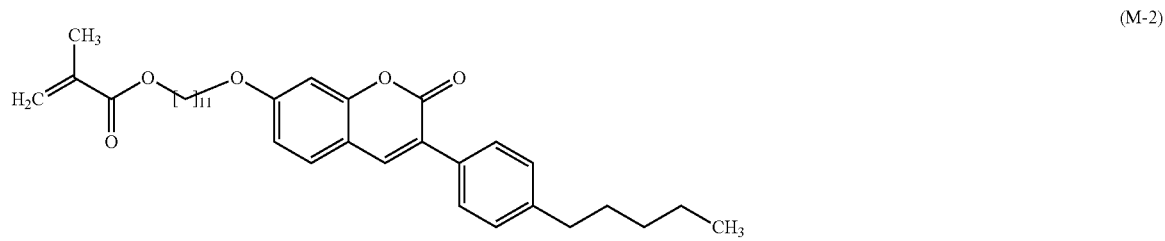
(M-2)

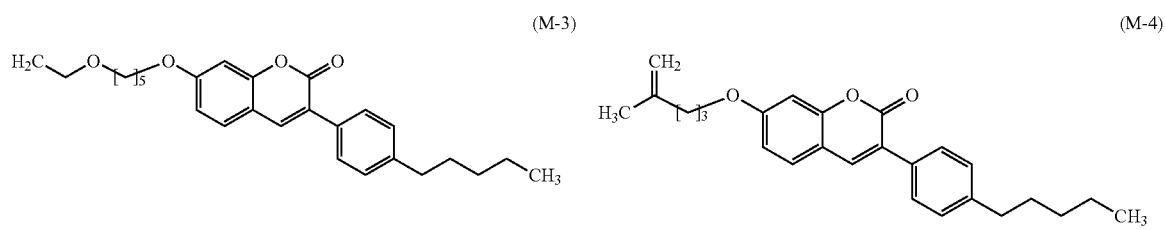
(M-3)     (M-4)

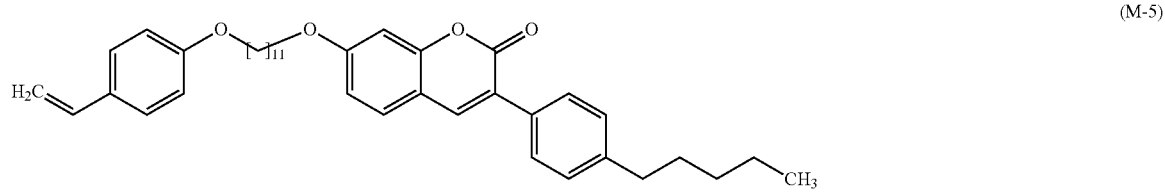
(M-5)

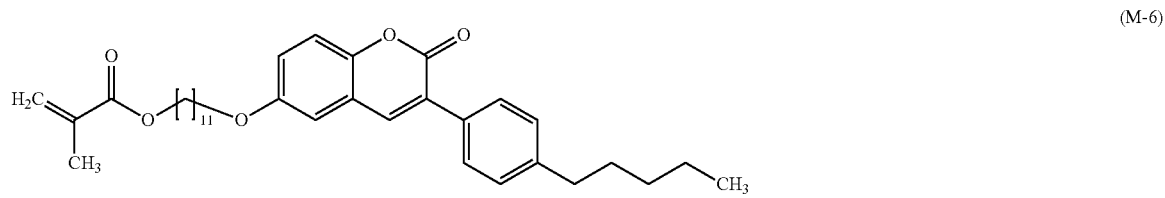
(M-6)

-continued
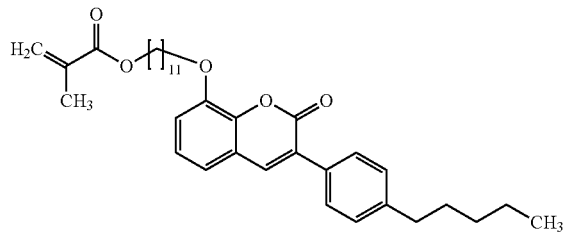
(M-7)
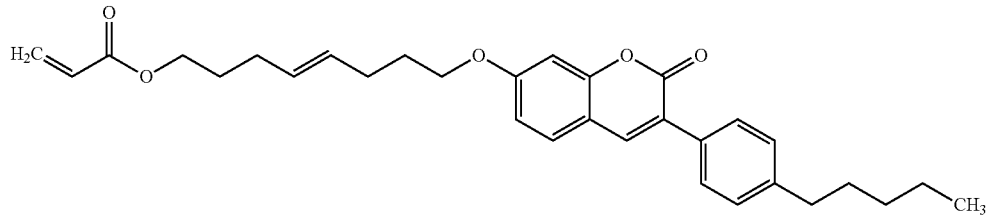
(M-8)
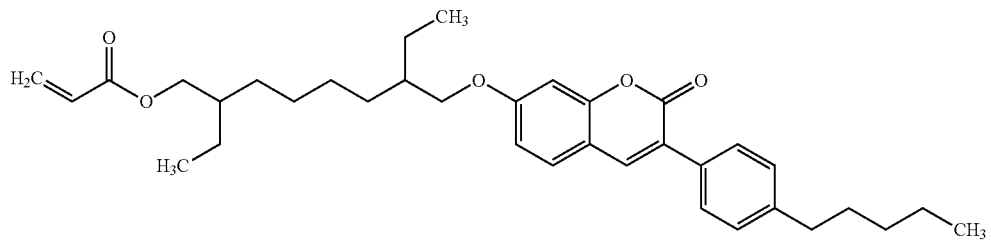
(M-9)
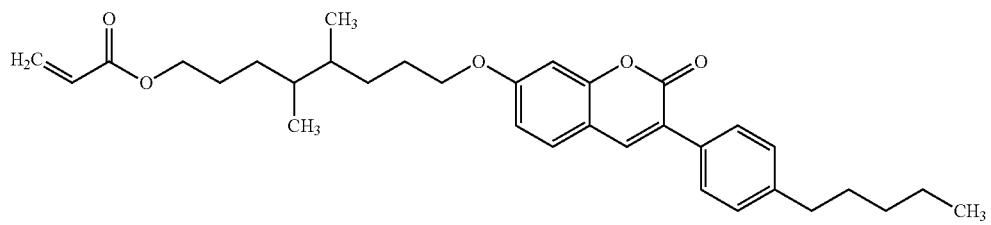
(M-10)
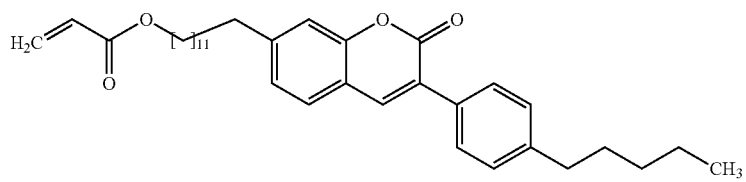
(M-11)
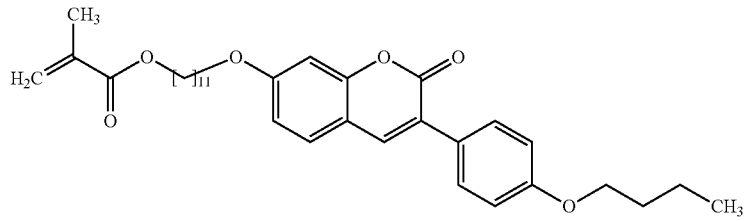
(M-12)
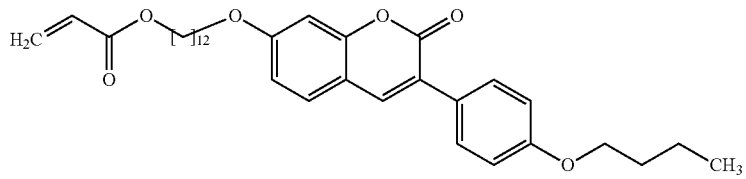
(M-13)

-continued
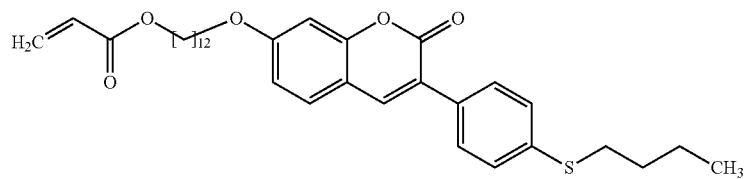
(M-14)
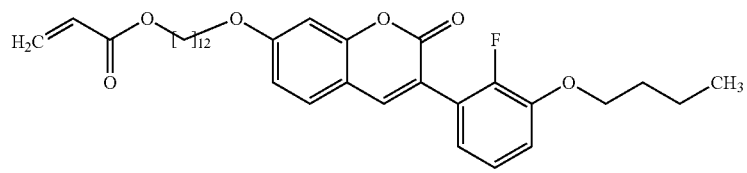
(M-15)
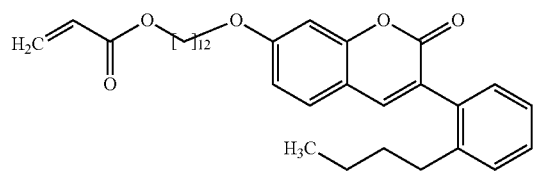
(M-16)
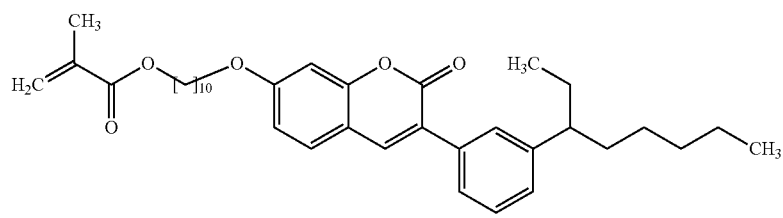
(M-17)
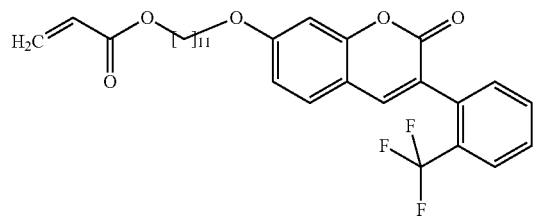
(M-18)
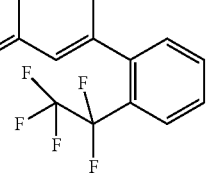
(M-19)
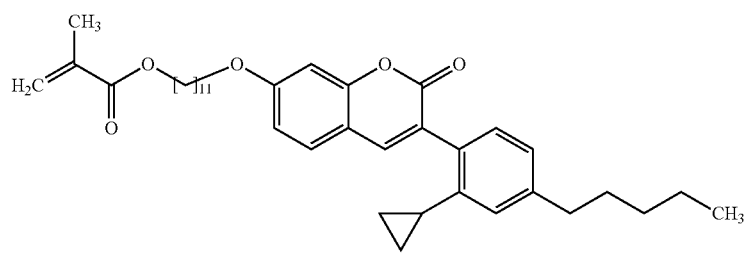
(M-20)
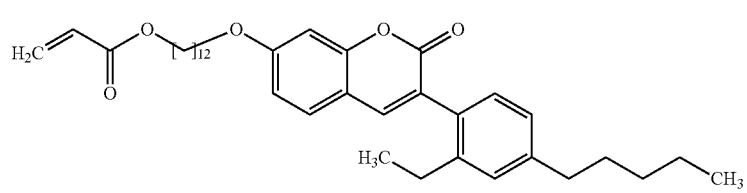
(M-21)

-continued
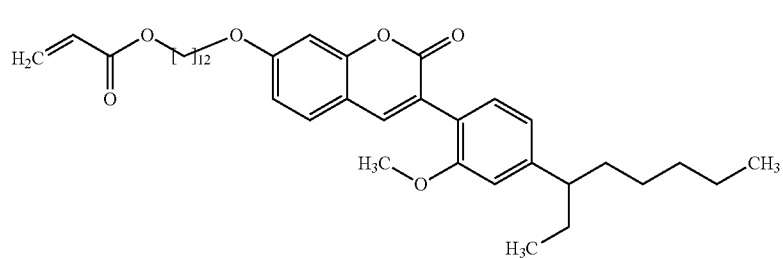
(M-22)
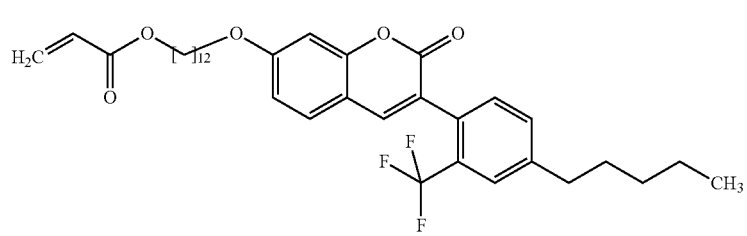
(M-23)
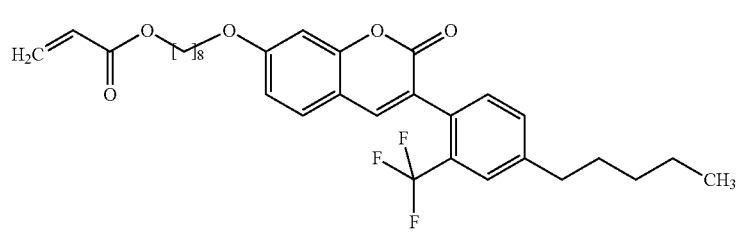
(M-24)
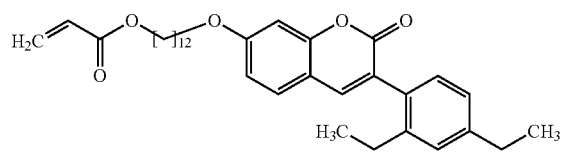
(M-25)
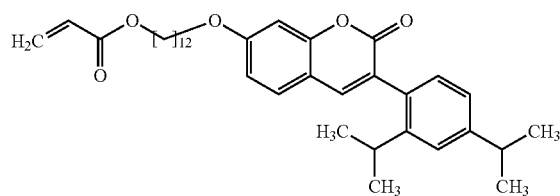
(M-26)
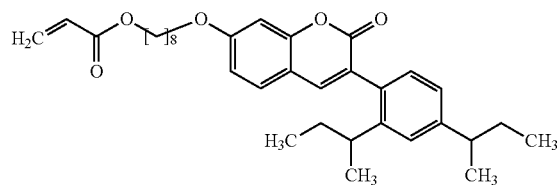
(M-27)
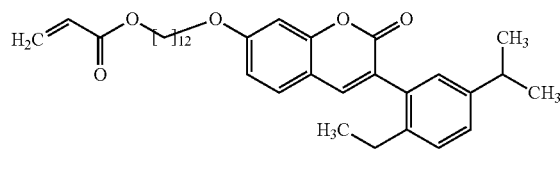
(M-28)
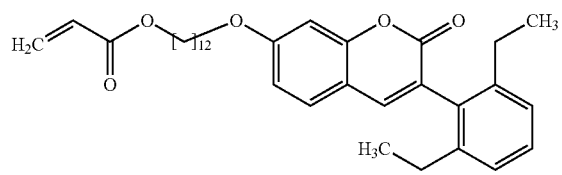
(M-29)
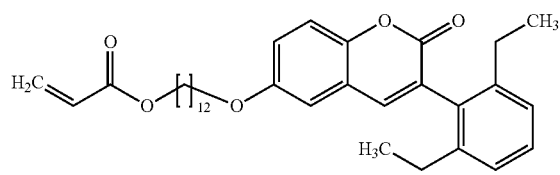
(M-30)
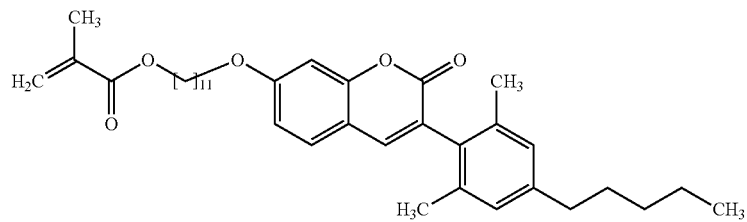
(M-31)

-continued
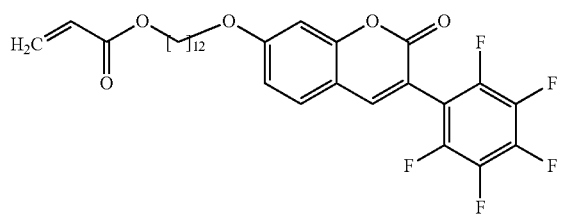
(M-32)
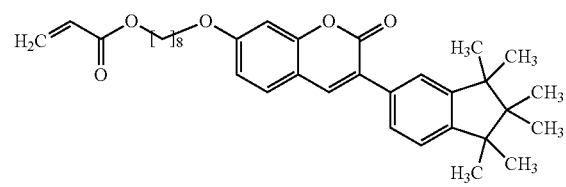
(M-33)
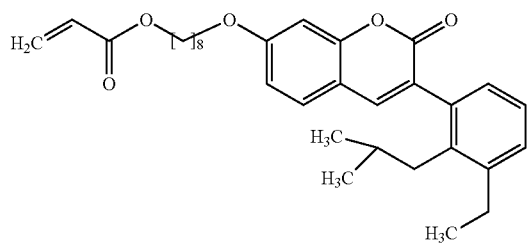
(M-34)
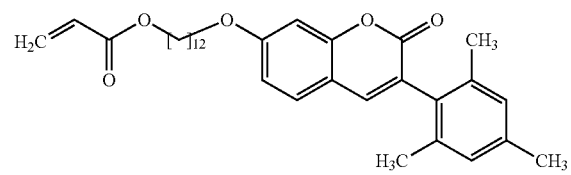
(M-35)
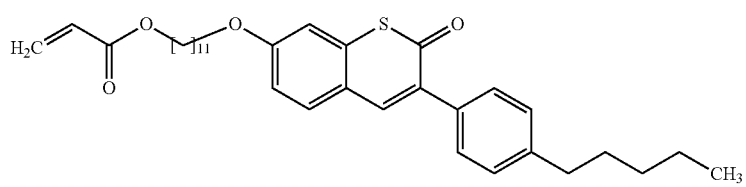
(M-36)
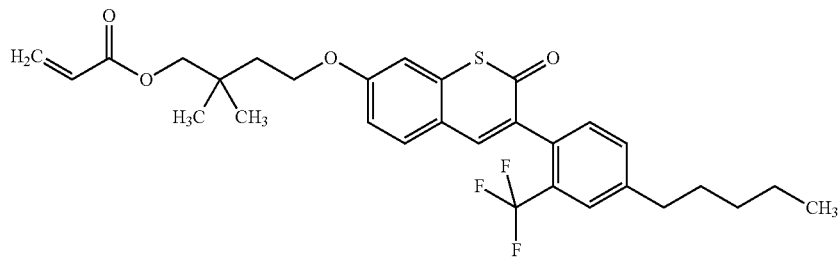
(M-37)
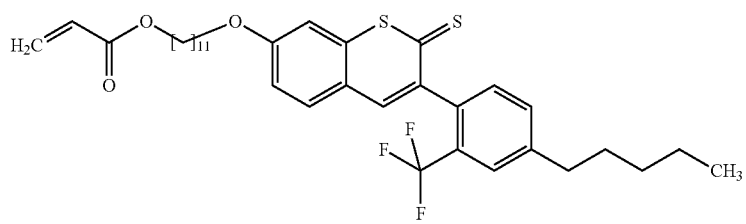
(M-38)
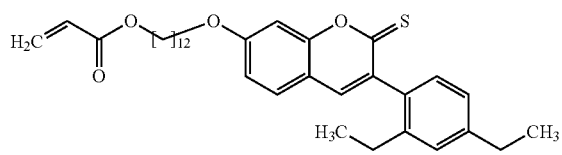
(M-39)
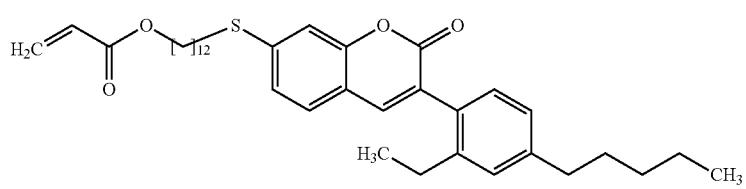
(M-40)

-continued
(M-41)
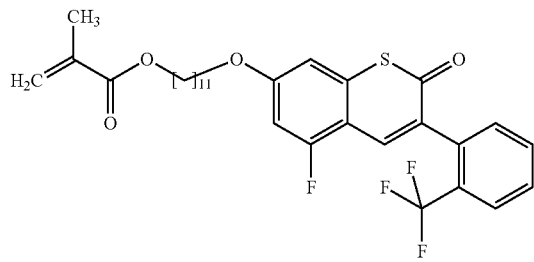
(M-42)
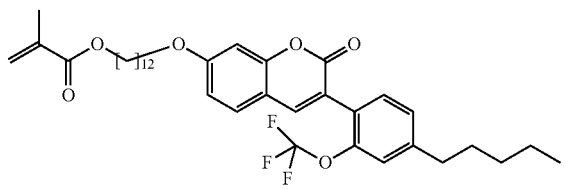
(M-43)
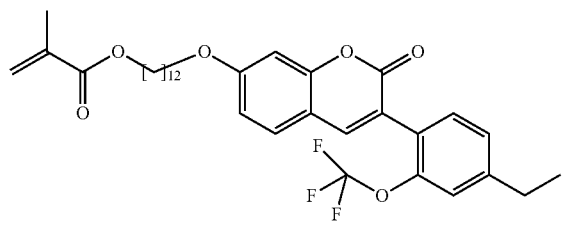
(M-44)
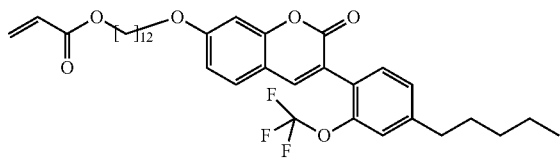
(M-45)
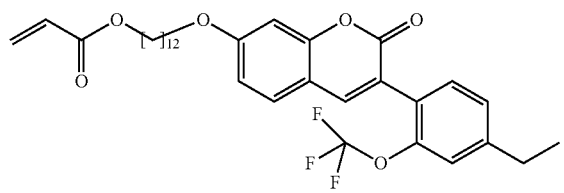
(M-46)
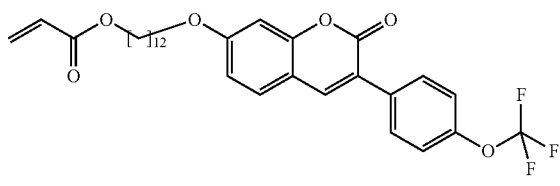
(M-47)
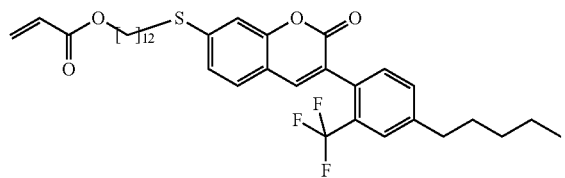
(M-48)
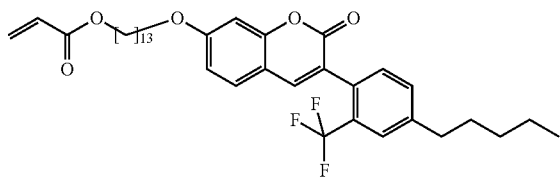
(M-49)
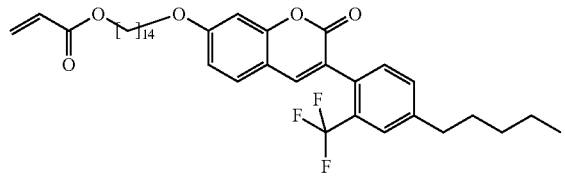
(M-50)
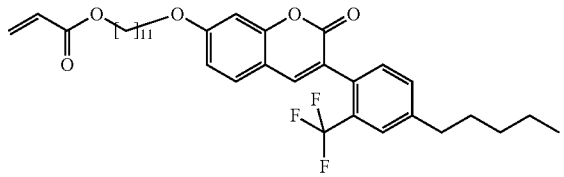
(M-51)
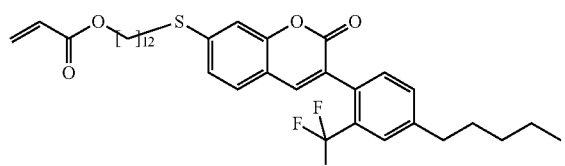
(M-52)
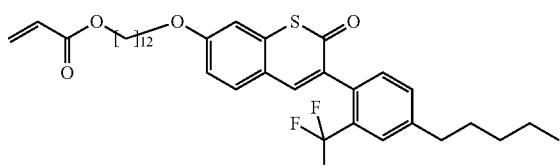
(M-53)
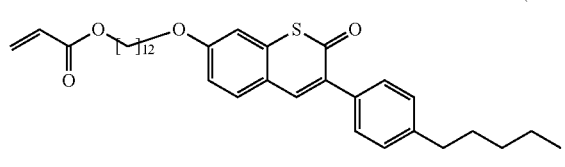
(M-54)
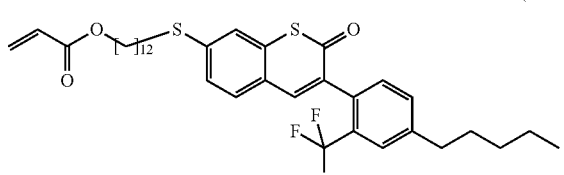

-continued
(M-55) 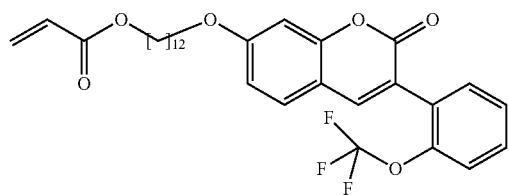
(M-56) 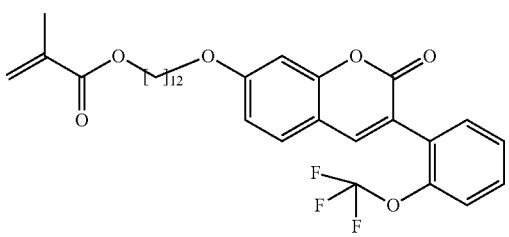
(M-57) 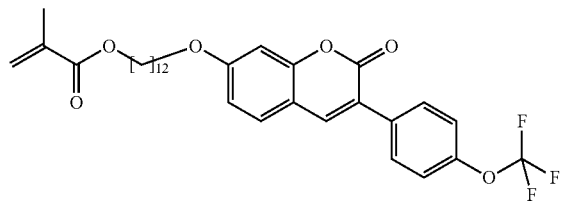
(M-58) 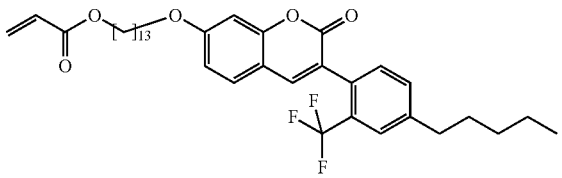
(M-59) 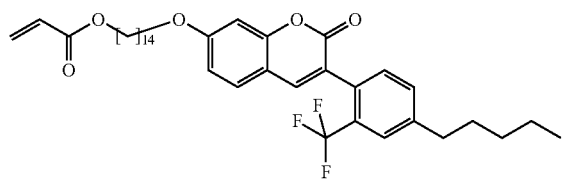
(M-61) 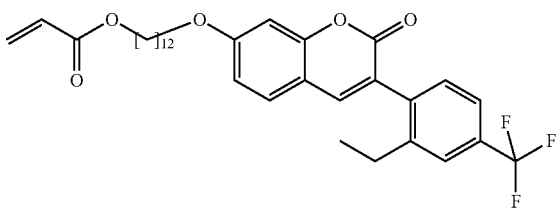
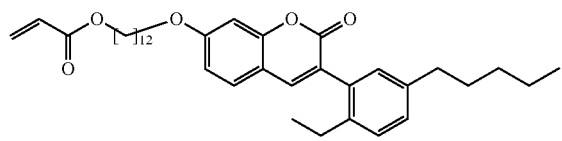
(M-63) 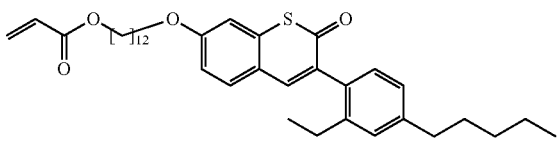
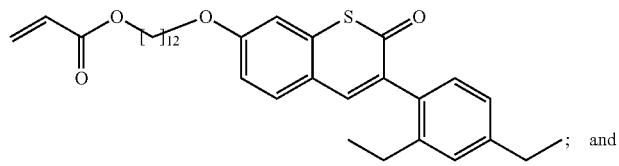
; and
b) subsequently forming the intraocular lens article from said composition.
* * * * *